United States Patent
Stamford et al.

(10) Patent No.: US 8,541,427 B2
(45) Date of Patent: Sep. 24, 2013

(54) PHENYL-SUBSTITUTED 2-IMINO-3-METHYL PYRROLO PYRIMIDINONE COMPOUNDS AS BACE-1 INHIBITORS, COMPOSITIONS, AND THEIR USE

(75) Inventors: Andrew W. Stamford, Chatham Township, NJ (US); Zhaoning Zhu, Plainsboro, NJ (US); Mihirbaran Mandal, Scotch Plains, NJ (US); Yusheng Wu, Kenilworth, NJ (US); Jared N. Cumming, Kenilworth, NJ (US); Xiaoxiang Liu, River Vale, NJ (US); Guoqing Li, Kenilworth, NJ (US); Ulrich Iserloh, Hoboken, NJ (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 244 days.

(21) Appl. No.: 12/988,461

(22) PCT Filed: Apr. 21, 2009

(86) PCT No.: PCT/US2009/041202
§ 371 (c)(1),
(2), (4) Date: Dec. 22, 2010

(87) PCT Pub. No.: WO2009/131975
PCT Pub. Date: Oct. 29, 2009

(65) Prior Publication Data
US 2011/0110957 A1      May 12, 2011

Related U.S. Application Data

(60) Provisional application No. 61/047,006, filed on Apr. 22, 2008.

(51) Int. Cl.
| C07D 487/04 | (2006.01) |
| A61K 31/519 | (2006.01) |
| A61P 25/28 | (2006.01) |
| A61P 3/10 | (2006.01) |

(52) U.S. Cl.
USPC ........................................ 514/265.1; 544/280

(58) Field of Classification Search
USPC ...................................... 544/280; 514/265.1
See application file for complete search history.

(56) References Cited

U.S. PATENT DOCUMENTS

| 2005/0282826 A1 | 12/2005 | Malamas et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0099875 A1 | 5/2007 | Zhu et al. |
| 2007/0203116 A1 | 8/2007 | Quagliato et al. |
| 2007/0232642 A1 | 10/2007 | Baxter et al. |
| 2007/0259898 A1 | 11/2007 | Baxter et al. |
| 2007/0287692 A1 | 12/2007 | Wu et al. |
| 2007/0299087 A1 | 12/2007 | Berg et al. |
| 2008/0051420 A1 | 2/2008 | Berg et al. |
| 2008/0058349 A1 | 3/2008 | Berg et al. |
| 2008/0161269 A1 | 7/2008 | Berg et al. |
| 2008/0214577 A1 | 9/2008 | Berg et al. |
| 2008/0287460 A1 | 11/2008 | Burrows et al. |
| 2008/0287462 A1 | 11/2008 | Chessari et al. |
| 2009/0023762 A1 | 1/2009 | Berg et al. |
| 2009/0062282 A1 | 3/2009 | Albert et al. |
| 2009/0209529 A1 | 8/2009 | Andreini et al. |

FOREIGN PATENT DOCUMENTS

| WO | 2005/014540 A1 | 2/2005 |
| WO | 2005/016876 A1 | 2/2005 |
| WO | 2005/058311 A1 | 6/2005 |
| WO | 2006/009653 A1 | 1/2006 |
| WO | 2006/014762 A1 | 2/2006 |
| WO | 2006/014944 A1 | 2/2006 |
| WO | 2006/065277 A1 | 2/2006 |
| WO | 2006/138192 A1 | 2/2006 |

(Continued)

OTHER PUBLICATIONS

Baxter, Ellen, et. al.; Journal of Medicinal Chemistry; vol. 50, No. 18, Sep. 6, 2007; "2-Amino-3,4-dihydroquinazolines as Inhibitors of BACE-1 . . . "; Published on Web on Aug. 8, 2007.

(Continued)

*Primary Examiner* — Susanna Moore
(74) *Attorney, Agent, or Firm* — Keith D. MacMillan; Gerard M. Devlin

(57) ABSTRACT

In its many embodiments, the present invention provides certain 2-imino-3-methyl pyrrolo pyrimidone compounds, including compounds Formula (II): and include tautomers, steroisomers, or pharmaceutically acceptable salts or solvates of said compounds, stereoisomers, or said tautomers, wherein $R^2$, $R^3$, $R^4$, $R^5$, $R^6$, $R^7$, $R^8$, and $R^9$ are each selected independently and as defined herein. Pharmaceutical compositions comprising one or more such compounds, and methods for their preparation and use in treating pathologies associated with amyloid beta (Aβ) protein, including Alzheimer's Disease, are also disclosed.

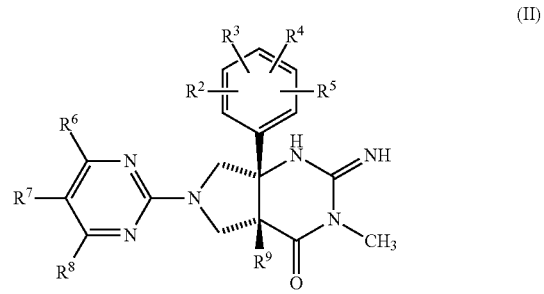

(II)

21 Claims, No Drawings

(56) References Cited

FOREIGN PATENT DOCUMENTS

| WO | WO 2006/017836 A2 | 2/2006 |
|---|---|---|
| WO | WO 2006/017844 A1 | 2/2006 |
| WO | WO 2006/024932 A1 | 3/2006 |
| WO | WO 2006/076284 A2 | 7/2006 |
| WO | 2006/138195 A1 | 9/2006 |
| WO | 2006/138217 A1 | 12/2006 |
| WO | 2006/138264 A1 | 12/2006 |
| WO | 2007/005366 A1 | 12/2006 |
| WO | 2007/005404 A1 | 1/2007 |
| WO | 2007/016012 A1 | 1/2007 |
| WO | 2007/038271 A1 | 2/2007 |
| WO | 2007/050721 A1 | 4/2007 |
| WO | 2007/053506 A1 | 5/2007 |
| WO | WO 2007/049532 A1 | 5/2007 |
| WO | WO 2007/050612 A1 | 5/2007 |
| WO | WO 2007/092839 A2 | 8/2007 |
| WO | WO 2007/092846 A2 | 8/2007 |
| WO | WO 2007/092854 A2 | 8/2007 |
| WO | WO 2007/114771 A1 | 10/2007 |
| WO | 2007/145568 A1 | 12/2007 |
| WO | 2007/145569 A1 | 12/2007 |
| WO | 2007/145570 A1 | 12/2007 |
| WO | 2007/145571 A1 | 12/2007 |
| WO | 2007/146225 A1 | 12/2007 |
| WO | WO 2007/149033 A1 | 12/2007 |
| WO | WO 2008/022024 A2 | 2/2008 |
| WO | WO 2008/103351 A2 | 8/2008 |
| WO | WO 2008/133273 A1 | 11/2008 |
| WO | WO 2008/133274 A1 | 11/2008 |
| WO | WO 2009/005470 A1 | 1/2009 |
| WO | WO 2009/005471 A1 | 1/2009 |
| WO | WO 2009/022961 A1 | 2/2009 |
| WO | WO 2009/038686 A1 | 3/2009 |
| WO | WO 2009/059953 A1 | 5/2009 |
| WO | WO 2009/007300 A2 | 7/2009 |
| WO | WO 2009/091016 A1 | 7/2009 |
| WO | WO 2009/092566 A1 | 7/2009 |
| WO | WO 2009/097278 A1 | 8/2009 |
| WO | WO 2009/097401 A1 | 8/2009 |
| WO | WO 2009/108550 A1 | 9/2009 |
| WO | WO 2009/131974 A1 | 10/2009 |
| WO | WO 2009/131975 A1 | 10/2009 |
| WO | WO 2009/134617 A1 | 11/2009 |
| WO | WO 2009/151098 A1 | 12/2009 |
| WO | WO 2010/013302 A1 | 2/2010 |
| WO | WO 2010/013794 A1 | 2/2010 |
| WO | WO 2010/047372 A1 | 4/2010 |
| WO | WO 2010/056194 A1 | 5/2010 |

OTHER PUBLICATIONS

Buteau, Kristen C.; "Deuterated Drugs: Unexpectedly Nonobvious?", 10 J. High Tech L. 22 (2009).

Zhu, Zhaoning, et. al.; Journal of Medicinal Chemistry, vol. 53, No. 3, "Discovery of Cyclic Acylguanidines as Highly Potent and Selective . . . "; Sep. 21, 2009, pp. 951-965.

Nowak, Paweit. et. al.; Biiorganic and Medicinal Chemistry Letters; 20 (2010); "Discovery and initial optimization of 5, 5'-disubstituted aminohydantoins as potent . . . "; pp. 632-635.

Zhou, Ping, et. al.; Biiorganic and Medicinal Chemistry Letters; 20 (2010);"Pyridinyl aminohydantoins as small molecule BACE1 inhibitors"; pp. 2236-2329

Malamas, Michael S.; et. al.; Biiorganic and Medicinal Chemistry Letters; 18 (2010); "Di-substituted pyridinyl aminohydantoins as potent and highly selective human . . . "; pp. 630-639.

Zhou, Ping; et. al.; "Pyridinylaminohydantoins as small molecule BACE-1 Inhibitors: Explorations of the S3 pocket", AN 2007:883652; 234th ACS Conference Meeting Abstract; 2010 ACS on SciFinder.

Baxter, Ellen, et. al.; "BACE (Beta-Amyloid site Cleaving Enzyme, β-Secretase) Inhibitors for the treatment of Alzheimer's disease"; AN 2007:883605; 234th ACS Conference Meeting Abstract; 2010 ACS on SciFinder.

Albert, Jeffrey S.; et. al.; "Fragment based lead generation approaches for inhibitors of beta-secretase: Development of a novel series of isocytosine-based inhibitors"; AN 2007:295744, (2007).

Yan, Yinfa; et. al.; Piperidinyl-2-aminohydantoin derivatives for the inhibition of beta-secretase; AN 2007:295742; 233rd ACS National Meeting Abstract; 2010 ACS on SciFinder.

Erdel, Jim; et. al.; "Carbocylic substituted aminohydatoins as BACE-1 Inhibitors"; AN 2007: 295741; 233rd ACS National Meeting Abstract; 2010 ACS on SciFinder.

Nowak, Pawei; et. al.; "Hit-to-lead optimization of aminohydantoins as b-Secretase Inhibitors"; AN 2007:295740; 233rd ACS National Meeting Abstract; 2010 ACS on SciFinder.

Malamas, Michael S.; et. al.; "Aminohydantoins as highly potent, selective and orally active BACE 1 Inhibitors", AN 2007-295667; 233rd Conference Meeting Abstract; 2010 ACS on SciFinder.

Malamas, Michael S.; et. al.; "Thienyl aminohydantoins as potent BACE1 Inhibitors", AN 2008:953770; 236th Conference Meeting Abstract; 2010 ACS on SciFinder.

Malamas, Michael S.; et. al.; "Pyrazinyl aminohydantoins as potent BACE1 Inhibitors", AN 2008:953771; 236thConference Meeting Abstract; 2010 ACS on SciFinder.

Malamas, Michael S.; et. al.;"Pyrrolyl 2-aminopyridines as potent BACE1 Inhibitors", 238thConference Meeting Abstract; 2010 ACS on SciFinder.

Zhou, Ping; et. al.; "Substituted-pyrrole 2-amino-3,5-dihydro-4H-imidazol-4-ones as highly potent BACE1 Inhibitors: Optimization of the S3 pocket"; 235th Conference Meeting Abstract; 2010 ACS on SciFinder.

Yan, Yinfa; et. al.; "Syntheses and biological properties of carbocylic substituted aminohydantoin derivatives", AN 2008:389811; 235th Conference Meeting Abstract; 2010 ACS on SciFinder.

Quagliato, Dominick; et. al.; "Rigid analogs of 4,4-diaryl-iminohydantoins as potent inhibitors of Beta-secretase", AN 2008:389810; 235th Conference Meeting Abstract; 2010 ACS on SciFinder.

Solvibile, William R.; et. al.; "2-Substituted-pyrrole 2-amino-3,5-dihydro-4H-imidazol-4-ones: Highly potent and selective BACE1 Inhibitors", AN 2008:389809; 235th Conference Meeting Abstract; 2010 ACS on SciFinder.

Erdel, Jim; et. al.; "N-Alkyl substituted-pyrrole 2-amino-3,5-dihydro-4H-imidazol-4-ones as potent, and selective BACE 1 Inhibitors", AN 2008:389808; 235th Conference Meeting Abstract; 2010 ACS on SciFinder.

Fobare, William F. et. al.; "Substituted-pyrrole 2-amino-3,5-dihydro-4h-imidazol-4-ones as highly potent and selective BACE1 Inhibitors", AN 2008:389736; 235th Conference Meeting Abstract; 2010 ACS on SciFinder.

Fan, Kristi Yi; et. al.; "Structure-based lead optimization of small molecule β-secretase(BACE1) Inhibitors", AN 2008:387238; 235th Conference Meeting Abstract; 2010 ACS on SciFinder.

Zhu, Zhaoning, et. al.; "Discovery of cyclic-aclguanidines as potent and selective BACE1 Inhibitors", AN 2009: 984464; 238th Conference Meeting Abstract; 2010 ACS on SciFinder.

Cuming, Jared, et. al.; Optimization of the iminohydantoin series of BACE1 Inhibitors. Part 4: Explorations of the F'subsite in the C5-aryl series; AN 2009:984451; 2010 ACS on SciFinder.

Smith, Elizabeth, et. al.; "Optimization of the iminohydantoin series of BACE1 Inhibitors. Part 5: Exploration of the S1' and S2-S3 binding sites"; AN 2009;984450; 238th, Conference Meeting Abstract; 2010 ACS on SciFinder.

Mazzola, Robert, D.; et. al.; Design and synthesis of novel iminohydatoin β-secretase (BACE) Inhibitors. Part 3: Discovery and Exploration of the "A-site"; AN 2009:984449; 238th Conference Meeting Abstract; 2010 ACS on SciFinder.

Mazzola, Robert, D.; et. al.;"Novel iminopyrimidinone β-secretase (BACE)Inhibitors: Part 3: C5 Substititution"; AN 2010:345058; 239th Conference Meeting Abstract; 2010 ACS on SciFinder.

Caldwell, John, et. al.; Design and synthesis of novel iminohydatoin β-secretase (BACE) Inhibitors. Part 2: The S1 to S3 approach; AN 2009:984447; 238th Conference Meeting Abstract; 2010 ACS on SciFinder.

Sun Zhong-Yue, et. al.; "2-iminohydatoin as potential BACE1 Inhibitors"; AN 2009:984446; 238th Conference Meeting Abstract; 2010 ACS on SciFinder.

Efremov, Ivan V., et. al.; "Identificaiton of spirocycli pyrrolidines as novel BACE Inhibitors"; AN2010:345057; 239th Conference Meeting Abstract; 2010 ACS on SciFinder.

Iserloh, Ulrich; et. al.; Novel iminopyrimidinone β-secretase (BACE)Inhibitors: Part 2. P1-azoles AN 2010:345056; 239th Conference Meeting Abstract; 2010 ACS on SciFinder.

Robichaud, Albert J.; et. al.; Identification of selective BACE1 inhibitors as potential disease modifying treatments for Alzheimer's disease: AN 2010:344829; 239th Conference Meeting Abstract; 2010 ACS on SciFinder.

Brodney, Michael A.; et. al.; "Beta-secretase inhibitors for the treatment of Alzheimer's disease", AN2010:344828; 239th Conference Meeting Abstract; 2010 ACS on SciFinder.

Stamford, Andrew.W.; et. al.; "Discovery of small molecule, orally active and brain penetrant BACE 1 Inhibitors", AN 2010: 344827; 239th Conference Meeting Abstract; 2010 ACS on SciFinder.

O'Neill, Brian T.; et. al.; "Pyrrolidine ss-secretase inhibitors for the treatment of Alzheimer's disease", AN 2010: 344728; 239th Conference Meeting Abstract; 2010 ACS on SciFinder.

Cumming, Jared N.; Novel iminopyrimidinone β-secretase (BACE)Inhibitors: Part 1, P1-P3 SAR; AN 2010:344544; 239th Conference Meeting Abstract; 2010 ACS on SciFinder.

PCT Search Report for International Application No. PCT/US2009/041202 filed Apr. 21, 2009, 3 pages.

Written Opinion for International Application no. PCT/US2009/041202 filed Apr. 21, 2009, 5 pages.

PCT Search Report for International Application No. PCT/US2006/022913 filed Jun. 12, 2006; 3 pages.

Written Opinion for International Application No. PCT/US2006/022913 filed Jun. 12, 2006; 5 pages.

Keana, et. Al.; Journal of Organic Chemistry;vol. 34, No. 11; Nov. 1969; pp. 3705-3707.

Keana, et. Al.; Journal of Organic Chemistry;vol. 41, No. 12; Nov. 1976; pp. 2124-2129.

PHENYL-SUBSTITUTED 2-IMINO-3-METHYL PYRROLO PYRIMIDINONE COMPOUNDS AS BACE-1 INHIBITORS, COMPOSITIONS, AND THEIR USE

CROSS-REFERENCE TO RELATED APPLICATION

This application claims priority to provisional application U.S. Ser. No. 61/047,006, filed Apr. 22, 2008, incorporated by reference.

FIELD OF THE INVENTION

This invention provides certain novel 2-imino-3-methylpyrrolo pyrimidinone compounds and compositions comprising these compounds. The compounds and compositions of the invention are useful as BACE-1 inhibitors and for the treatment and prevention of various pathologies related to β-amyloid ("Aβ") production.

BACKGROUND

Amyloid beta peptide ("A/β") is a primary component of β amyloid fibrils and plaques, which are regarded as a causative feature in an increasing number of pathologies. Examples of such pathologies include, but are not limited to, Alzheimer's Disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ($β_2$ microglobulins and complications arising therefrom), neurodegenerative diseases such as scrapie, bovine spongiform encephalitis, and Creutzfeld-Jakob disease and the like.

Aβ peptides are short peptides which are made from the abnormal proteolytic break-down of the transmembrane protein called amyloid precursor protein ("APP"). Aβ peptides are made from the cleavage of APP by β-secretase activity at the position corresponding to the N-terminus of Aβ, and by □-secretase activity at the position corresponding to the C-terminus of Aβ. (APP is also cleaved by □-secretase activity, resulting in the secreted, non-amyloidogenic fragment known as soluble APPα.) Beta site APP Cleaving Enzyme ("BACE-1") is regarded as the primary aspartyl protease responsible for the production of abnormal Aβ by β-secretase activity. The inhibition of BACE-1 has been shown to inhibit the production of Aβ.

Alzheimer's disease ("AD") is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, abnormally formed through β-secretase and □secretase activity, can form tertiary structures that aggregate to form amyloid fibrils. Aβ peptides have also been shown to form Aβ oligomers (sometimes referred to as "Abeta aggretates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ and Aβ fibrils and plaque play a causal role in AD pathophysiology. (See Ohno et al., *Neurobiology of Disease*, No. 26 (2007), 134-145.) Mutations in the genes for APP and presenilins ½ (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuron cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., *J. Bio. Chem.*, vol. 282, No. 36 (September 2007), have shown that partial reductions of BACE-1 enzyme activity and concomitant reductions of Aβ levels lead to a dramatic inhibition of Aβ-driven AD-like pathology (while minimizing side effects of full inhibition), making β-secretase a target for therapeutic intervention in AD. Ohno et al. *Neurobiology of Disease*, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and conclude that BACE-1 inhibition has been validated as an approach for the treatment of AD. Roberds et al., *Human Mol. Genetics*, 2001, Vol. 10, No. 12, 1317-1324, established that inhibition or loss of β-secretase activity produces no profound phenotypic defects while inducing a concomitant reduction in β-amyloid peptide. Luo et al., *Nature Neuroscience*, vol. 4, no. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., *PNAS*, vol. 104, no. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., *Neurobiology of Aging*, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., *Ann NY Acad Sci* 2002; 855:723-31; Crino P B, Martin J A, Hill W D, et al., *Ann Otol Rhinol Laryngol*, 1995; 104:655-61; Davies D C, et al., *Neurobiol Aging*, 1993; 14:353-7; Devanand D P, et al., *Am J Psychiatr*, 2000; 157:1399-405; and Doty R L, et al., *Brain Res Bull*, 1987; 18:597-600. It is reasonable to suggest that addressing such changes by reduction of Aβ by inhibition of BACE-1 could help to restore olfactory sensitivity in patients with AD.

Other diverse pathologies characterized by the inappropriate formation and deposition of Aβ or fragments thereof, and/or by the presence of amyloid fibrils, include neurodegenerative diseases such as scrapie, bovine spongiform encephalitis, Creutzfeld-Jakob disease and the like, type II diabetes (which is characterized by the localized accumulation of cytotoxic amyloid fibrils in the insulin producing cells of the pancreas), and amyloid angiopathy In this regard reference can be made to the patent literature. For example, Kong et al., US2008/0015180, disclose methods and compositions for treating amyloidosis with agents that inhibit Aβ peptide formation. Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify BACE-1 and other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, and WO2007/146225.

WO2006/138264, (Zhu et al.) disclose certain aspartyl protease inhibitors, pharmaceutical compositions comprising said compounds, and their use in the treatment of cardiovascular disease, cognitive and neurodegenerative diseases, and their use as inhibitors of the Human Immunosufficiency Virus, plasmepsins, cathepsin D, and protozoal enzymes. The compounds disclosed in Zhu et al. include compounds of the formula:

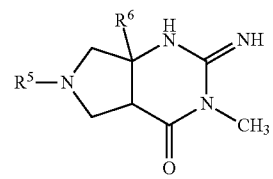

wherein $R^5$ and $R^6$ are as defined therein. All of the exemplified compounds in WO'264 contain a thiophenyl or a substituted thiophenyl group at the position corresponding to $R^6$.

SUMMARY OF THE INVENTION

In one embodiment, the present invention provides certain 2-imino-3-methyl pyrrolo pyrimidone compounds (collectively or individually referred to herein as "compound(s) of the invention"), as described herein.

In one embodiment, the compounds of the invention have the structural Formula (II):

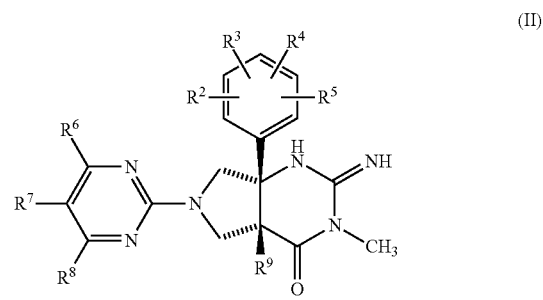

and include tautomers thereof, and pharmaceutically acceptable salts and solvates of said compounds and said tautomers, wherein $R^2$, $R^3$, $R^4$, $R^5$, $R^6$, $R^7$, $R^8$, and $R^9$ are each selected independently and wherein:

$R^2$ is selected from hydrogen, fluorine, chlorine, bromine, and cyano;

$R^3$ is selected from hydrogen, fluorine, chlorine, and cyano;

$R^4$ is selected from hydrogen, fluorine, chlorine, and cyano;

$R^5$ is selected from hydrogen, fluorine, and chlorine;

$R^6$ is selected from lower alkyl, lower alkoxy, lower haloalkyl, lower haloalkoxy, and lower alkyl-OH;

$R^7$ is selected from fluorine and chlorine;

$R^8$ is selected from; lower alkyl, lower alkoxy, lower haloalkyl, lower haloalkoxy, cycloalkyl, -alkyl-cycloalkyl, —O-cycloalkyl, and —O-alkyl-cycloalkyl; and $R^9$ is selected from hydrogen and lower alkyl.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an amyloid β pathology (Aβ pathology) and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

In one embodiment, the compounds of the invention have the structural Formula (II) as described above.

In another embodiment, the compounds of the invention have the structural Formula (II-A):

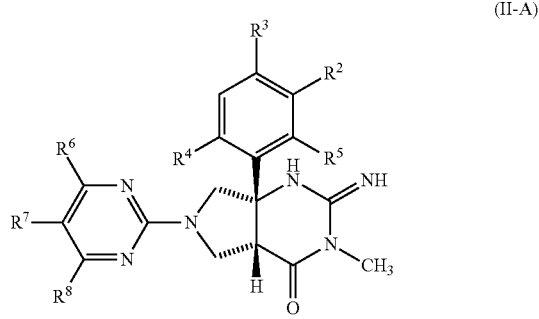

(II-A)

and include tautomers thereof, and pharmaceutically acceptable salts and solvates of said compounds and/or said tautomers, wherein $R^2$, $R^3$, $R^4$, $R^5$, $R^6$, $R^7$, and $R^8$ are each selected independently and wherein:

$R^2$ is selected from hydrogen, fluorine, chlorine, and cyano;
$R^3$ is selected from hydrogen, fluorine, chlorine, and cyano;
$R^4$ is selected from hydrogen, fluorine, chlorine, and cyano;
$R^5$ is selected from hydrogen, fluorine, and chlorine;
$R^6$ is selected from lower alkyl, lower alkoxy, lower haloalkyl, lower haloalkoxy, and lower alkyl-OH;
$R^7$ is selected from fluorine and chlorine; and
$R^8$ is selected from: lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, the present invention encompasses a stereoisomer or racemic mixture of a compound of the invention, or a tautomer thereof, or a pharmaceutically acceptable salt of said compound or said tautomer. It shall be appreciated that, while the present invention encompasses all stereoisomers and racemic mixtures of the compounds of the invention, the stereoconfiguration shown in the structural formulas and in the examples are preferred stereoisomers.

In another embodiment, the present invention encompasses deuterates of the compounds of the invention, or tautomers thereof, or a pharmaceutically acceptable salt of said deuterated compound or tautomer of the invention. Specific, non-limiting examples of deuterated compounds of the invention are as described and exemplified herein and include, deuterated compounds of Formulas $(II^d)$, $(II\text{-}AA^{d1})$, and $(II\text{-}AA^{d2})$, and the deuterated compounds of examples 44 and 45, below. Those of ordinary skill in the art will readily appreciate that, in addition to the non-limiting examples shown, other available hydrogen atoms may be deuterated in a similar manner as described hereinbelow. Such deuterated compounds are also to be considered as being among the compounds of the invention.

In another embodiment, in each of Formulas (II) and (II-A), each variable is selected independently of the others and:
$R^6$ is selected from methyl, ethyl, —CH$_2$OH, —CH$_2$CH$_2$OH, methoxy, ethoxy, difluoromethyl, trifluoromethyl, difluoroethyl, trifluoroethyl, difluoromethoxy, trifluoromethoxy, difluoroethoxy, and trifluoroethoxy;
$R^7$ is selected from fluorine and chlorine;
$R^8$ is selected from methoxy, ethoxy, methyl, ethyl, n-propyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy;
and $R^2$, $R^3$, $R^4$, and $R^5$ are each as defined in Formula (II).

In another embodiment, in each of Formulas (II) and (II-A), each variable is selected independently of the others and:
$R^6$ is selected from methyl, ethyl, methoxy, ethoxy, difluoromethoxy, and trifluoromethoxy;
$R^7$ is selected from fluorine and chlorine;
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl;
and $R^2$, $R^3$, $R^4$, and $R^5$ are each as defined in Formula (II).

In another embodiment, in each of Formulas (II) and (II-A), each variable is selected independently of the others and:
$R^6$ is selected from methoxy and ethoxy;
$R^7$ is selected from fluorine and chlorine;
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl;
and $R^2$, $R^3$, $R^4$, and $R^5$ are each as defined in Formula (II).

In another embodiment, in each of Formulas (II) and (II-A), each variable is selected independently of the others and:
$R^6$ is selected from methoxy and ethoxy;
$R^7$ is selected from fluorine and chlorine;
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy;
and $R^2$, $R^3$, $R^4$, and $R^5$ are each as defined in Formula (II).

In another embodiment, in each of Formulas (II) and (II-A), each variable is selected independently of the others and:
$R^6$ is methoxy;
$R^7$ is fluorine;
$R^8$ is selected from lower alkyl, cycloalkyl, and lower alkoxy;
and $R^2$, $R^3$, $R^4$, and $R^5$ are each as defined in Formula (II).

In another embodiment, in each of Formulas (II) and (II-A), each variable is selected independently of the others and:
$R^6$ is methoxy;
$R^7$ is fluorine;
$R^8$ is selected from methyl, ethyl, cyclopropyl, methoxy, and ethoxy;
and $R^2$, $R^3$, $R^4$, and $R^5$ are each as defined in Formula (II).

In another embodiment, in each of Formulas (II) and (II-A), each variable is selected independently of the others and:
$R^6$ is methoxy;
$R^7$ is fluorine;
$R^8$ is methyl;
and $R^2$, $R^3$, $R^4$, and $R^5$ are each as defined in Formula (II).

In another embodiment, in each of Formulas (II) and (II-A), each variable is selected independently of the others and:
R⁶ is methoxy;
R⁷ is fluorine;
R⁸ is ethyl;
and R², R³, R⁴, and R⁵ are each as defined in Formula (II).

In another embodiment, in each of Formulas (II) and (II-A), each variable is selected independently of the others and:
R⁶ is methoxy;
R⁷ is fluorine;
R⁸ is cyclopropyl;
and R², R³, R⁴, and R⁵ are each as defined in Formula (II).

In another embodiment, in each of Formulas (II) and (II-A), each variable is selected independently of the others and:
R⁶ is methoxy;
R⁷ is fluorine;
R⁸ is methoxy;
and R², R³, R⁴, and R⁵ are each as defined in Formula (II).

In another embodiment, in each of Formulas (II) and (II-A), each variable is selected independently of the others and:
R⁶ is selected from lower alkyl, lower alkoxy, lower haloalkyl, lower haloalkoxy, and lower alkyl-OH;
R⁷ is selected from fluorine and chlorine; and
R⁸ is selected from lower alkyl, lower alkoxy, and cyclopropyl.

In another embodiment, in each of Formulas (II) and (II-A), each variable is selected independently of the others and:
R⁶ is selected from methyl, ethyl, methoxy, ethoxy, —CH₂OH, —CF₃, and —CF₂CH₃;
R⁷ is selected from fluorine and chlorine; and
R⁸ is selected from methoxy, ethoxy, cyclopropyl, and ethyl.

In another embodiment, in each of Formulas (II) and (II-A), each variable is selected independently of the others and:
R⁶ is selected from methyl, ethyl, and methoxy;
R⁷ is selected from fluorine and chlorine; and
R⁸ is selected from methoxy and cyclopropyl.

In another embodiment, in each of Formulas (II) and (II-A), each variable is selected independently of the others and:
R⁶ is methyl;
R⁷ is fluorine; and
R⁸ is methoxy.

In another embodiment, in each of Formulas (II) and (II-A), each variable is selected independently of the others and:
R⁶ is methoxy;
R⁷ is fluorine; and
R⁸ is cyclopropyl.

In another embodiment, in each of Formulas (II) and (II-A), each variable is selected independently of the others and:
R⁶ is selected from methyl, ethyl, methoxy, ethoxy, —CH₂OH, —CF₃, and —CF₂CH₃;
R⁷ is selected from fluorine and chlorine; and
R⁸ is selected from methoxy, ethoxy, cyclopropyl, and ethyl;
and the moiety

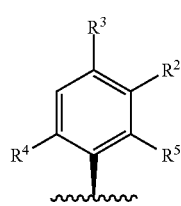

shown in Formula (II-A) is selected from:

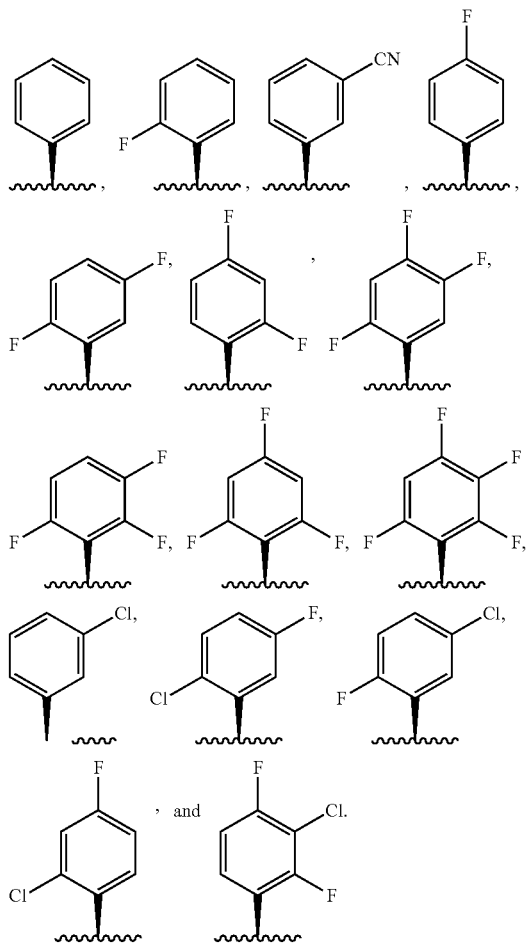

In another embodiment, in each of Formulas (II) and (II-A), each variable is selected independently of the others and:
the moiety

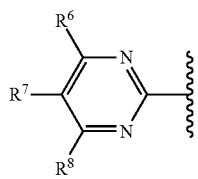

shown in Formula (II-A) is selected from the group consisting of

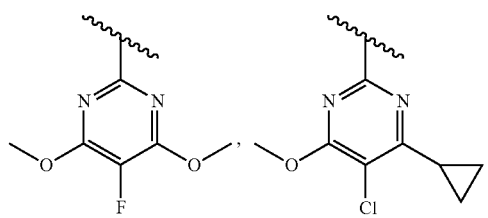

-continued

[chemical structures]

In another embodiment, the compounds of the invention have the structural Formula (II-AA):

(II-AA)

[chemical structure]

and include tautomers thereof, and pharmaceutically acceptable salts of said compounds and said tautomers, wherein:

$R^2$ is selected from hydrogen, fluorine, chlorine, and cyano;

$R^3$ is selected from hydrogen, fluorine, chlorine, and cyano;

$R^4$ is selected from hydrogen, fluorine, chlorine, and cyano; and $R^5$ is selected from hydrogen, fluorine, and chlorine.

As noted above, one or more available hydrogen atoms in the compounds of the invention may be replaced by deuterium. The resulting compound is referred to herein as a "deuterated" compound of the invention or, alternatively, as "deuterate(s)" of compounds of the invention. The compounds of the invention may be deuterated in a manner known to those of ordinary skill in the art, e.g., as described below.

Thus, in one embodiment, deuterated compounds of the invention have the structural Formula ($II^d$):

($II^d$)

[chemical structure]

and include tautomers thereof, and pharmaceutically acceptable salts and solvates of said deuterated compounds and said tautomers, wherein $R^2$, $R^3$, $R^4$, $R^5$, $R^6$, $R^7$, $R^8$, and $R^9$ are each selected independently and wherein:

the moiety —$CD_3$ represents a deuterated form of the moiety —$CH_3$;

$R^2$ is selected from hydrogen, fluorine, chlorine, bromine, and cyano;

$R^3$ is selected from hydrogen, fluorine, chlorine, and cyano;

$R^4$ is selected from hydrogen, fluorine, chlorine, and cyano;

$R^5$ is selected from hydrogen, fluorine, and chlorine;

$R^6$ is selected from lower alkyl, lower alkoxy, lower haloalkyl, lower haloalkoxy, and lower alkyl-OH;

$R^7$ is selected from fluorine and chlorine;

$R^8$ is selected from; lower alkyl, lower alkoxy, lower haloalkyl, lower haloalkoxy, cycloalkyl, -alkyl-cycloalkyl, —O-cycloalkyl, and —O-alkyl-cycloalkyl; and $R^9$ is selected from hydrogen and lower alkyl.

In another embodiment, in Formula ($II^d$), one or more additional available hydrogen atoms in $R^2$, $R^3$, $R^4$, $R^5$, $R^6$, $R^7$, $R^8$, and $R^9$ may be exchanged for deuterium. Deuterated versions of all of the embodiments of the compounds of the invention described herein are contemplated as being within the scope of the invention.

In another embodiment, the compounds of the invention are deuterated and have the structural Formula (II-AA$^{d1}$):

(II-AA$^{d1}$)

[chemical structure]

and include tautomers thereof, and pharmaceutically acceptable salts of said compounds and said tautomers, wherein:

the moiety —$CD_3$ represents a deuterated form of the moiety —$CH_3$;

$R^2$ is selected from hydrogen, fluorine, chlorine, and cyano;

$R^3$ is selected from hydrogen, fluorine, chlorine, and cyano;

$R^4$ is selected from hydrogen, fluorine, chlorine, and cyano; and $R^5$ is selected from hydrogen, fluorine, and chlorine.

In another embodiment, the compounds of the invention are deuterated and have the structural Formula (II-AA$^{d2}$):

(II-AA$^{d2}$)

[chemical structure]

and include tautomers thereof, and pharmaceutically acceptable salts of said compounds and said tautomers, wherein:

the moiety —$CD_3$ represents a deuterated form of the moiety —$CH_3$;

the moiety —OCD₃ represents a deuterated form of the moiety —OCH₃;
R² is selected from hydrogen, fluorine, chlorine, and cyano;
R³ is selected from hydrogen, fluorine, chlorine, and cyano;
R⁴ is selected from hydrogen, fluorine, chlorine, and cyano; and
R⁵ is selected from hydrogen, fluorine, and chlorine.

In another embodiment, in each of Formulas (II$^d$), (II-AA), (II-AA$^{d1}$), and (II-AA$^{d2}$):
the moiety

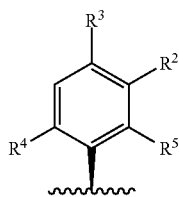

shown in Formula (II-AA) is selected from:

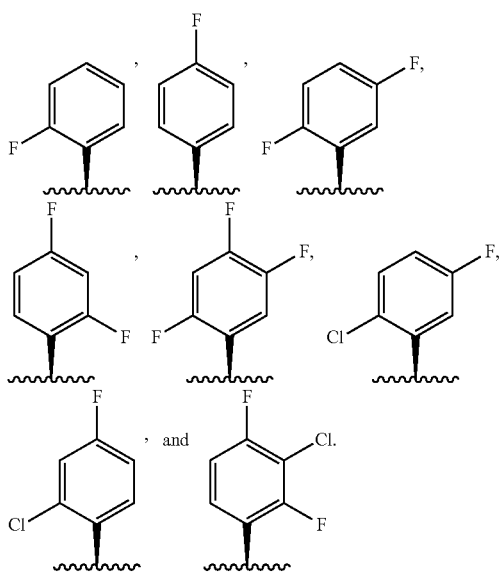

In another embodiment, the compounds of the invention have the structural Formula (II-AB):

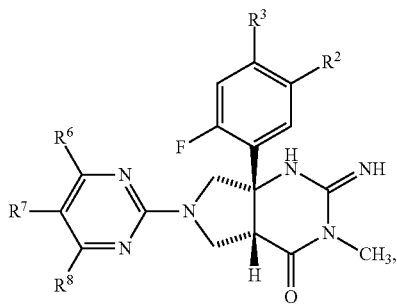

(II-AB)

and include tautomers thereof, and pharmaceutically acceptable salts of said compounds and said tautomers, wherein:
wherein each variable is selected independently of the others and wherein:
the moiety

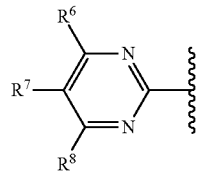

shown in (II-AB) is selected from the group consisting of

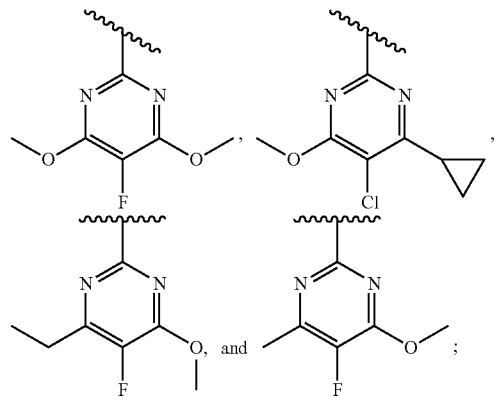

either R² is F and R³ is H or R² is H and R³ is F.

In another embodiment, the compounds of the invention have the structural Formula (II-A1):

(II-A1)

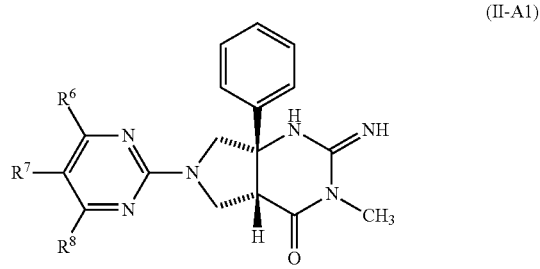

and include tautomers, or pharmaceutically acceptable salts or solvates of said compounds or said tautomers, wherein each of R⁶, R⁷, and R⁸ is selected independently and as defined in Formula (II).

In another embodiment, in Formula (II-A1), each variable is selected independently of the others and:
R⁶ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
R⁷ is selected from fluorine and chlorine; and
R⁸ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A1), each variable is selected independently of the others and:
R⁶ is selected from methyl, ethyl, methoxy, ethoxy, difluoromethoxy, and trifluoromethoxy;
R⁷ is selected from fluorine and chlorine; and
R⁸ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A1), each variable is selected independently of the others and:
R⁶ is selected from methoxy and ethoxy;
R⁷ is selected from fluorine and chlorine; and
R⁸ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A1), each variable is selected independently of the others and:
R⁶ is selected from methoxy and ethoxy;
R⁷ is selected from fluorine and chlorine; and
R⁸ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A1), each variable is selected independently of the others and:
R⁶ is selected from lower alkyl, lower alkoxy, lower haloalkyl, lower haloalkoxy, and lower alkyl-OH;
R⁷ is selected from fluorine and chlorine; and
R⁸ is selected from lower alkyl, lower alkoxy, and cyclopropyl.

In another embodiment, in Formula (II-A1), each variable is selected independently of the others and:
R⁶ is selected from methyl, ethyl, methoxy, ethoxy, —CH₂OH, —CF₃, and —CF₂CH₃;
R⁷ is selected from fluorine and chlorine; and
R⁸ is selected from methoxy, ethoxy, cyclopropyl, and ethyl.

In another embodiment, in Formula (II-A1), each variable is selected independently of the others and:
R⁶ is methoxy;
R⁷ is fluorine; and
R⁸ is selected from lower alkyl, cycloalkyl, and lower alkoxy.

In another embodiment, in Formula (II-A1):
R⁶ is methoxy;
R⁷ is fluorine; and
R⁸ is selected from methyl, ethyl, cyclopropyl, methoxy, and ethoxy.

In another embodiment, in Formula (II-A1):
R⁶ is methoxy;
R⁷ is fluorine; and
R⁸ is methyl.

In another embodiment, in Formula (II-A1):
R⁶ is methoxy;
R⁷ is fluorine; and
R⁸ is ethyl.

In another embodiment, in Formula (II-A1):
R⁶ is methoxy;
R⁷ is fluorine; and
R⁸ is cyclopropyl.

In another embodiment, in Formula (II-A1):
R⁶ is methoxy;
R⁷ is fluorine; and
R⁸ is methoxy.

In another embodiment, the compounds of the invention have the structural Formula (II-A2):

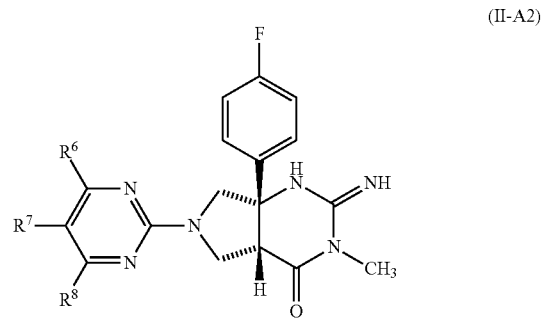

(II-A2)

and include tautomers and pharmaceutically acceptable salts and/or solvates of said compounds and/or said tautomers, wherein each of R⁶, R⁷, and R⁸ is selected independently and as defined in Formula (II).

In another embodiment, in Formula (II-A2), each variable is selected independently of the others and:
R⁶ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
R⁷ is selected from fluorine and chlorine; and
R⁸ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A2), each variable is selected independently of the others and:
R⁶ is selected from methyl, ethyl, methoxy, ethoxy, difluoromethoxy, and trifluoromethoxy;
R⁷ is selected from fluorine and chlorine; and
R⁸ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A2), each variable is selected independently of the others and:
R⁶ is selected from methoxy and ethoxy;
R⁷ is selected from fluorine and chlorine; and
R⁸ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A2), each variable is selected independently of the others and:
R⁶ is selected from methoxy and ethoxy;
R⁷ is selected from fluorine and chlorine; and
R⁸ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A2), each variable is selected independently of the others and:
R⁶ is selected from lower alkyl, lower alkoxy, lower haloalkyl, lower haloalkoxy, and lower alkyl-OH;
R⁷ is selected from fluorine and chlorine; and
R⁸ is selected from lower alkyl, lower alkoxy, and cyclopropyl.

In another embodiment, in Formula (II-A2), each variable is selected independently of the others and:
R⁶ is selected from methyl, ethyl, methoxy, ethoxy, —CH₂OH, —CF₃, and —CF₂CH₃;

$R^7$ is selected from fluorine and chlorine; and
$R^8$ is selected from methoxy, ethoxy, cyclopropyl, and ethyl.

In another embodiment, in Formula (II-A2):
$R^6$ is methoxy;
$R^7$ is fluorine; and
$R^8$ is selected from lower alkyl, cycloalkyl, and lower alkoxy.

In another embodiment, in Formula (II-A2):
$R^6$ is methoxy;
$R^7$ is fluorine; and
$R^8$ is selected from methyl, ethyl, cyclopropyl, methoxy, and ethoxy.

In another embodiment, in Formula (II-A2):
$R^6$ is methoxy;
$R^7$ is fluorine; and
$R^8$ is methyl.

In another embodiment, in Formula (II-A2):
$R^6$ is methoxy;
$R^7$ is fluorine; and
$R^8$ is ethyl.

In another embodiment, in Formula (II-A2):
$R^6$ is methoxy;
$R^7$ is fluorine; and
$R^8$ is cyclopropyl.

In another embodiment, in Formula (II-A2):
$R^6$ is methoxy;
$R^7$ is fluorine; and
$R^8$ is methoxy.

In another embodiment, the compounds of the invention have the structural Formula (II-A3):

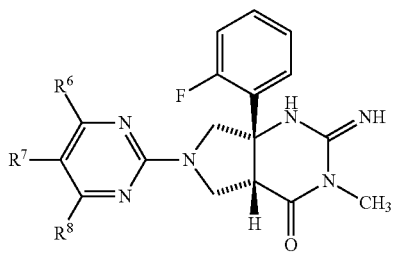

(II-A3)

and include tautomers and pharmaceutically acceptable salts and/or solvates of said compounds and/or said tautomers, wherein each of $R^6$, $R^7$, and $R^8$ is selected independently and as defined in Formula (II).

In another embodiment, in Formula (II-A3), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A3), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A3), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A3), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A3), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A3), each variable is selected independently of the others and:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl.

In another embodiment, in Formula (II-A3):
$R^6$ is methoxy;
$R^7$ is fluorine; and
$R^8$ is selected from lower alkyl, cycloalkyl, and lower alkoxy.

In another embodiment, in Formula (II-A3):
$R^6$ is methoxy;
$R^7$ is fluorine; and
$R^8$ is selected from methyl, ethyl, cyclopropyl, methoxy, and ethoxy.

In another embodiment, in Formula (II-A3):
$R^6$ is methoxy;
$R^7$ is fluorine; and
$R^8$ is methyl.

In another embodiment, in Formula (II-A3):
$R^6$ is methoxy;
$R^7$ is fluorine; and
$R^8$ is ethyl.

In another embodiment, in Formula (II-A3):
$R^6$ is methoxy;
$R^7$ is fluorine; and
$R^8$ is cyclopropyl.

In another embodiment, in Formula (II-A3):
$R^6$ is methoxy;
$R^7$ is fluorine; and
$R^8$ is methoxy.

In another embodiment, the compounds of the invention have the structural Formula (II-A4):

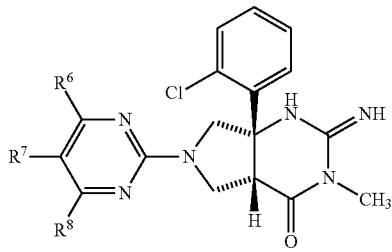

(II-A4)

and include tautomers and pharmaceutically acceptable salts and/or solvates of said compounds and/or said tautomers, wherein each of $R^6$, $R^7$, and $R^8$ is selected independently and as defined in Formula (II).

In another embodiment, in Formula (II-A4), each variable is selected independently of the others and:

$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A4), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A4), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A4), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A4), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A4), each variable is selected independently of the others and:

$R^6$ is selected from methyl, ethyl, methoxy, ethoxy, —CH$_2$OH, —CF$_3$, and —CF$_2$CH$_3$;

$R^7$ is selected from fluorine and chlorine; and $R^8$ is selected from methoxy, ethoxy, cyclopropyl, and ethyl.

In another embodiment, in Formula (II-A4):

$R^6$ is methoxy;

$R^7$ is fluorine; and $R^8$ is selected from lower alkyl, cycloalkyl, and lower alkoxy.

In another embodiment, in Formula (II-A4):

$R^6$ is methoxy;

$R^7$ is fluorine; and $R^8$ is selected from methyl, ethyl, cyclopropyl, methoxy, and ethoxy.

In another embodiment, in Formula (II-A4):

$R^6$ is methoxy;

$R^7$ is fluorine; and $R^8$ is methyl.

In another embodiment, in Formula (II-A4):

$R^6$ is methoxy;

$R^7$ is fluorine; and $R^8$ is ethyl.

In another embodiment, in Formula (II-A4):

$R^6$ is methoxy;

$R^7$ is fluorine; and $R^8$ is cyclopropyl.

In another embodiment, in Formula (II-A4):

$R^6$ is methoxy;

$R^7$ is fluorine; and $R^8$ is methoxy.

In another embodiment, the compounds of the invention have the structural Formula (II-A5):

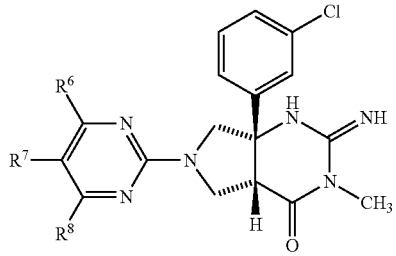

(II-A5)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A5), each variable is selected independently of the others and:

$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A5), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A5), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A5), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A5), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A5), each variable is selected independently of the others and:

$R^6$ is selected from methyl, ethyl, methoxy, ethoxy, —CH$_2$OH, —CF$_3$, and —CF$_2$CH$_3$;

$R^7$ is selected from fluorine and chlorine; and $R^8$ is selected from methoxy, ethoxy, cyclopropyl, and ethyl.

In another embodiment, in Formula (II-A5):

$R^6$ is methoxy;

$R^7$ is fluorine; and $R^8$ is selected from lower alkyl, cycloalkyl, and lower alkoxy.

In another embodiment, in Formula (II-A5):

$R^6$ is methoxy;

$R^7$ is fluorine; and $R^8$ is selected from methyl, ethyl, cyclopropyl, methoxy, and ethoxy.

In another embodiment, in Formula (II-A5):

$R^6$ is methoxy;

$R^7$ is fluorine; and $R^8$ is methyl.

In another embodiment, in Formula (II-A5):

$R^6$ is methoxy;

$R^7$ is fluorine; and $R^8$ is ethyl.

In another embodiment, in Formula (II-A5):

$R^6$ is methoxy;

$R^7$ is fluorine; and $R^8$ is cyclopropyl.

In another embodiment, in Formula (II-A5):

$R^6$ is methoxy;

$R^7$ is fluorine; and $R^8$ is methoxy.

In another embodiment, the compounds of the invention have the structural Formula (II-A6):

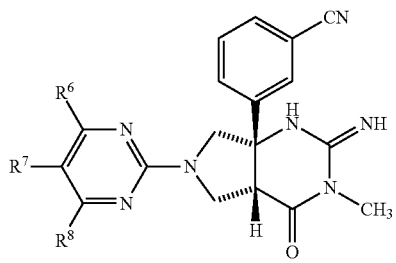

(II-A6)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A6), each variable is selected independently of the others and:

$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A6), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A6), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A6), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A6), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A6), each variable is selected independently of the others and:

$R^6$ is selected from methyl, ethyl, methoxy, ethoxy, —CH$_2$OH, —CF$_3$, and —CF$_2$CH$_3$;

$R^7$ is selected from fluorine and chlorine; and $R^8$ is selected from methoxy, ethoxy, cyclopropyl, and ethyl.

In another embodiment, in Formula (II-A6):
R$^6$ is methoxy;
R$^7$ is fluorine; and
R$^8$ is selected from lower alkyl, cycloalkyl, and lower alkoxy.

In another embodiment, in Formula (II-A6):
R$^6$ is methoxy;
R$^7$ is fluorine; and
R$^8$ is selected from methyl, ethyl, cyclopropyl, methoxy, and ethoxy.

In another embodiment, in Formula (II-A6):
R$^6$ is methoxy;
R$^7$ is fluorine; and
R$^8$ is methyl.

In another embodiment, in Formula (II-A6):
R$^6$ is methoxy;
R$^7$ is fluorine; and
R$^8$ is ethyl.

In another embodiment, in Formula (II-A6):
R$^6$ is methoxy;
R$^7$ is fluorine; and
R$^8$ is cyclopropyl.

In another embodiment, in Formula (II-A6):
R$^6$ is methoxy;
R$^7$ is fluorine; and
R$^8$ is methoxy.

In another embodiment, the compounds of the invention have the structural Formula (II-A7):

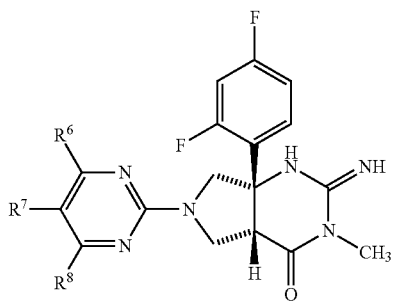

(II-A7)

and include tautomers and/or pharmaceutically acceptable salts or solvates of said compounds and/or said tautomers, wherein each of R$^6$, R$^7$, and R$^8$ is selected independently and as defined in Formula (II).

In another embodiment, in Formula (II-A7), each variable is selected independently of the others and:
R$^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
R$^7$ is selected from fluorine and chlorine; and
R$^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A7), each variable is selected independently of the others and:
R$^6$ is selected from methyl, ethyl, methoxy, ethoxy, difluoromethoxy, and trifluoromethoxy;
R$^7$ is selected from fluorine and chlorine; and
R$^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A7), each variable is selected independently of the others and:
R$^6$ is selected from methoxy and ethoxy;
R$^7$ is selected from fluorine and chlorine; and
R$^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A7), each variable is selected independently of the others and:
R$^6$ is selected from methoxy and ethoxy;
R$^7$ is selected from fluorine and chlorine; and
R$^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A7), each variable is selected independently of the others and:
R$^6$ is selected from lower alkyl, lower alkoxy, lower haloalkyl, lower haloalkoxy, and lower alkyl-OH;
R$^7$ is selected from fluorine and chlorine; and
R$^8$ is selected from lower alkyl, lower alkoxy, and cyclopropyl.

In another embodiment, in Formula (II-A7), each variable is selected independently of the others and:
R$^6$ is selected from methyl, ethyl, methoxy, ethoxy, —CH$_2$OH, —CF$_3$, and —CF$_2$CH$_3$;
R$^7$ is selected from fluorine and chlorine; and
R$^8$ is selected from methoxy, ethoxy, cyclopropyl, and ethyl.

In another embodiment, in Formula (II-A7), each variable is selected independently of the others and:
R$^6$ is selected from methyl, ethyl, and methoxy;
R$^7$ is selected from fluorine and chlorine; and
R$^8$ is selected from methoxy and cyclopropyl.

In another embodiment, in Formula (II-A7):
R$^6$ is methoxy;
R$^7$ is fluorine; and
R$^8$ is selected from lower alkyl, cycloalkyl, and lower alkoxy.

In another embodiment, in Formula (II-A7):
R$^6$ is methoxy;
R$^7$ is fluorine; and
R$^8$ is selected from methyl, ethyl, cyclopropyl, methoxy, and ethoxy.

In another embodiment, in Formula (II-A7):
R$^6$ is methoxy;
R$^7$ is fluorine; and
R$^8$ is methyl.

In another embodiment, in Formula (II-A7):
R$^6$ is methoxy;
R$^7$ is fluorine; and
R$^8$ is ethyl.

In another embodiment, in Formula (II-A7):
R$^6$ is methoxy;
R$^7$ is fluorine; and
R$^8$ is cyclopropyl.

In another embodiment, in Formula (II-A7):
R$^6$ is methoxy;
R$^7$ is fluorine; and
R$^8$ is methoxy.

In another embodiment, the compounds of the invention have the structural Formula (II-A8):

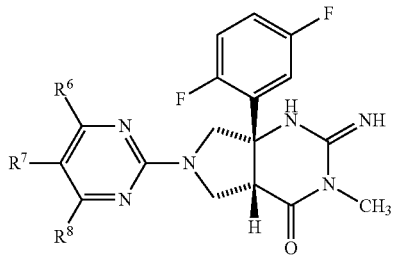

(II-A8)

and include tautomers and/or pharmaceutically acceptable salts or solvates of said compounds and/or said tautomers, wherein each of $R^6$, $R^7$, and $R^8$ is selected independently and as defined in Formula (II).

In another embodiment, in Formula (II-A8), each variable is selected independently of the others and:
$R^6$ is selected from methyl, ethyl, and methoxy;
$R^7$ is selected from fluorine and chlorine; and
$R^8$ is selected from methoxy and cyclopropyl.

In another embodiment, in Formula (II-A8), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A8), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A8), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A8), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A8), each variable is selected independently of the others and:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl.

In another embodiment, in Formula (II-A8), each variable is selected independently of the others and:
$R^6$ is selected from methyl, ethyl, and methoxy;
$R^7$ is selected from fluorine and chlorine; and
$R^8$ is selected from methoxy and cyclopropyl.

In another embodiment, in Formula (II-A8), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A8):
$R^6$ is methoxy;
$R^7$ is fluorine; and
$R^8$ is selected from lower alkyl, cycloalkyl, and lower alkoxy.

In another embodiment, in Formula (II-A8):
$R^6$ is methoxy;
$R^7$ is fluorine; and
$R^8$ is selected from methyl, ethyl, cyclopropyl, methoxy, and ethoxy.

In another embodiment, in Formula (II-A8):
$R^6$ is methoxy;
$R^7$ is fluorine; and
$R^8$ is methyl.

In another embodiment, in Formula (II-A8):
$R^6$ is methoxy;
$R^7$ is fluorine; and
$R^8$ is ethyl.

In another embodiment, in Formula (II-A8):
$R^6$ is methoxy;
$R^7$ is fluorine; and
$R^8$ is cyclopropyl.

In another embodiment, in Formula (II-A8):
$R^6$ is methoxy;
$R^7$ is fluorine; and
$R^8$ is methoxy.

In another embodiment, the compounds of the invention have the structural Formula (II-A9):

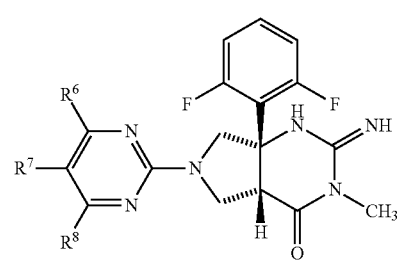

(II-A9)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A9), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A9), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A9), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A9), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A9), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A9), each variable is selected independently of the others and:

$R^6$ is selected from methyl, ethyl, methoxy, ethoxy, —$CH_2OH$, —$CF_3$, and —$CF_2CH_3$;

$R^7$ is selected from fluorine and chlorine; and $R^8$ is selected from methoxy, ethoxy, cyclopropyl, and ethyl.

In another embodiment, in Formula (II-A9):

$R^6$ is methoxy;

$R^7$ is fluorine; and $R^8$ is selected from lower alkyl, cycloalkyl, and lower alkoxy.

In another embodiment, in Formula (II-A9):

$R^6$ is methoxy;

$R^7$ is fluorine; and $R^8$ is selected from methyl, ethyl, cyclopropyl, methoxy, and ethoxy.

In another embodiment, in Formula (II-A9):

$R^6$ is methoxy;

$R^7$ is fluorine; and $R^8$ is methyl.

In another embodiment, in Formula (II-A9):

$R^6$ is methoxy;

$R^7$ is fluorine; and $R^8$ is ethyl.

In another embodiment, in Formula (II-A9):

$R^6$ is methoxy;

$R^7$ is fluorine; and $R^8$ is cyclopropyl.

In another embodiment, in Formula (II-A9):

$R^6$ is methoxy;

$R^7$ is fluorine; and $R^8$ is methoxy.

In another embodiment, the compounds of the invention have the structural Formula (II-A10):

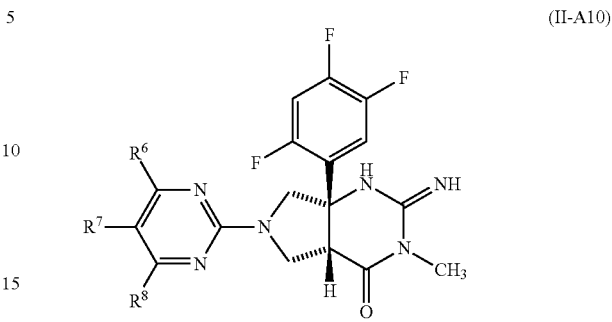

(II-A10)

and include tautomers and/or pharmaceutically acceptable salts or solvates of said compounds and/or said tautomers, wherein each of $R^6$, $R^7$, and $R^8$ is selected independently and as defined in Formula (II).

In another embodiment, in Formula (II-A10), each variable is selected independently of the others and:

$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A10), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A10), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A10), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A10), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A10), each variable is selected independently of the others and:

$R^6$ is selected from methyl, ethyl, methoxy, ethoxy, —$CH_2OH$, —$CF_3$, and —$CF_2CH_3$;

$R^7$ is selected from fluorine and chlorine; and $R^8$ is selected from methoxy, ethoxy, cyclopropyl, and ethyl.

In another embodiment, in Formula (II-A10):
$R^6$ is methoxy;
$R^7$ is fluorine; and
$R^8$ is selected from lower alkyl, cycloalkyl, and lower alkoxy.

In another embodiment, in Formula (II-A10):
$R^6$ is methoxy;
$R^7$ is fluorine; and
$R^8$ is selected from methyl, ethyl, cyclopropyl, methoxy, and ethoxy.

In another embodiment, in Formula (II-A10):
$R^6$ is methoxy;
$R^7$ is fluorine; and
$R^8$ is methyl.

In another embodiment, in Formula (II-A10):
$R^6$ is methoxy;
$R^7$ is fluorine; and
$R^8$ is ethyl.

In another embodiment, in Formula (II-A10):
$R^6$ is methoxy;
$R^7$ is fluorine; and
$R^8$ is cyclopropyl.

In another embodiment, in Formula (II-A10):
$R^6$ is methoxy;
$R^7$ is fluorine; and
$R^8$ is methoxy.

In another embodiment, the compounds of the invention have the structural Formula (II-A11):

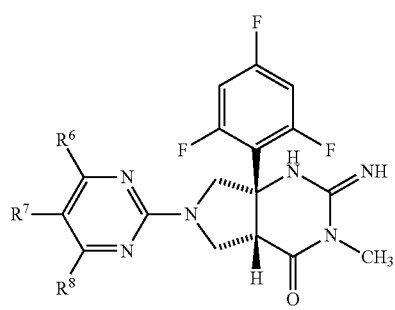

(II-A11)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A11), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A11), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A11), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A11), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A11), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A11), each variable is selected independently of the others and:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl.

In another embodiment, in Formula (II-A11):
$R^6$ is methoxy;
$R^7$ is fluorine; and
$R^8$ is selected from lower alkyl, cycloalkyl, and lower alkoxy.

In another embodiment, in Formula (II-A11):
$R^6$ is methoxy;
$R^7$ is fluorine; and
$R^8$ is selected from methyl, ethyl, cyclopropyl, methoxy, and ethoxy.

In another embodiment, in Formula (II-A11):
$R^6$ is methoxy;
$R^7$ is fluorine; and
$R^8$ is methyl.

In another embodiment, in Formula (II-A11):
$R^6$ is methoxy;
$R^7$ is fluorine; and
$R^8$ is ethyl.

In another embodiment, in Formula (II-A11):
$R^6$ is methoxy;
$R^7$ is fluorine; and
$R^8$ is cyclopropyl.

In another embodiment, in Formula (II-A11):
$R^6$ is methoxy;
$R^7$ is fluorine; and
$R^8$ is methoxy.

In another embodiment, the compounds of the invention have the structural Formula (II-A12):

(II-A12)

and include tautomers and/or pharmaceutically acceptable salts or solvates of said compounds and/or said tautomers, wherein each of $R^6$, $R^7$, and $R^8$ is selected independently and as defined in Formula (II).

In another embodiment, in Formula (II-A12), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A12), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A12), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A12), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A12), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A12), each variable is selected independently of the others and:
$R^6$ is selected from methyl, ethyl, methoxy, ethoxy, —CH$_2$OH, —CF$_3$, and —CF$_2$CH$_3$;

$R^7$ is selected from fluorine and chlorine; and
$R^8$ is selected from methoxy, ethoxy, cyclopropyl, and ethyl.

In another embodiment, in Formula (II-A12):
$R^6$ is methoxy;
$R^7$ is fluorine; and
$R^8$ is selected from lower alkyl, cycloalkyl, and lower alkoxy.

In another embodiment, in Formula (II-A12):
$R^6$ is methoxy;
$R^7$ is fluorine; and
$R^8$ is selected from methyl, ethyl, cyclopropyl, methoxy, and ethoxy.

In another embodiment, in Formula (II-A12):
$R^6$ is methoxy;
$R^7$ is fluorine; and
$R^8$ is methyl.

In another embodiment, in Formula (II-A12):
$R^6$ is methoxy;
$R^7$ is fluorine; and
$R^8$ is ethyl.

In another embodiment, in Formula (II-A12):
$R^6$ is methoxy;
$R^7$ is fluorine; and
$R^8$ is cyclopropyl.

In another embodiment, in Formula (II-A12):
$R^6$ is methoxy;
$R^7$ is fluorine; and
$R^8$ is methoxy.

In another embodiment, the compounds of the invention have the structural Formula (II-A13):

(II-A13)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A13), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A13), each variable is selected independently of the others and:
$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A13), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A13), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A13), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A13), each variable is selected independently of the others and:

$R^6$ is selected from methyl, ethyl, methoxy, ethoxy, —CH$_2$OH, —CF$_3$, and —CF$_2$CH$_3$;

$R^7$ is selected from fluorine and chlorine; and $R^8$ is selected from methoxy, ethoxy, cyclopropyl, and ethyl.

In another embodiment, in Formula (II-A13):

$R^6$ is methoxy;

$R^7$ is fluorine; and $R^8$ is selected from lower alkyl, cycloalkyl, and lower alkoxy.

In another embodiment, in Formula (II-A13):

$R^6$ is methoxy;

$R^7$ is fluorine; and $R^8$ is selected from methyl, ethyl, cyclopropyl, methoxy, and ethoxy.

In another embodiment, in Formula (II-A13):

$R^6$ is methoxy;

$R^7$ is fluorine; and $R^8$ is methyl.

In another embodiment, in Formula (II-A13):

$R^6$ is methoxy;

$R^7$ is fluorine; and $R^8$ is ethyl.

In another embodiment, in Formula (II-A13):

$R^6$ is methoxy;

$R^7$ is fluorine; and $R^8$ is cyclopropyl.

In another embodiment, in Formula (II-A13):

$R^6$ is methoxy;

$R^7$ is fluorine; and $R^8$ is methoxy.

In another embodiment, the compounds of the invention have the structural Formula (II-A14):

(II-A14)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A14), each variable is selected independently of the others and:

$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;

$R^7$ is selected from fluorine and chlorine; and $R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A14), each variable is selected independently of the others and:

$R^6$ is selected from methyl, ethyl, methoxy, ethoxy, difluoromethoxy, and trifluoromethoxy;

$R^7$ is selected from fluorine and chlorine; and $R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A14), each variable is selected independently of the others and:

$R^6$ is selected from methoxy and ethoxy;

$R^7$ is selected from fluorine and chlorine; and $R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A14), each variable is selected independently of the others and:

$R^6$ is selected from methoxy and ethoxy;

$R^7$ is selected from fluorine and chlorine; and $R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A14), each variable is selected independently of the others and:

$R^6$ is selected from lower alkyl, lower alkoxy, lower haloalkyl, lower haloalkoxy, and lower alkyl-OH;

$R^7$ is selected from fluorine and chlorine; and $R^8$ is selected from lower alkyl, lower alkoxy, and cyclopropyl.

In another embodiment, in Formula (II-A14), each variable is selected independently of the others and:

$R^6$ is selected from methyl, ethyl, methoxy, ethoxy, —CH$_2$OH, —CF$_3$, and —CF$_2$CH$_3$;

$R^7$ is selected from fluorine and chlorine; and
$R^8$ is selected from methoxy, ethoxy, cyclopropyl, and ethyl.

In another embodiment, in Formula (II-A14):
$R^6$ is methoxy;
$R^7$ is fluorine; and
$R^8$ is selected from lower alkyl, cycloalkyl, and lower alkoxy.

In another embodiment, in Formula (II-A14):
$R^6$ is methoxy;
$R^7$ is fluorine; and
$R^8$ is selected from methyl, ethyl, cyclopropyl, methoxy, and ethoxy.

In another embodiment, in Formula (II-A14):
$R^6$ is methoxy;
$R^7$ is fluorine; and
$R^8$ is methyl.

In another embodiment, in Formula (II-A14):
$R^6$ is methoxy;
$R^7$ is fluorine; and
$R^8$ is ethyl.

In another embodiment, in Formula (II-A14):
$R^6$ is methoxy;
$R^7$ is fluorine; and
$R^8$ is cyclopropyl.

In another embodiment, in Formula (II-A14):
$R^6$ is methoxy;
$R^7$ is fluorine; and
$R^8$ is methoxy.

In another embodiment, the compounds of the invention have the structural Formula (II-A15):

(II-A15)

and include tautomers and/or pharmaceutically acceptable salts or solvates of said compounds and/or said tautomers, wherein each of $R^6$, $R^7$, and $R^8$ is selected independently and as defined in Formula (II).

In another embodiment, in Formula (II-A15), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A15), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A15), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A15), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A15), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A15), each variable is selected independently of the others and:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl.

In another embodiment, in Formula (II-A15):
$R^6$ is methoxy;
$R^7$ is fluorine; and
$R^8$ is selected from lower alkyl, cycloalkyl, and lower alkoxy.

In another embodiment, in Formula (II-A15):
$R^6$ is methoxy;
$R^7$ is fluorine; and
$R^8$ is selected from methyl, ethyl, cyclopropyl, methoxy, and ethoxy.

In another embodiment, in Formula (II-A15):
$R^6$ is methoxy;
$R^7$ is fluorine; and
$R^8$ is methyl.

In another embodiment, in Formula (II-A15):
$R^6$ is methoxy;
$R^7$ is fluorine; and
$R^8$ is ethyl.

In another embodiment, in Formula (II-A15):
$R^6$ is methoxy;
$R^7$ is fluorine; and
$R^8$ is cyclopropyl.

In another embodiment, in Formula (II-A15):
$R^6$ is methoxy;
$R^7$ is fluorine; and
$R^8$ is methoxy.

In another embodiment, the compounds of the invention have the structural Formula (II-A16):

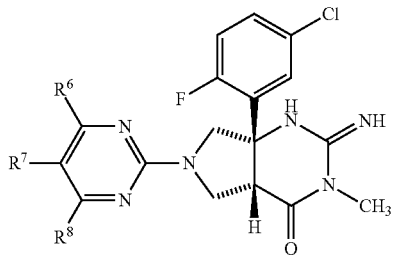

(II-A16)

and include tautomers and/or pharmaceutically acceptable salts and/or solvates of said compounds and/or said tautomers, wherein each of $R^6$, $R^7$, and $R^8$ is selected independently and as defined in Formula (II).

In another embodiment, in Formula (II-A16), each variable is selected independently of the others and:
$R^6$ is selected from methyl, ethyl, methoxy, ethoxy, difluoromethyl, trifluoroethyl, difluoroethyl, trifluoroethyl, difluoromethoxy, trifluoromethoxy, difluoroethoxy, and trifluoroethoxy;
$R^7$ is selected from fluorine and chlorine; and
$R^8$ is selected from methoxy, ethoxy, methyl, ethyl, isopropyl, cyclopropyl, cyclobutyl, difluoromethyl, trifluoromethyl, difluoroethyl, trifluoroethyl, difluoromethoxy, trifluoromethoxy, difluoroethoxy, and trifluoroethoxy.

In another embodiment, in Formula (II-A16), each variable is selected independently of the others and:
$R^6$ is selected from methyl, ethyl, methoxy, ethoxy, difluoromethoxy, and trifluoromethoxy;
$R^7$ is selected from fluorine and chlorine; and
$R^8$ is selected from methoxy, ethoxy, methyl, ethyl, isopropyl, cyclopropyl, cyclobutyl, difluoromethyl, 1,1-difluoroethyl, and 2,2,2-trifluoroethyl.

In another embodiment, in Formula (II-A16), each variable is selected independently of the others and:
$R^6$ is selected from methoxy and ethoxy;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

In another embodiment, in Formula (II-A16), each variable is selected independently of the others and:
$R^6$ is selected from methoxy and ethoxy;
$R^7$ is selected from fluorine and chlorine; and
$R^8$ is selected from methyl, ethyl, isopropyl, methoxy, ethoxy, trifluoromethyl, 1,1-difluoroethyl, 2,2,2-trifluoroethyl, trifluoromethoxy, 1,1-difluoroethoxy, and 2,2,2-trifluoroethoxy.

In another embodiment, in Formula (II-A16), each variable is selected independently of the others and:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

In another embodiment, in Formula (II-A16), each variable is selected independently of the others and:
$R^6$ is selected from methyl, ethyl, methoxy, ethoxy, —$CH_2OH$, —$CF_3$, and —$CF_2CH_3$;
$R^7$ is selected from fluorine and chlorine; and
$R^8$ is selected from methoxy, ethoxy, cyclopropyl, and ethyl.

In another embodiment, in Formula (II-A16):
$R^6$ is methoxy;
$R^7$ is fluorine; and
$R^8$ is selected from lower alkyl, cycloalkyl, and lower alkoxy.

In another embodiment, in Formula (II-A16):
$R^6$ is methoxy;
$R^7$ is fluorine; and
$R^8$ is selected from methyl, ethyl, cyclopropyl, methoxy, and ethoxy.

In another embodiment, in Formula (II-A16):
$R^6$ is methoxy;
$R^7$ is fluorine; and
$R^8$ is methyl.

In another embodiment, in Formula (II-A16):
$R^6$ is methoxy;
$R^7$ is fluorine; and
$R^8$ is ethyl.

In another embodiment, in Formula (II-A16):
$R^6$ is methoxy;
$R^7$ is fluorine; and
$R^8$ is cyclopropyl.

In another embodiment, in Formula (II-A16):
$R^6$ is methoxy;
$R^7$ is fluorine; and
$R^8$ is methoxy.

In another embodiment, 1 to 3 carbon atoms of the compounds of the invention may be replaced with 1 to 3 silicon atoms so long as all valency requirements are satisfied.

In another embodiment, the compounds of the invention are each of the compounds of Table I below and have a structure shown for the corresponding example in the preparative examples below.

Other embodiments, the present invention includes tautomers and stereoisomers of each of the compounds in Table I below, and pharmaceutically acceptable salts and solvates of said compounds, said stereoisomers, and/or said tautomers.

In another embodiment, a compound of the invention is the compound of example 1 in Table I below or a tautomer thereof. In another embodiment, a compound of the invention is a pharmaceutically acceptable salt of said compound or said tautomer.

In another embodiment, a compound of the invention is the compound of example 2 in Table I below or a tautomer thereof. In another embodiment, a compound of the invention is a pharmaceutically acceptable salt of said compound or said tautomer.

In another embodiment, a compound of the invention is the compound of example 3 in Table I below or a tautomer thereof. In another embodiment, a compound of the invention is a pharmaceutically acceptable salt of said compound or said tautomer.

In another embodiment, a compound of the invention is the compound of example 4 in Table I below or a tautomer thereof. In another embodiment, a compound of the invention is a pharmaceutically acceptable salt of said compound or said tautomer.

In another embodiment, a compound of the invention is the compound of example 5 in Table I below or a tautomer thereof. In another embodiment, a compound of the invention is a pharmaceutically acceptable salt of said compound or said tautomer.

In another embodiment, a compound of the invention is the compound of example 6 in Table I below or a tautomer thereof. In another embodiment, a compound of the invention is a pharmaceutically acceptable salt of said compound or said tautomer.

In another embodiment, a compound of the invention is the compound of example 7 in Table I below or a tautomer thereof. In another embodiment, a compound of the invention is a pharmaceutically acceptable salt of said compound or said tautomer.

In another embodiment, a compound of the invention is the compound of example 8 in Table I below or a tautomer thereof. In another embodiment, a compound of the invention is a pharmaceutically acceptable salt of said compound or said tautomer.

In another embodiment, a compound of the invention is the compound of example 9 in Table I below or a tautomer thereof. In another embodiment, a compound of the invention is a pharmaceutically acceptable salt of said compound or said tautomer.

In another embodiment, a compound of the invention is the compound of example 10 in Table I below or a tautomer thereof. In another embodiment, a compound of the invention is a pharmaceutically acceptable salt of said compound or said tautomer.

In another embodiment, a compound of the invention is the compound of example 11 in Table I below or a tautomer thereof. In another embodiment, a compound of the invention is a pharmaceutically acceptable salt of said compound or said tautomer.

In another embodiment, a compound of the invention is the compound of example 12 in Table I below or a tautomer thereof. In another embodiment, a compound of the invention is a pharmaceutically acceptable salt of said compound or said tautomer.

In another embodiment, a compound of the invention is the compound of example 13 or a tautomer thereof. In another embodiment, a compound of the invention is a pharmaceutically acceptable salt of said compound or said tautomer.

In another embodiment, a compound of the invention is the compound of example 14 in Table I below or a tautomer thereof. In another embodiment, a compound of the invention is a pharmaceutically acceptable salt of said compound or said tautomer.

In another embodiment, a compound of the invention is the compound of example 15 or a tautomer thereof. In another embodiment, a compound of the invention is a pharmaceutically acceptable salt of said compound or said tautomer.

In another embodiment, a compound of the invention is the compound of example 16 in Table I below or a tautomer thereof. In another embodiment, a compound of the invention is a pharmaceutically acceptable salt of said compound or said tautomer.

In another embodiment, a compound of the invention is the compound of example 17 in Table I below or a tautomer thereof. In another embodiment, a compound of the invention is a pharmaceutically acceptable salt of said compound or said tautomer.

In another embodiment, a compound of the invention is the compound of example 18 in Table I below or a tautomer thereof. In another embodiment, a compound of the invention is a pharmaceutically acceptable salt of said compound or said tautomer.

In another embodiment, a compound of the invention is the compound of example 19 in Table I below or a tautomer thereof. In another embodiment, a compound of the invention is a pharmaceutically acceptable salt of said compound or said tautomer.

In another embodiment, a compound of the invention is the compound of example 20 in Table I below or a tautomer thereof. In another embodiment, a compound of the invention is a pharmaceutically acceptable salt of said compound or said tautomer.

In another embodiment, a compound of the invention is the compound of example 20 in Table I below or a tautomer thereof. In another embodiment, a compound of the invention is a pharmaceutically acceptable salt of said compound or said tautomer.

In another embodiment, a compound of the invention is the compound of example 20 in Table I below or a tautomer thereof. In another embodiment, a compound of the invention is a pharmaceutically acceptable salt of said compound or said tautomer.

In another embodiment, a compound of the invention is the compound of example 20 in Table I below or a tautomer thereof. In another embodiment, a compound of the invention is a pharmaceutically acceptable salt of said compound or said tautomer.

In another embodiment, a compound of the invention is the compound of example 21 in Table I below or a tautomer thereof. In another embodiment, a compound of the invention is a pharmaceutically acceptable salt of said compound or said tautomer.

In another embodiment, a compound of the invention is the compound of example 22 in Table I below or a tautomer thereof. In another embodiment, a compound of the invention is a pharmaceutically acceptable salt of said compound or said tautomer.

In another embodiment, a compound of the invention is the compound of example 23 in Table I below or a tautomer thereof. In another embodiment, a compound of the invention is a pharmaceutically acceptable salt of said compound or said tautomer.

In another embodiment, a compound of the invention is the compound of example 24 in Table I below or a tautomer thereof. In another embodiment, a compound of the invention is a pharmaceutically acceptable salt of said compound or said tautomer.

In another embodiment, a compound of the invention is the compound of example 25 in Table I below or a tautomer thereof. In another embodiment, a compound of the invention is a pharmaceutically acceptable salt of said compound or said tautomer.

In another embodiment, a compound of the invention is the compound of example 26 in Table I below or a tautomer thereof. In another embodiment, a compound of the invention is a pharmaceutically acceptable salt of said compound or said tautomer.

In another embodiment, a compound of the invention is the compound of example 27 in Table I below or a tautomer thereof. In another embodiment, a compound of the invention is a pharmaceutically acceptable salt of said compound or said tautomer.

In another embodiment, a compound of the invention is the compound of example 28 in Table I below or a tautomer thereof. In another embodiment, a compound of the invention is a pharmaceutically acceptable salt of said compound or said tautomer.

In another embodiment, a compound of the invention is the compound of example 29 in Table I below or a tautomer thereof. In another embodiment, a compound of the invention is a pharmaceutically acceptable salt of said compound or said tautomer.

In another embodiment, a compound of the invention is the compound of example 30 in Table I below or a tautomer thereof. In another embodiment, a compound of the invention is a pharmaceutically acceptable salt of said compound or said tautomer.

In another embodiment, a compound of the invention is the compound of example 31 in Table I below or a tautomer thereof. In another embodiment, a compound of the invention is a pharmaceutically acceptable salt of said compound or said tautomer.

In another embodiment, a compound of the invention is the compound of example 32 in Table I below or a tautomer thereof. In another embodiment, a compound of the invention is a pharmaceutically acceptable salt of said compound or said tautomer.

In another embodiment, a compound of the invention is the compound of example 33 in Table I below or a tautomer thereof. In another embodiment, a compound of the invention is a pharmaceutically acceptable salt of said compound or said tautomer.

In another embodiment, a compound of the invention is the compound of example 34 in Table I below or a tautomer thereof. In another embodiment, a compound of the invention is a pharmaceutically acceptable salt of said compound or said tautomer.

In another embodiment, a compound of the invention is the compound of example 35 in Table I below or a tautomer thereof. In another embodiment, a compound of the invention is a pharmaceutically acceptable salt of said compound or said tautomer.

In another embodiment, a compound of the invention is the compound of example 36 in Table I below or a tautomer thereof. In another embodiment, a compound of the invention is a pharmaceutically acceptable salt of said compound or said tautomer.

In another embodiment, a compound of the invention is the compound of example 37 in Table I below or a tautomer thereof. In another embodiment, a compound of the invention is a pharmaceutically acceptable salt of said compound or said tautomer.

In another embodiment, a compound of the invention is the compound of example 38 in Table I below or a tautomer thereof. In another embodiment, a compound of the invention is a pharmaceutically acceptable salt of said compound or said tautomer.

In another embodiment, a compound of the invention is the compound of example 39 in Table I below or a tautomer thereof. In another embodiment, a compound of the invention is a pharmaceutically acceptable salt of said compound or said tautomer.

In another embodiment, a compound of the invention is the compound of example 40 in Table I below or a tautomer thereof. In another embodiment, a compound of the invention is a pharmaceutically acceptable salt of said compound or said tautomer.

In another embodiment, a compound of the invention is the compound of example 41 in Table I below or a tautomer thereof. In another embodiment, a compound of the invention is a pharmaceutically acceptable salt of said compound or said tautomer.

In another embodiment, a compound of the invention is the compound of example 42 in Table I below or a tautomer thereof. In another embodiment, a compound of the invention is a pharmaceutically acceptable salt of said compound or said tautomer.

In another embodiment, a compound of the invention is the compound of example 43 in Table I below or a tautomer thereof. In another embodiment, a compound of the invention is a pharmaceutically acceptable salt of said compound or said tautomer.

In another embodiment, a compound of the invention is the compound of example 44 in Table I below or a tautomer thereof. In another embodiment, a compound of the invention is a pharmaceutically acceptable salt of said compound or said tautomer.

In another embodiment, a compound of the invention is the compound of example 45 in Table I below or a tautomer thereof. In another embodiment, a compound of the invention is a pharmaceutically acceptable salt of said compound or said tautomer.

TABLE I

| Example No. | Compound |
| --- | --- |
| 1 | [chemical structure] |
| 2 | [chemical structure] |
| 3 | [chemical structure] |

TABLE I-continued

| Example No. | Compound |
|---|---|
| 4 | (structure with phenyl, imino-methyl-pyrimidinone spiro pyrrolidine, N-linked to 6-methyl-5-fluoro-4-ethoxy-pyrimidine) |
| 5 | (structure with phenyl, imino-methyl-pyrimidinone spiro pyrrolidine, N-linked to 6-methyl-5-fluoro-4-ethyl-pyrimidine) |
| 6 | (structure with phenyl, imino-methyl-pyrimidinone spiro pyrrolidine, N-linked to 4-methoxy-5-fluoro-6-ethyl-pyrimidine) |
| 7 | (structure with phenyl, imino-methyl-pyrimidinone spiro pyrrolidine, N-linked to 6-methyl-5-chloro-4-cyclopropyl-pyrimidine) |
| 8 | (structure with 2,4,5-trifluorophenyl, imino-methyl-pyrimidinone spiro pyrrolidine, N-linked to 6-methyl-5-fluoro-4-methoxy-pyrimidine) |
| 9 | (structure with 2,5-difluorophenyl, imino-methyl-pyrimidinone spiro pyrrolidine, N-linked to 4,6-dimethoxy-5-fluoro-pyrimidine) |
| 10 | (structure with 2,4-difluorophenyl, imino-methyl-pyrimidinone spiro pyrrolidine, N-linked to 4,6-dimethoxy-5-fluoro-pyrimidine) |
| 11 | (structure with 2,6-difluorophenyl, imino-methyl-pyrimidinone spiro pyrrolidine, N-linked to 6-methyl-5-fluoro-4-methoxy-pyrimidine) |

TABLE I-continued
| Example No. | Compound |
|---|---|
| 12 | 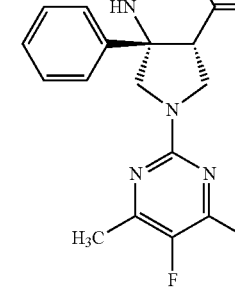 |
| 13 | |
| 14 | |
| 15 | |
| 16 | 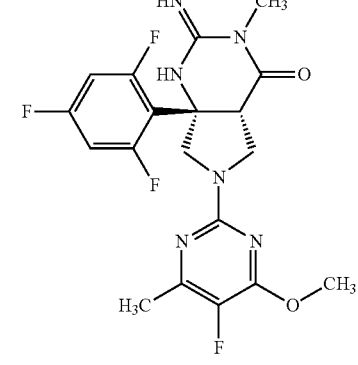 |
| 17 | |
| 18 | |
| 19 | |

TABLE I-continued

| Example No. | Compound |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE I-continued

| Example No. | Compound |
|---|---|
| 28 | (structure) |
| 29 | (structure) |
| 30 | (structure) |
| 31 | (structure) |
| 32 | (structure) |
| 33 | (structure) |
| 34 | (structure) |
| 35 | (structure) |

TABLE I-continued
| Example No. | Compound |
|---|---|
| 36 | 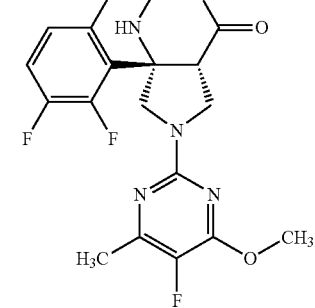 |
| 37 | |
| 38 | |
| 39 | |
| 40 | 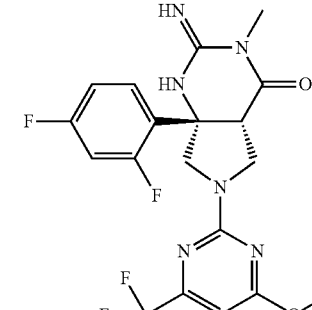 |
| 41 | |
| 42 | |
| 43 | |

TABLE I-continued

| Example No. | Compound |
|---|---|
| 44 | 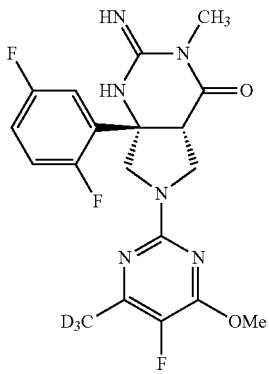 [SMILES: [2H]C([2H])([2H])c1nc(N2C[C@H]3C(=O)N(C)C(=N)N[C@@]3(c3cc(F)ccc3F)C2)nc(OC)c1F] |
| 45 | 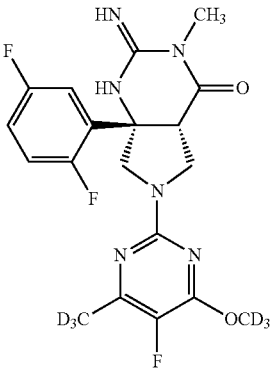 |

In another embodiment, the invention provides a composition comprising at least one compound of the invention, or a tautomer or stereoisomer thereof, or salt or solvate of said compound, said stereoisomer, or said tautomer, and a suitable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one solvate of a compound of the invention, or a tautomer or isomer thereof, or pharmaceutically acceptable salt or solvate of said compound or said tautomer, and a pharmaceutically acceptable carrier or diluent.

In another embodiment, the invention provides a pharmaceutical composition comprising at least one pharmaceutically acceptable salt of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one tautomer of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, together with at least one additional therapeutic agent, and a pharmaceutically acceptable carrier or diluent.

Non-limiting examples of additional therapeutic agents for use in combination with the compounds of the invention include drugs selected from the group consisting of: (a) drugs useful for the treatment of Alzheimer's disease and/or drugs useful for treating one or more symptoms of Alzheimer's disease, (b) drugs useful for inhibiting the synthesis Aβ, and (c) drugs useful for treating neurodegenerative diseases.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit said pathology or pathologies.

In embodiments of the invention comprising at least one additional therapeutic agent, additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abets vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

In another embodiment, the invention provides a pharmaceutical composition comprising an effective amount of one or more (e.g., one) compounds of the invention, and effective amount of one or more cholinesterase inhibitors (e.g., acetyl- and/or butyrylchlolinesterase inhibitors), and a pharmaceutically acceptable carrier.

In another embodiment, the invention provides a pharmaceutical composition comprising an effective amount of one or more (e.g., one) compounds of the invention, and effective amount of one or more muscarinic antagonists (e.g., $m_1$ agonists or $m_2$ antagonists), and a pharmaceutically acceptable carrier.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), N-methyl-D-aspartate receptor inhibitors (such as, for example, Namenda® (memantine HCl)); anti-amyloid antibodies (such as bapineuzumab, Wyeth/Elan), gamma secretase inhibitors, gamma secretase modulators, and beta secretase inhibitors other than the compounds of the invention.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), N-methyl-D-aspartate receptor inhibitors (such as, for example, Namenda® (memantine HCl)).

In one embodiment, the invention provides combinations comprising an effective (i.e., therapeutically effective) amount of one or more compounds of the invention, in combination with an effective (i.e., therapeutically effective) amount of one or more gamma secretase inhibitors.

In one embodiment, the invention provides combinations comprising an effective (i.e., therapeutically effective) amount of one or more compounds of the invention, in combination with an effective (i.e., therapeutically effective) amount of one or more gamma secretase modulators.

In one embodiment, the invention provides combinations comprising an effective (i.e., therapeutically effective) amount of one or more compounds of the invention, or a tautomer or stereoisomer thereof, or pharmaceutically acceptable salt or solvate of said compound, said stereoisomer, or said tautomer, in combination with an effective (i.e., therapeutically effective) amount of one or more gamma secretase inhibitors and in further combination with one or more gamma secretase modulators.

In another embodiment, the invention provides a compound of the invention, or a tautomer or stereoisomer thereof, or pharmaceutically acceptable salt or solvate of said compound, said stereoisomer, or said tautomer, in pure form.

In another embodiment, the invention provides a compound of the invention or a tautomer or stereoisomer thereof, or pharmaceutically acceptable salt or solvate of said compound, said stereoisomer, or said tautomer, in isolated form.

In another embodiment, the invention provides a compound of the invention or a tautomer or stereoisomer thereof, or pharmaceutically acceptable salt or solvate of said compound, said stereoisomer, or said tautomer, in pure and isolated form.

Esters and prodrugs of the compounds of the invention, or tautomers or stereoisomers thereof, or pharmaceutically acceptable salts or solvates of said compounds, said stereoisomers, and/or said tautomers, are also contemplated as being included within the scope of the invention, and are described more fully below.

Deuterates of the compounds of the invention, or tautomers or stereoisomers of said deuterates, or pharmaceutically acceptable salts or solvates of said deuterates, said stereoisomers, and/or said tautomers, are also contemplated as being included within the scope of the invention, and are described more fully below.

In another embodiment, the invention provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a method of inhibiting β-secretase comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase.

In another embodiment, the invention provides a method of inhibiting β-secretase in a patient in need thereof comprising administering at least one compound of the invention, or a tautomer or stereoisomer thereof, or pharmaceutically acceptable salt or solvate of said compound, said stereoisomer, or said tautomer, in a therapeutically effective amount to inhibit β-secretase in said patient.

In another embodiment, the invention provides a method of inhibiting BACE-1 comprising exposing a population of cells expressing BACE-1 to at least one compound of the invention, or a tautomer or stereoisomer thereof, or pharmaceutically acceptable salt or solvate of said compound or said tautomer, in an amount effective to inhibit BACE-1 in said patient. In one such embodiment, said population of cells is in viva. In another such embodiment, said population of cells is ex vivo. In another such embodiment, said population of cells is in vitro.

In another embodiment, the invention provides a method of inhibiting BACE-1 in a patient in need thereof comprising administering to said patient at least one compound of the invention, or a tautomer or stereoisomer thereof, or pharmaceutically acceptable salt or solvate of said compound, said stereoisomer, or said tautomer, in a therapeutically effective amount to inhibit BACE-1 in said patient.

In another embodiment, the invention provides a method of inhibiting the formation of Aβ from APP in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ formation.

In another embodiment, the invention provides a method of inhibiting the formation of Aβ plaque in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ plaque formation.

In another embodiment, the invention provides a method of inhibiting the formation of Aβ fibrils in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ fibrils and Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of senile plaques and/or neurofibrillary tangles in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of treating, preventing, and/or delaying the onset of an amyloid β pathology ("Aβ pathology") and/or one or more symptoms of said pathology comprising administering at least one compound of the invention, or a tautomer or stereoisomer thereof, or pharmaceutically acceptable salt or solvate of said compound, said stereoisomer, or said tautomer, to a patient in need thereof in an amount effective to treat said pathology.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating one or more neurodegenerative diseases, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of inhibiting the deposition of amyloid protein (e.g., amyloid beta protein) in, on or around neurological tissue (e.g., the brain), comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of inhibiting the deposition of amyloid protein (e.g., amyloid beta protein) in, on or around neurological tissue (e.g., the brain), comprising administering an effective (i.e., therapeutically effective) amount of a compound of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) in combination with an effective (i.e., therapeutically effective) amount of one or more additional therapeutic agents useful for treating Alzheimer's disease to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more compounds selected from the group consisting of Aβ antibody inhibitors, gamma secretase inhibitors and beta secretase inhibitors other than a compound of the invention.

In one embodiment, the invention provides a method of treating Alzheimer's disease, comprising administering an effective amount of one or more (e.g., one) compounds of the invention (or a tautomer or stereoisomer thereof, or pharmaceutically acceptable salt or solvate of said compound, said stereoisomer, or said tautomer), in combination with an effective amount of one or more compounds selected from the group consisting of Aβ antibody inhibitors, gamma secretase inhibitors and beta secretase inhibitors.

In one embodiment, the invention provides a method of treating Alzheimer's disease, comprising administering an effective amount of one or more (e.g., one) compounds of the invention (or a tautomer or stereoisomer thereof, or pharmaceutically acceptable salt or solvate of said compound, said stereoisomer, or said tautomer), in combination with an effective amount of one or more BACE inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of Exelon (rivastigmine).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of Cognex (tacrine).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of a Tau kinase inhibitor.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more Tau kinase inhibitor (e.g., GSK3beta inhibitor, cdk5 inhibitor, ERK inhibitor).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one anti-Abeta vaccination (active immunization).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more APP ligands.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more agents that upregulate insulin degrading enzyme and/or neprilysin.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more fibrates (for example, clofibrate, Clofibride, Etofibrate, Aluminium Clofibrate).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more LXR agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more LRP mimics.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more 5-HT6 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more nicotinic receptor agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more H3 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more histone deacetylase inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more hsp90 inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more m1 muscarinic receptor agonists.

Another embodiment of this invention is directed to a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more 5-HT6 receptor antagonists, or mGluR1, or mGluR5 positive allosteric modulators or agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more mGluR2/3 antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more anti-inflammatory agents that can reduce neuroinflammation.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more Prostaglandin EP2 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more PAI-1 inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more agents that can induce Abeta efflux such as gelsolin.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

In one embodiment, the invention provides a method of treating mild cognitive impairment, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating mild cognitive impairment, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating glaucoma, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating glaucoma, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating cerebral amyloid angiopathy, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating cerebral amyloid angiopathy, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating stroke, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating stroke, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating dementia, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating dementia, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating microgliosis, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating microgliosis, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating brain inflammation, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating brain inflammation, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating olfactory function loss, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating olfactory function loss, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient (as described below), the combined quantities of the compound of the invention and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) inhibit the activity of BACE-1.

In various embodiments, the invention provides any one of the methods disclosed above and below wherein the compound(s) of the invention is a compound or compounds selected from the group consisting of the exemplary compounds of the invention described below.

In various embodiments, the invention provides any one of the pharmaceutical compositions disclosed above and below wherein the compound(s) of the invention is a compound or compounds selected from the group consisting of the exemplary compounds of the invention described below.

Other embodiments of this invention are directed to any one of the embodiments above or below that are directed to compounds of the invention, or the use of compounds of the invention (e.g. the embodiments directed to methods of treatment, pharmaceutical compositions and kits).

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

In another embodiment, the invention provides a kit comprising: (a) one or more compounds of the invention, or a tautomer or stereoisomer thereof, or pharmaceutically acceptable salt or solvate of said compound, said stereoisomer, or said tautomer, preferably provided as a pharmaceutical composition and in a suitable container or containers and/or with suitable packaging; (b) optionally one or more additional active agents, which if present are preferably provided as a pharmaceutical composition and in a suitable container or containers and/or with suitable packaging; and (c) instructions for use, for example written instructions on how to administer the compound or compositions.

In another embodiment, the invention provides a kit comprising a single container or multiple containers: (a) a pharmaceutically acceptable composition comprising one or more compounds of claim 1, or a tautomer or stereoisomer thereof, or pharmaceutically acceptable salt or solvate of said compound, said stereoisomer, or said tautomer, (b) optionally pharmaceutically acceptable composition comprising one or more additional therapeutic agents; and (c) instructions for use their use. Said kit may optionally comprise labeling appropriate to the intended use or uses.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"At least one" means one or more than one, for example, 1, 2, or 3, or in another example, 1 or 2, or in another example 1.

"One or more" means one or more than one, for example, 1, 2, or 3, or in another example, 1 or 2, or in another example 1.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

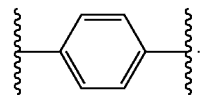

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

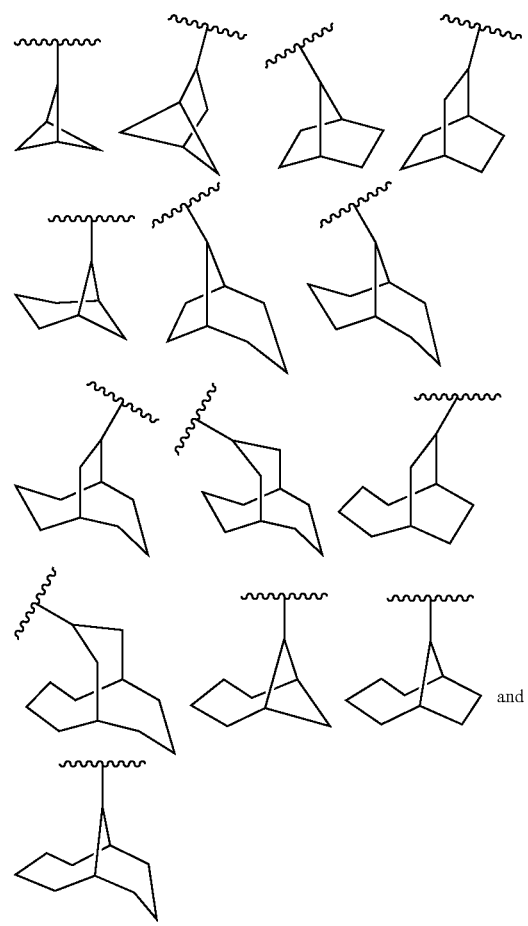

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide,"

when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

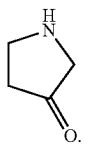

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

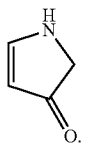

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

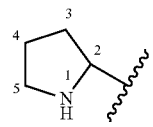

there is no —OH attached directly to carbons marked 2 and 5.

It should also be noted that tautomeric forms of the compounds of the invention are also contemplated as being within the scope of the invention. Thus, for example, the formulas:

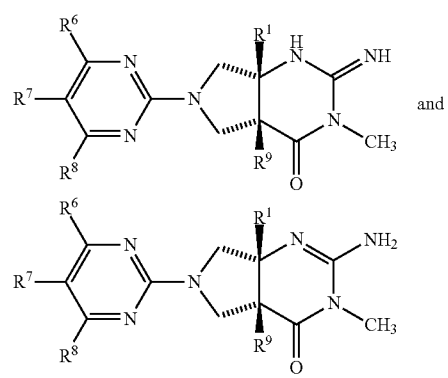

are considered equivalent in the various compounds of the invention.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

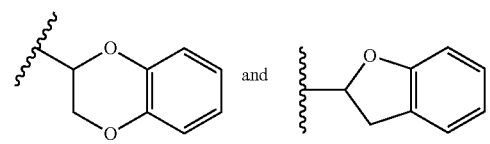 [SMILES: *C1COc2ccccc2O1 ; *C1Cc2ccccc2O1]

The bond to the parent moiety is through a non-aromatic carbon atom.

It is also understood that the terms "arylfused aryl", "arylfused cycloalkyl", "arylfused cycloalkenyl", "arylfused heterocycloalkyl", arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Spirocycloalkyl" means a cycloalkyl group attached to a parent moiety at a single carbon atom. Non-limiting examples of spirocycloalkyl wherein the parent moiety is a cycloalkyl include spiro[2.5]octane, spiro[2.4]heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in —N($R^8$)$_2$, or a variable appears more than once in a structure presented herein, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (II)," one to three compounds of the invention, e.g., of Formula (II) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $Y_1Y_2N$—, $Y_1Y_2N$-alkyl-, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C($CH_3$)$_2$— and the like which form moieties such as, for example:

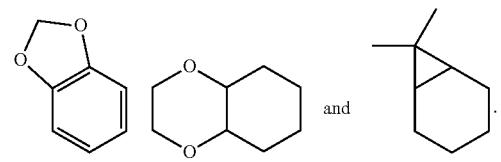

As used herein, the term "composition" is intended to encompass a product comprising the specified ingredients in the specified amounts, as well as any product which results, directly or indirectly, from combination of the specified ingredients in the specified amounts.

The line -----, as a bond generally indicates a mixture of, or either of, the possible isomers, e.g., containing (R)- and (S)-stereochemistry. For example:

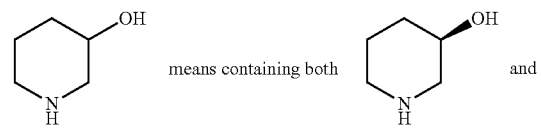

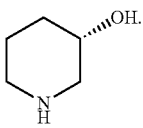

The wavy line ∿∿∿, as used herein, indicates a point of attachment to the rest of the compound. For example, each wavy line in the following structure:

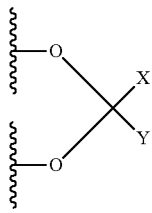

indicates a point of attachment to the core structure, as described herein.

Lines drawn into the ring systems, such as, for example:

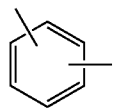

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

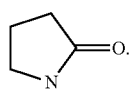

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

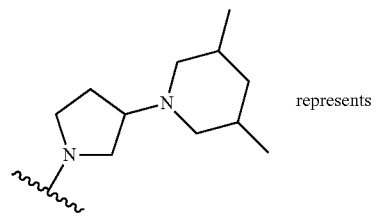 represents

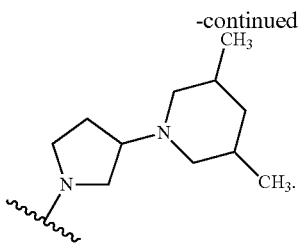

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)

ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of the invention contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)$OY^1$ wherein $Y^1$ is H, ($C_1$-$C_6$)alkyl or benzyl, —C($OY^2$)$Y^3$ wherein $Y^2$ is ($C_1$-$C_4$) alkyl and $Y^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent. Non-limiting examples of deuterated compounds of the invention are described hereinbelow.

Polymorphic forms of the compounds of the invention, and of the salts, solvates, esters and prodrugs of the compounds of the invention, are intended to be included in the present invention.

Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

In one embodiment, the compound is administered orally.

In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose.

PREPARATIVE EXAMPLES

Compounds of the invention can be made using procedures known in the art. The following reaction schemes show typical procedures, but those skilled in the art will recognize that other procedures can also be suitable.

Where NMR data are presented, spectra were obtained on either a Varian VXR-200 (200 MHz, $^1$H), Varian Gemini-300 (300 MHz) or XL-400 (400 MHz), or Bruker AVANCE 300 or 500 MHz spectrometers and are reported as ppm ($\delta$) down field from Me$_4$Si with number of protons, multiplicities, and coupling constants in Hertz indicated parenthetically. Where LC/MS data are presented, analyses were performed using an Applied Biosystems API-100 mass spectrometer and Shimadzu SCL-10A LC column: Alltech platinum C18, 3 micron, 33 mm×7 mm ID; gradient flow: 0 min-10% CH$_3$CN/ 0.1% TFA/water, 5 min-95% CH$_3$CN/0.1% TFA/water, 7 min-95% CH$_3$CN/0.1% TFA/water, 7.5 min-10% CH$_3$CN/ 0.1% TFA/water, 9 min-stop; or with an Inertsil ODS-2 column; gradient flow: 0 min-10% CH$_3$CN/0.05% TFA/water, 4 min-100% CH$_3$CN/0.05% TFA/water, 2 min-100% CH$_3$CN/ 0.05% TFA/water. The observed parent ion is given. Optical rotation data was obtained on a Perkin Elmer 341 polarimeter and substrate concentration c is reported in mg/mL.

Techniques, solvents and reagents may be referred to by their following abbreviations:
Thin layer chromatography: TLC
High performance liquid chromatography: HPLC
ethyl acetate: AcOEt or EtOAc
methanol: MeOH
ether or diethyl ether: Et$_2$O
tetrahydrofuran: THF
Acetonitrile: MeCN
1,2-dimethoxyethane: DME
Trifluoroacetic acid: TFA
Dimethylacetamide: DMA
Dimethylformamide: DMF
Dimethylsulfoxide: DMSO
triethylamine: Et$_3$N or TEA
tert-Butoxycarbonyl: t-Boc or Boc
2-(Trimethylsilyl)ethoxycarbonyl: Teoc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
centimeters: cm
room temperature (ambient, about 25° C.): rt
Retention time: t$_R$
N-bromosuccinimide: NBS
Methyl magnesium bromide: MeMgBr
iron(III) acetylacetonate: Fe(acac)$_3$
Diphenylphosphoryl azide: DPPA
1-(3-Dimethylaminopropyl)-3-ethylcarbodiimide hydrochloride: EDCl
Diisopropylethylamine: DIEA or iPr$_2$NEt
Diisopropylamine: iPr$_2$NH
2-(Trimethylsilyl)ethanol: TMSethanol
3-Chloroperoxybenzoic acid: mCPBA
n-Butyllithium: nBuLi
lithium diisopropylamide: LDA
[1,1'-Bis(diphenylphosphino)ferrocene]dichloropalladium (II): PdCl$_2$dppf
Palladium(II)acetate: Pd(OAc)$_2$
Methanesulfonyl chloride: MeSO$_2$Cl
Benzyl: Bn Method A

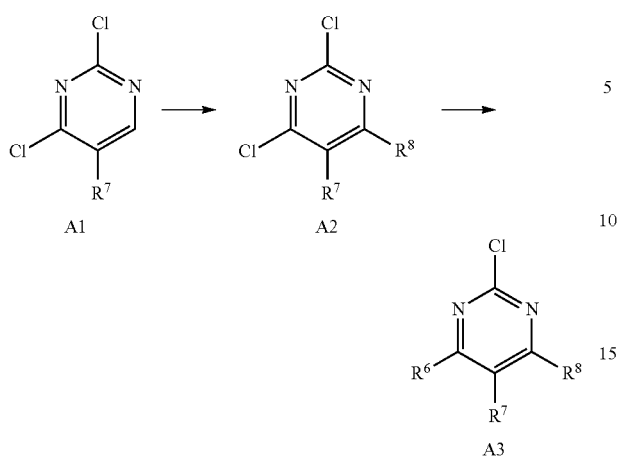

Method A, Step 1

A literature procedure was adapted (M. Butters, J. Ebbs, S. P. Green, J. MacRae, M. C. Morland, C. W. Murtiashaw and A. J. Pettman *Organic Process Research & Development* 2001, 5, 28-36). To a solution of 3.0 M MeMgBr in $Et_2O$ (15 mL, 45 mmol, 1.5 equiv.) in THF (20 mL) was added a solution of A1 ($R^7$=F, 5 g, 30 mmol, 1 equiv.) in DME (20 mL) while maintaining the temperature below 15° C. The resulting solution was stirred at 15° C. for 1 hour and then was cooled to 0° C. A solution of $Et_3N$ (4.17 mL, 30 mmol, 1 equiv.) in THF (10 mL) was added slowly to the reaction mixture maintaining the internal temperature ~5° C., then a solution of iodine (30 mmol, 1 equiv.) in THF (10 mL) was added. The reaction mixture was quenched with water, warmed to rt, extracted with EtOAc and concentrated. The crude product was purified by silica gel column chromatography ($CH_2Cl_2$/hexanes) to afford A2 ($R^8$=Me, $R^7$=F) in 74% yield.

Method A, Step 2

To a solution of A2 ($R^7$=F, $R^8$=Me, 563 mg, 3.11 mmol) in THF (6 mL) was added 25% sodium methoxide in MeOH (671 mg) while cooling at 0° C. The resulting solution was slowly warmed to rt over 1 hr and then diluted with water and extracted with EtOAc. The EtOAc extract was concentrated and the residue was purified by silica gel column chromatography (EtOAc/hexanes) to provide A3 ($R^6$=MeO, $R^7$=F and $R^8$=Me) in quantitative yield.

The following compounds were synthesized using similar methods:

A4

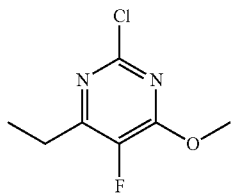

A5

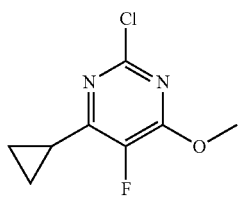

A6

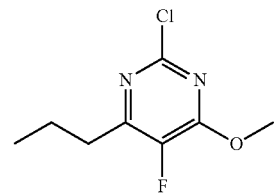

A7

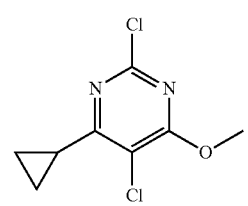

A8

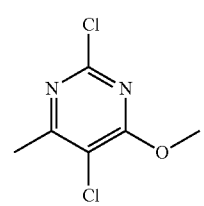

A9

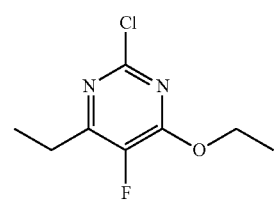

A10

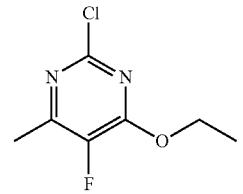

Method B

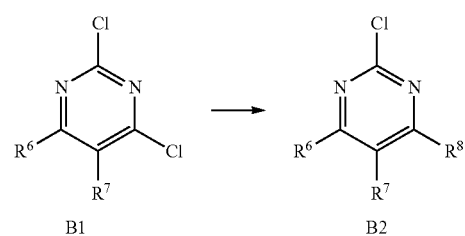

To a mixture of B1 ($R^6$=Me, $R^7$=F; 2.34 g, 12 mmol, 1 equiv.) and $Fe(acac)_3$ (0.213 mg, 0.606 mmol, 0.05 equiv.) in THF (40 mL) was slowly added a solution of MeMgBr in THF (17 mL, 24 mmol, 2 equiv.) while cooling the reaction mixture at −78° C. The reaction mixture was stirred at −78° C. for 3 hours and then quenched with sat. aqueous $NH_4Cl$, and extracted with EtOAc. The organic layer was concentrated and the crude product was purified by silica gel column chromatography (EtOAc/hexanes) to provide B2 (R⁶=R⁸=Me, R⁷=F) in 75% yield.

The following compounds were prepared by similar methods:

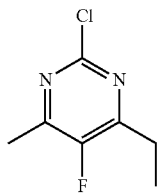

B3

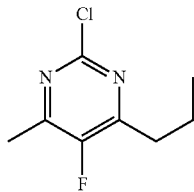

B4

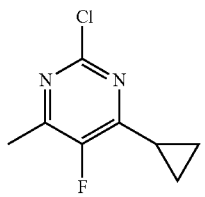

B5

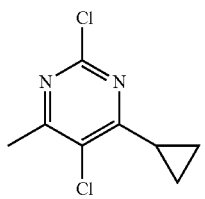

B6

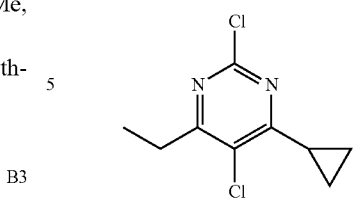

B7

Method C

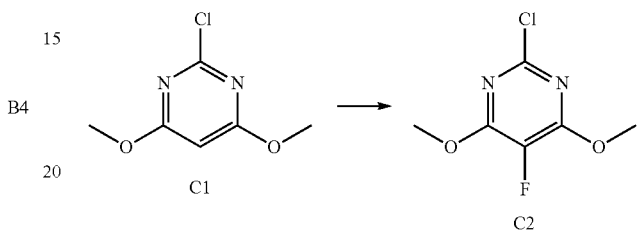

A round bottom flask containing anhydrous THF (8 mL) was cooled to 0° C. under N₂ with stirring, and nBuLi (2.5 M in hexane, 2.75 mL, 6.88 mmol) was added, followed by the addition of iPr₂NH (1.02 mL, 7.28 mmol). The reaction mixture was stirred at 0° C. for 30 minutes. To another round bottom flask was added 2-chloro-4,6-dimethoxypyrimidine C1 (1.00 g, 5.73 mmol) and anhydrous THF (50 mL). The solution was cooled to −78° C. under N₂ with stirring, to which the above freshly prepared LDA solution was added via syringe pump over one hour. After the addition of LDA, N-fluorobenzenesulfonimide (2.70 g, 8.56 mmol) in 10 mL of anhydrous THF was added via syringe pump over 15 minutes. The reaction mixture was stirred at −78° C. for 3 hours, then warmed to rt and stirred overnight. The reaction mixture was cooled to −78° C., quenched with sat. aqueous NH₄Cl (20 mL), allowed to warm to it and extracted with CH₂Cl₂ (3×50 mL). The combined organic layers were dried over Na₂SO₄, filtered and concentrated and the residue was purified by silica gel chromatography (Analogix; EtOAc/hexane, 0-2%) to give C2 (226 mg, 21%) as a white solid. ¹H NMR (400 MHz, CDCl₃) δ 3.99 (s).

Method D

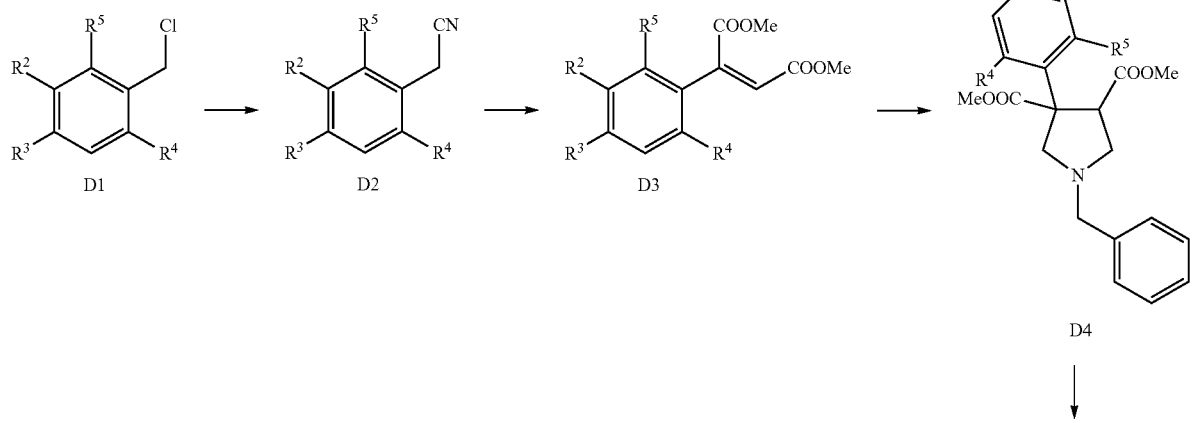

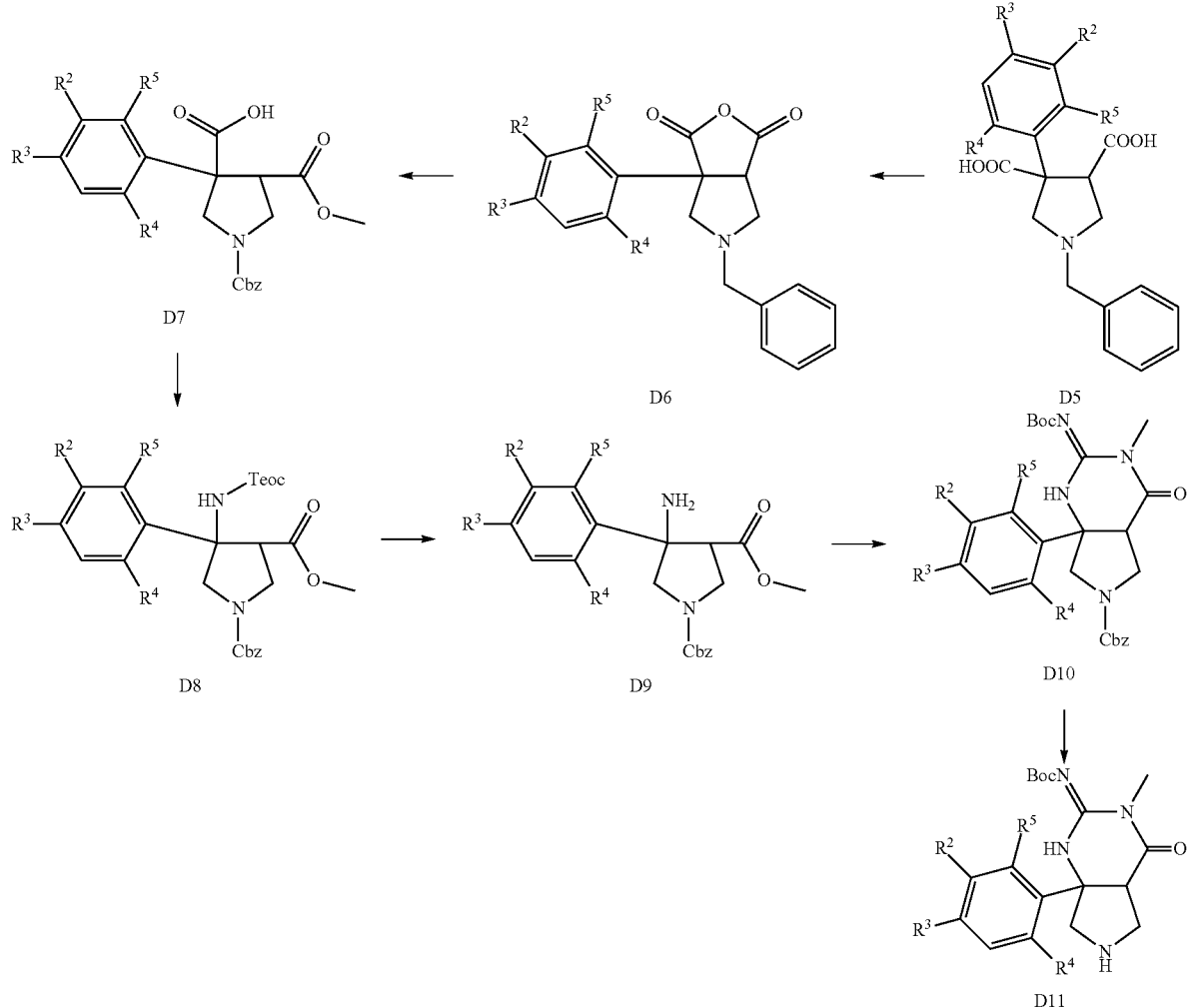

Method D, Step 1

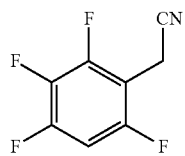

To a solution of 2,3,4,6-tetrafluorobenzyl chloride D1 ($R^2=R^3=R^4=R^5=F$, 25 g, 126 mmol) in MeCN (200 mL) was added KCN (9.9 g, 1.2 equiv. 152 mmol) and the resulting solution was refluxed for 4 hours. Then the reaction mixture was cooled to rt, filtered through a pad of celite, and the filtrate was concentrated. The residue was purified via a silica gel column (EtOAc/hexanes) to yield the nitrile D2 ($R^2=R^3=R^4=R^5=F$) in 80% yield. $^1$H NMR (CDCl$_3$) δ 6.89 (m, 1H), 3.72 (s, 2H).

Method D, Step 2

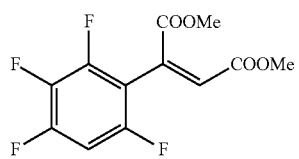 [SMILES: COC(=O)/C=C(\C(=O)OC)c1c(F)cc(F)c(F)c1F]

To a solution of nitrile D2 ($R^2=R^3=R^4=R^5=F$, 50 g, 264 mmol) in 500 mL MeOH was added glyoxylic acid monohydrate (29.2 g, 1.2 equiv., 317 mmol). To this mixture was added K$_2$CO$_3$ (77.7 g, 2.1 equiv., 555 mmol) in several portions while cooling at 0° C. The reaction mixture was stirred at 0° C. for 10 minutes and then at rt until the reaction was complete. The resulting suspension was filtered, and filtrate was evaporated to yield a solid, which was dissolved in 10% concentrated H$_2$SO$_4$ in formic acid (500 mL) and refluxed until the hydrolysis of the nitrile was complete. The reaction mixture was then diluted with water, extracted with EtOAc and evaporated. The residue was dissolved in 5% concentrated H$_2$SO$_4$ in MeOH (500 mL) and the mixture was refluxed until diester formation was complete. The resulting solution was evaporated to dryness, diluted with water, extracted with EtOAc, and the organic layer was concentrated. The residue was purified by silica gel column chromatography (EtOAc/hexanes) to yield the diester D3 ($R^2=R^3=R^4=R^5=F$) in 41% yield. $^1$H NMR (CDCl$_3$) δ 6.83 (m, 1H), 6.43 (s, 1H), 3.91-3.83 (m, 6H).

Method D, Step 3

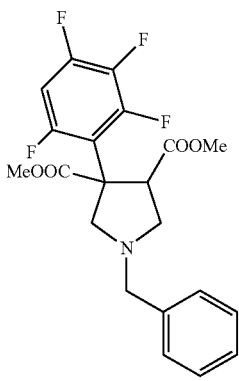 [SMILES: COC(=O)C1CN(Cc2ccccc2)CC1(C(=O)OC)c1c(F)cc(F)c(F)c1F]

To a solution of diester D3 ($R^2=R^3=R^4=R^5=F$, 8.0 g, 27.4 mmol) in THF (40 mL) was added N-methoxymethyl-N-trimethylsilylmethylbenzylamine (9.7 g, 41 mmol). To the resulting solution was added TFA (0.229 mL, 0.1 equiv., 2.98 mmol) at 0° C. The reaction mixture was stirred at 0° C. for 1 hr, then the ice bath was removed and the resulting solution was allowed to stir at it until the reaction was complete. The solution was evaporated to dryness and purified via a silica gel column (EtOAc/hexanes) to provide D4 ($R^2=R^3=R^4=R^5=F$) in 90% yield. $^1$H NMR (CDCl$_3$) δ 7.30-7.25 (m, 5H), 6.83 (m, 1H), 3.75-3.66 (m, 9H), 3.40 (m, 2H), 3.19 (m, 2H).

Method D, Step 4

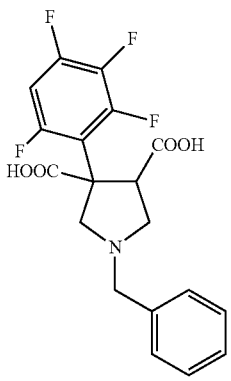 [SMILES: O=C(O)C1CN(Cc2ccccc2)CC1(C(=O)O)c1c(F)cc(F)c(F)c1F]

A solution of D4 ($R^2=R^3=R^4=R^5=F$, 10 g) in 15% aqueous H$_2$SO$_4$ (100 mL) was heated under reflux for 24 hours or until the reaction was complete. The reaction mixture was cooled to it and adjusted to pH 3 with 6N NaOH, and the resulting precipitate was collected and dried to give the product D5 ($R^2=R^3=R^4=R^5=F$).

Method D, Step 5

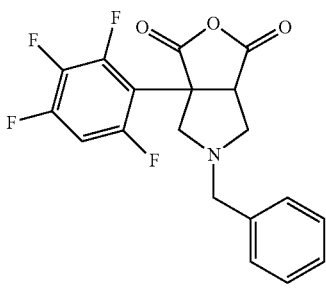 [SMILES: O=C1OC(=O)C2(c3c(F)cc(F)c(F)c3F)CN(Cc3ccccc3)CC12]

To a flask containing 10 g of diacid D5 ($R^2=R^3=R^4=R^5=F$) was added acetic anhydride (25 mL) and the mixture was heated at 90° C. for 1 hour. Then the reaction mixture was evaporated to dryness to give compound D6 ($R^2=R^3=R^4=R^5=F$).

Method D, Step 6

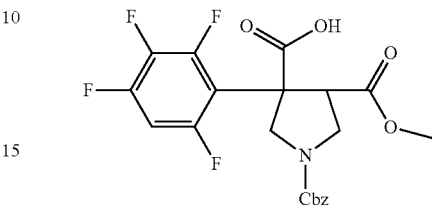

The cyclic anhydride D6 ($R^2=R^3=R^4=R^5=F$) was dissolved in CH$_2$Cl$_2$ (100 mL) and cooled to −78° C. To this solution was added a 1:2 mixture of Et$_3$N and MeOH (10 mL). The reaction mixture was slowly warmed to rt, then evaporated to dryness.

To a solution of this crude product (3 g) in MeOH (8 mL) was added 20% Pd(OH)$_2$ on carbon (800 mg, 0.20 equiv.) and the reaction mixture was stirred under an atmosphere of H$_2$ until the reaction was complete. The suspension was filtered through a pad of celite and the filtrate was evaporated to dryness. To a solution of the residue in THF (15 mL) was added benzyl chloroformate (1.23 mL, 1.5 equiv.) followed by Et$_3$N (2.4 mL, 3 equiv) at 0° C. The resulting solution was warmed to rt over 30 minutes and stirred until the reaction was complete. The reaction mixture was washed with 1 N HCl and the aqueous solution was extracted with EtOAc. The combined organic layers were concentrated and the residue was purified with a silica gel column (MeOH/CH$_2$Cl$_2$) to obtain D7 ($R^2=R^3=R^4=R^5=F$) in 70% yield. $^1$H NMR (CDCl$_3$) δ 7.34-7.31 (m, 5H), 6.83 (m, 1H), 5.13 (m, 2H), 4.6-4.4 (m, 1H), 3.95-3.64 (m, 7H).

Method D, Step 7

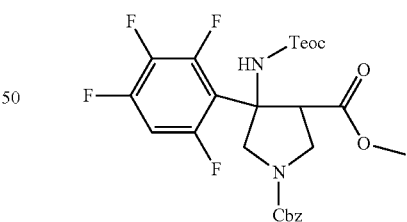

To a mixture of acid D7 ($R^2=R^3=R=R^5=F$, 1.6 g, 3.5 mmol, 1 equiv.) in toluene (8 mL) was added DPPA (2 equiv., 7.03 mmol, 1.5 mL) followed by Et$_3$N (1.9 mL, 4 equiv., 14 mmol) and the resulting mixture was stirred at rt until the acid was consumed. Then TMSethanol (2 mL, 4 equiv., 14 mmol) was added and the resulting solution was heated at 125° C. for 1 hour. The reaction mixture was cooled to rt and concentrated. The residue was subjected to silica gel column chromatography (EtOAc/hexanes) to give compound D8 ($R^2=R^3=R^4=R^5=F$) which was used directly in the next step.

Method D, Step 8

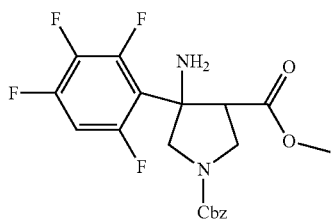 [SMILES: COC(=O)C1CN(C(=O)OCc2ccccc2)CC1(N)c1c(F)cc(F)c(F)c1F]

To D8 ($R^2=R^3=R^4=R^5=F$) obtained from step 7 was added 4N HCl (50 mL) and the reaction mixture was stirred for 24 hours. The resulting solution was evaporated to dryness to give crude D9 ($R^2=R^3=R^4=R^5=F$). $^1$H NMR (CD$_3$OD) δ 7.39-7.32 (m, 6H), 5.18 (s, 2H), 4.25-4.6 (m, 2H), 4.1 (m, 1H), 3.6-3.8 (m, 5H).

Method D, Step 9 enantiomer B

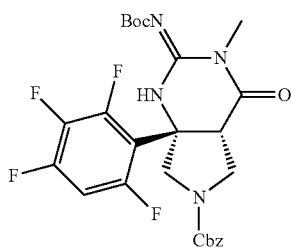

To a solution of D9 ($R^2=R^3=R^4=R^5=F$, 1.4 g, 3.28 mmol, 1 equiv.) in DMF (8 mL) was added N-Boc-N'-methylthiourea (0.936 g, 4.92 mmol, 1.5 equiv.), EDCl (0.936 g, 4.92 mmol, 1.5 equiv.) and DIEA (2.85 mL, 16.4 mmol, 5 equiv.) and the resulting solution was stirred at rt until the reaction was complete. The reaction mixture was diluted with EtOAc and washed with water. The EtOAc layer was evaporated and the residue was purified by silica gel chromatography (EtOAc/hexanes). The enantiomers were separated by chiral HPLC (Chiracel AD, 50 mL/min, 10% isopropanol/hexanes; enantiomer A, $t_R$=8.4 min; enantiomer B, $t_R$=10.5 min) to afford the separated enantiomers of D10 ($R^2=R^3=R^4=R^5=F$) $^1$H NMR (CDCl$_3$) δ 10.6 (m, 1H), 7.37 (m, 5H), 6.85 (m, 1H), 5.2 (m, 2H), 4.6-4.4 (m, 1H), 4.15 (m, 1H), 3.95 (m, 1H), 3.75 (m, 1H), 3.6 (m, 1H), 3.25 (m, 3H).

Method D, Step 10

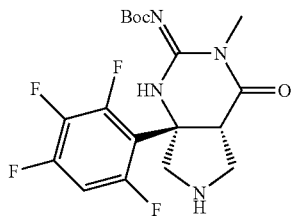

To a solution of D10 (enantiomer B, $t_R$=10.5 min., $R^2=R^3=R^4=R^5=F$, 350 mg) in MeOH (3 mL) was added of 20% Pd(OH)$_2$/C (150 mg) and the resulting suspension was stirred under an atmosphere of H$_2$ at rt for 3 hours. The reaction mixture was filtered through a pad of celite and the filtrate was evaporated to dryness to give D11 ($R^2=R^3=R^4=R^5=F$).

The following compound D12 was synthesized using methods similar to Method D:

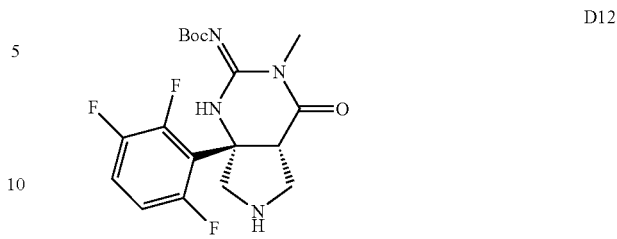

Alternative Method for the Synthesis of D6:

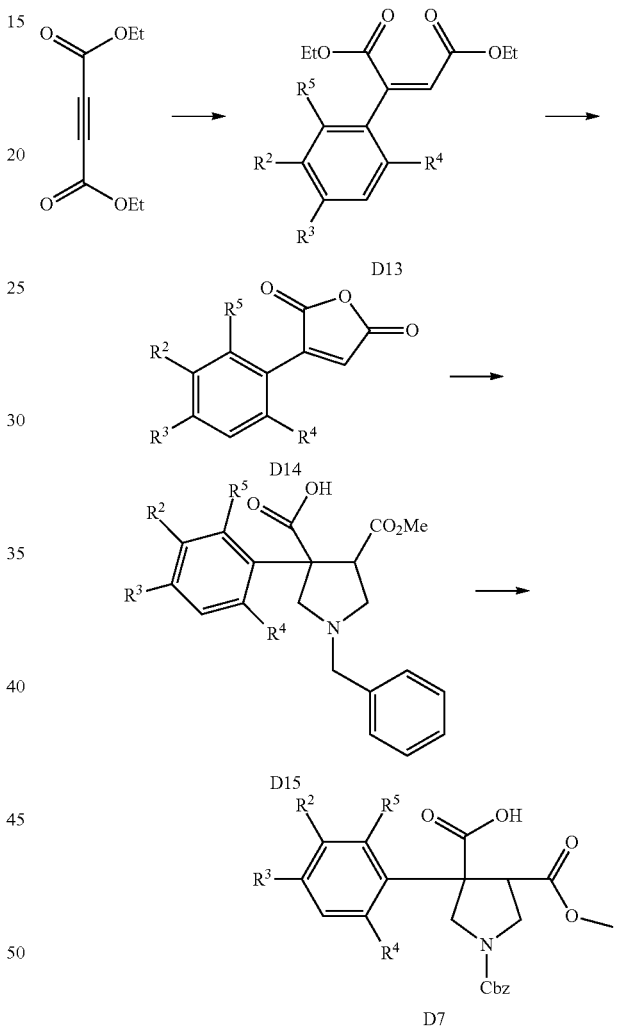

Alternative Method D, Step 1

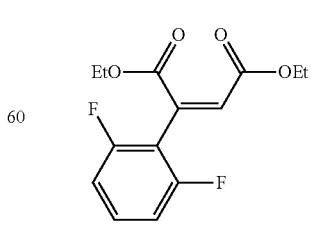

A flask was charged sequentially with diethylacetylene dicarboxylate (5.0 g, 29 mmol), 2,6-difluorophenylboronic acid (5.57 g, 35.3 mmol), 1,4-dioxane (90 mL), tetrakis(triphenylphosphine)palladium(0) (1.36 g, 1.18 mmol), and acetic acid (0.167 mL, 2.94 mmol). The resulting mixture was degassed by evacuation and back-fill with $N_2$ (3×) and was then immersed in an 80° C. oil bath. After 16 h, the reaction was diluted with water and EtOAc and stirred vigorously until both phases cleared. The phases were separated and the aqueous portion was extracted twice with EtOAc. The combined organic portions were washed with sat. aq. $NaHCO_3$ and brine, dried over $MgSO_4$, filtered and concentrated. The crude sample was subjected to column chromatography (330 g silica, 90 mL/min, 0% to 25% EtOAc/hexanes) to give D13 ($R^4=R^5=F$; $R^2=R^3=H$, 2.85 g, 34%).

$^1H$ NMR ($CDCl_3$): δ 7.32 (m, 1H) 6.94 (m, 2H), 6.45 (s, 1H), 4.30 (t, J=12.2 Hz, 2H) overlapping 4.26 (t, J=12.2 Hz, 2H), 1.32 (q, J=12.2 Hz, 3H) overlapping 1.30 (q, J=12.2 Hz, 3H).

Alternative Method D, Step 2.

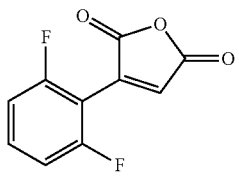 [SMILES: O=C1C=C(c2c(F)cccc2F)C(=O)O1]

A flask was charged with D13 ($R^4=R^5=F$; $R^2=R^3=H$, 1.34 g, 4.71 mmol), THF (100 mL), water (25 mL), and lithium hydroxide monohydrate (0.99 g, 24 mmol). The resulting mixture was immersed in a 40° C. oil bath and stirred vigorously. After 18 h at 40° C., the reaction was cooled, diluted with 1N HCl and EtOAc, and stirred vigorously until both phases cleared. The phases were separated and the aqueous portion was extracted twice with THF/EtOAc (1/3). The combined organic portions were washed with brine, dried over $MgSO_4$, filtered and concentrated.

The above crude material was dissolved in acetic anhydride (25 mL, 260 mmol) and immersed in a 90° C. oil bath. After 90 min, the mixture was concentrated to a semi-solid and azeotroped once with toluene (50 mL) to give product D14 ($R^4=R^5=F$; $R^2=R^3=H$, 1.0 g). $^1H$ NMR ($CDCl_3$): δ 7.53 (m, 1H), 7.09 (m, 3H).

Alternative Method D, Step 3.

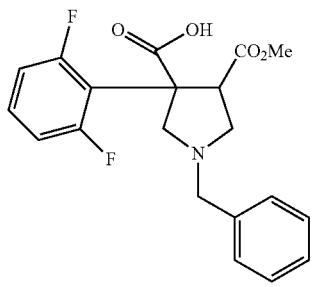 [SMILES: COC(=O)C1CN(Cc2ccccc2)CC1(Cc1c(F)cccc1F)C(=O)O]

To a 0° C. mixture of D14 ($R^4=R^5=F$; $R^2=R^3=H$, 37.8 g, 180 mmol) and THF (400 mL) was added N-benzyl-N-methoxymethyl-N-(trimethylsilyl)methylamine (64.5 mL, 252 mmol) and then trifluoroacetic acid (1.39 mL, 18.0 mmol). The cooling bath was removed and the mixture was allowed to stir. After 75 min, the reaction was immersed in a bath at −60° C., and a pre-mixed solution of triethylamine (50.2 mL, 360 mmol) in methanol (180 mL) was added via dropping funnel over 15 min. The resulting mixture was allowed to warm to RT and stir for 2.5 days. At that time, some solid had crashed out and was isolated by filtration with ether washes. The filtrate was partially concentrated causing additional solid to precipitate that was isolated by filtration. A third batch of solid was obtained by filtration after the mother liquor was allowed to stand for one week. The combined yield for the three crops of product D15 ($R^4=R^5=F$; $R^2=R^3=H$) was 48.4 g (56% as the triethylammonium salt). A portion of this material was converted to its HCl salt by treatment with 4N HCl/dioxane. MS: m/e=376.1 (M+H).

Alternative Method D, Step 4.

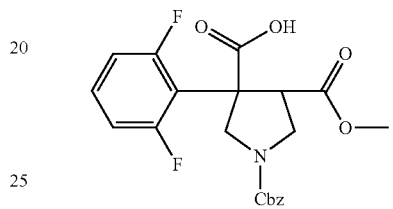

A mixture of D15 ($R^4=R^5=F$; $R^2=R^3=H$, 8.5 g, 18 mmol) and MeOH (250 mL) was treated with 4N HCl/dioxane (100 mL) and concentrated. The resulting residue was then re-dissolved in MeOH (250 mL) and 20% palladium hydroxide on carbon (4.0 g) was added in two batches. The mixture was stirred vigorously, and the flask was evacuated and back-filled with $H_2$ from a balloon (3×). The reaction was then kept under the $H_2$ balloon for 3 h. At that time, the flask was evacuated and back-filled with $N_2$ (2×), and the mixture was filtered through a Celite pad with copious MeOH washes. The filtrate was concentrated to give a crude product that was dissolved in THF (200 mL) and treated with triethylamine (6.2 mL, 44 mmol). Dioxane (100 mL) was added, followed by benzyl chloroformate (3.0 mL, 21 mmol). After 1 h, the reaction was diluted with 1N HCl and EtOAc and stirred vigorously until both phases cleared. The phases were separated and the aqueous portion was extracted with 1:1 THF:EtOAc (3×). The organic portions were combined, washed with brine, dried over $MgSO_4$, filtered, and concentrated. The crude sample was taken up in toluene (100 mL), re-concentrated, and subjected to column chromatography (330 g silica, 80 mL/min, 0% to 10% MeOH/DCM) to give D7 ($R^4=R^5=F$; $R^2=R^3=H$, 4.8 g, 64%). $^1H$ NMR ($CDCl_3$): δ 7.34 (m, 4H), 7.31 (m, 2H), 6.89 (m, 2H), 5.15 (dq, $J_q$=12.0 Hz, $J_d$=4.0 Hz, 2H), 4.63-4.51 (m, 1H), 3.98 (m, 2H), 3.86 (m, 1H), 3.77 (dd, J=16.0, 2.8 Hz, 1H), 3.71 (m, 3H).

The following compound was synthesized using similar methods to Alternative Method D: D16.

D16

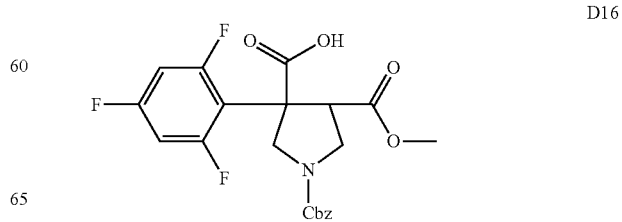

Method E

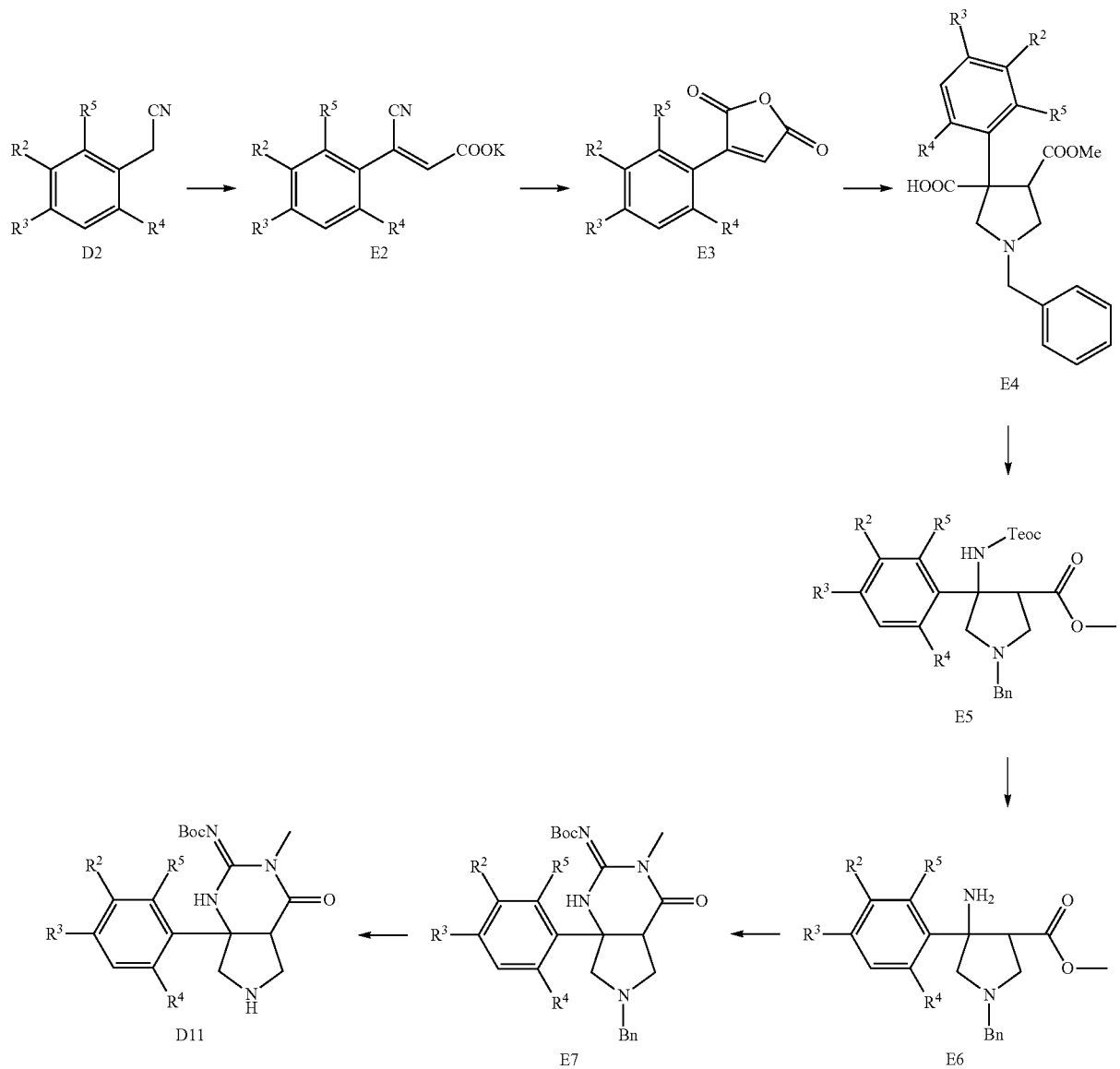

Method E, Step 1

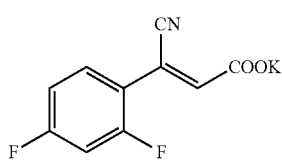

To a round bottom flask was added D2 (R²=R⁴=H, R³=R⁵=F, 75.0 g, 0.490 mol), MeOH (3 L) and glyoxylic acid (50 wt % in water, 81.8 mL, 1.5 equiv., 0.735 mol). The reaction mixture was then cooled in an ice-bath with stirring, and K$_2$CO$_3$ (169 g, 2.5 equiv., 1.2 mol) was added in portions. After the addition, the reaction mixture was heated to 70° C. and stirred overnight then allowed to cool to rt. The resulting white precipitate was collected by filtration and washed with cold water and MeOH to give E2 (R²=R⁴=H, R³=R⁵=F) as a white solid after drying in a vacuum oven (108 g, 89%). ¹H NMR (DMSO-d$_6$) δ 7.51 (m, 1H), 7.34 (m, 1H), 7.15 (m, 1H), 6.84 (s, 1H).

Method E, Step 2

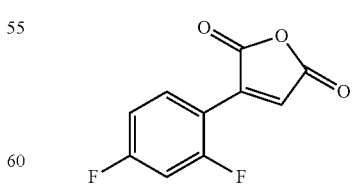

To a mixture of concentrated sulfuric acid (0.630 L) and 99% formic acid (8.37 L) at rt was added E2 (R²=R⁴=H, R³=R⁵=F; 1424 g, 5.76 mol) in several portions over 15 min. The resulting solution was heated at reflux for 3 h and allowed to cool to rt overnight. The precipitated solid was collected by vacuum filtration and re-dissolved in toluene (1.5 L). The resulting solution was concentrated under reduced pressure to provide E3 (R²=R⁴=H, R³=R⁵=F; 568 g, 47%) as a white solid. The filtrate from the reaction was then extracted with toluene (3×4 L) and the combined extracts concentrated under reduced pressure to afford additional E3 (R²=R⁴=H, R³=R⁵=F; 569 g, 47%) as a white solid. ¹H NMR (CDCl₃) δ 8.43 (m, 1H), 7.21 (d, 1H), 7.08 (m, 1H), 7.02 (m, 1H).
Method E, Step 3

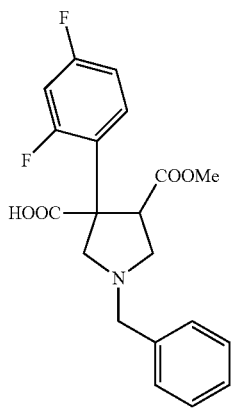 [SMILES: COC(=O)C1CN(Cc2ccccc2)CC1(C(=O)O)c1ccc(F)cc1F]

A solution of E3 (R²=R⁴=H, R³=R⁵=F; 252 g, 1.20 mol) in THF (800 mL) was cooled to 0-5° C. in an ice/brine bath and TFA (20 mL, 0.260 mol) was then added. A solution of N-(methoxymethyl)-N-(trimethylsilylmethyl)benzylamine (80% pure, 455 g, 1.50 mol) in THF (300 mL) was then added dropwise to the reaction flask over 2 h. The internal temperature was monitored and kept below 15° C. Upon completion of the addition, the cold bath was removed and the reaction was warmed to rt. The clear orange solution was stirred for 18 h and then the solvents were removed under reduced pressure. Methanol (1.10 L) was added and the reaction mixture was stirred overnight. After this time, the resultant solid was collected by vacuum filtration, washed with methanol (400 mL) and diethyl ether (500 mL) and dried to give E4 (R²=R⁴=H, R³=R⁵=F, 257 g, 57%) as an off-white solid. ¹H NMR (DMSO-d₆) δ 7.63 (m, 1H), 7.30-7.06 (m, 7H), 3.73 (m, 3H), 3.54 (s, 3H), 3.31 (m, 1H), 3.09 (m, 2H), 2.97 (m, 1H). MS m/e 376.11 (M⁺).
Method E, Step 4

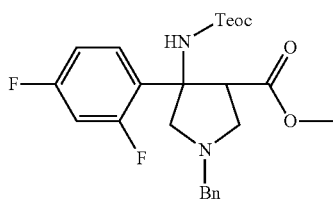

Triethylamine (67.4 g, 0.666 mol) was added to a stirred slurry of E4 (R²=R⁴=H, R³=R⁵=F; 250 g, 0.666 mol) in anhydrous toluene (2.22 L). The resulting suspension was stirred at rt for 10 min. After this time, DPPA (202 g, 0.733 mol) was added. The reaction mixture was then heated to about 63-66° C. and stirred at this temperature for 30 min. The reaction mixture was cooled to 40-50° C. and acetic acid (40.0 g, 0.666 mol) added, followed by addition of 2-(trimethylsilyl)ethanol (118 g, 0.998 mol). The resulting mixture was then heated to gentle reflux and stirred at gentle reflux overnight. The reaction mixture was cooled to rt and concentrated under reduced pressure. Ethyl acetate (1 L) was added to the residue and the suspension was washed with saturated aqueous sodium bicarbonate (2×800 mL). The combined aqueous layers were back extracted with ethyl acetate (400 mL). The combined organic layers were washed with brine (600 mL), dried over anhydrous sodium sulfate, filtered, and concentrated under reduced pressure. The resulting residue was purified by flash column chromatography (silica, 15% EtOAc/heptane) to afford E5 (R²=R⁴=H, R³=R⁵=F; 155 g, 48%) as a light yellow oil. ¹H NMR (CDCl₃) δ 7.56 (m, 1H), 7.32 (m, 5H), 6.82 (m, 3H), 4.08 (m, 2H), 3.76 (d, 2H), 3.71 (s, 3H), 3.61 (d, 1H), 3.40 (t, 1H), 3.36 (d, 1H), 3.01 (m, 2H), 0.98 (m, 1H), 0.02 (s, 9H). MS m/e 491.11 (M⁺).
Method E, Step 5

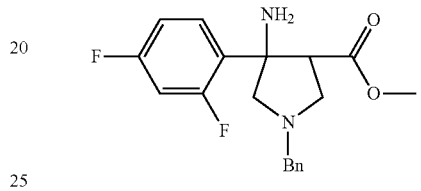

A 4 M HCl solution in 1,4-dioxane (313 mL, 1.25 mol) was added to E5 (R²=R⁴=H, R³=R⁵=F; 68.0 g, 0.139 mol). The resulting solution was stirred at rt overnight. After this time, the reaction mixture was concentrated under reduced pressure to a syrup and basified to pH 9 by slow addition of saturated aqueous sodium carbonate. The resulting suspension was extracted with ethyl acetate (4×300 mL). The combined extracts were dried over anhydrous sodium sulfate, filtered, and concentrated under reduced pressure. The residue was further dried under high vacuum for 30 min to give the crude amine E6 (R²=R⁴=H, R³=R⁵=F) that was used directly in the next step. ¹H NMR (CDCl₃) δ 7.31 (m, 1H), 7.43 (m, 5H), 7.90 (m, 2H), 6.19 (m, 1H), 4.43 (m, 2H), 4.17 (m, 2H), 4.00 (m, 2H), 3.71 (s, 3H).
Method E, Step 6

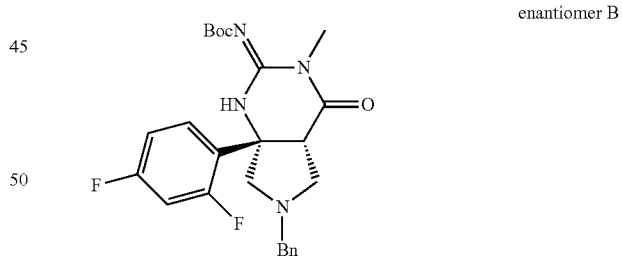

enantiomer B

To the solution of the crude amine E6 (R²=R⁴=H, R³=R⁵=F) obtained in Step 5 in anhydrous DMF (700 mL) was added N,N-diisopropylethylamine (97.0 mL, 0.556 mol), N-Boc-N'-methyl thiourea (33.6 g, 0.177 mol), and EDCl (42.4 g, 0.221 mol) and the reaction mixture stirred at 30° C. for 24 h. After this time, the reaction mixture was cooled to rt, diluted with ethyl acetate (1.5 L), and washed sequentially with water (4×800 mL) and brine (500 mL). The organic layer was dried over anhydrous sodium sulfate, filtered, and concentrated under reduced pressure. The residue was purified by flash column chromatography (silica gel, 15% ethyl acetate/heptane) to afford racemic E7 (R²=R⁴=H, R³=R⁵=F; 41.1 g, 63%) as a white solid. The enantiomers of racemic E7

($R^2=R^4=H$, $R^3=R^5=F$) were separated by chiral HPLC (20 μm Chiralpak AD column, 5 cm×50 cm (Chiral Technologies, Inc.) 40 mL/minute, 95% hexane/isopropanol; enantiomer A, $t_R$=34 min.; enantiomer B, $t_R$=65 min) to afford the separated enantiomers of E7 ($R^2=R^4=H$, $R^3=R^5=F$). $^1$H NMR (CDCl$_3$) δ 7.39 (m, 5H), 7.31 (m, 1H), 6.99 (m, 2H), 3.86 (s, 2H), 3.79 (t, 1H), 3.38 (s, 3H), 3.37 (m, 3H), 3.20 (m, 1H), 1.63 (s, 9H). MS m/e 471.11 (M$^+$).

Method E, Step 7

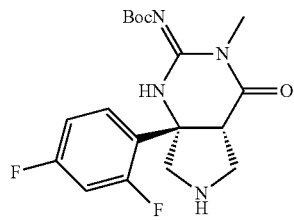

To a round bottom flask was added E7 (enantiomer B, $R^2=R^4=H$, $R^3=R^5=F$; 3.57 g, 7.44 mmol), 20% Pd(OH)$_2$/C (0.97 g) and MeOH (30 mL) and the mixture was degassed under vacuum and purged with N$_2$. The reaction mixture was stirred under an atmosphere of H$_2$ at it overnight and filtered through celite. The celite was washed with MeOH and the combined filtrate and washings were evaporated to give D11 ($R^2=R^4=H$, $R^3=R^5=F$; 2.63 g, 91%) which was used without further purification. $^1$H NMR (CDCl$_3$) δ 7.30 (m, 1H), 7.00 (m, 2H), 4.03 (m, 1H), 3.91 (m, 2H), 3.72 (m, 1H), 3.58 (m, 1H), 3.35 (s, 3H), δ 1.60 (s, 9H). MS m/e 381.21 (M$^+$).

The following compounds were synthesized using methods similar to Method E.

E8

E9

E10

-continued

E11

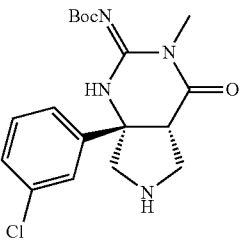

Method F

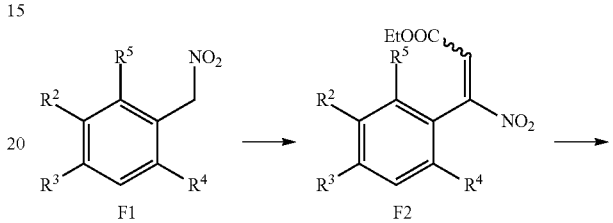

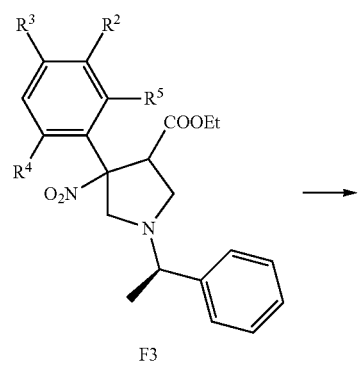

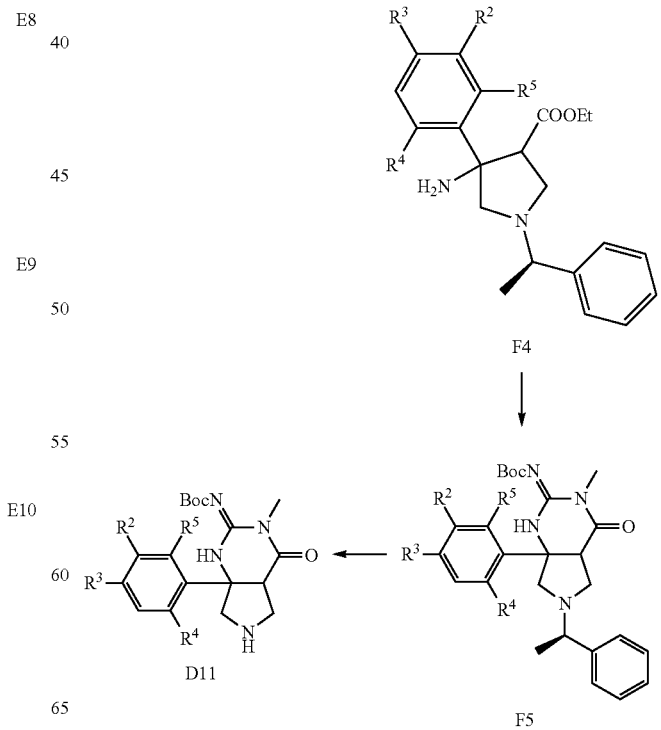

Method F, Step 1

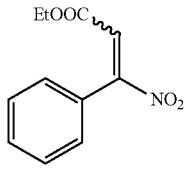 [SMILES: CCOC(=O)C=C(c1ccccc1)[N+](=O)[O-]]

To a round bottom flask was added (nitromethyl)benzene F1 ($R^2=R^3=R^4=R^5=H$, 3.93 g, 28.6 mmol), 50% ethyl glyoxylate/toluene (6.20 mL, 31.5 mmol), Amberlyst-21 (2.00 g) and THF (20 mL). The reaction mixture was stirred at rt for 18 hours and filtered. The filtrate was concentrated in vacuo and the resultant crude adduct (5.79 g, 85%) was used in the next step without further purification. To a round bottom flask containing the crude adduct (1.29 g, 5.41 mmol) was added $CH_3SO_2Cl$ (1.30 mL, 16.2 mmol), $Et_3N$ (2.30 mL, 16.2 mmol) and $CH_2Cl_2$ (20 mL) at −20° C. The reaction mixture was warmed to rt and stirred overnight, then poured into $H_2O$ and extracted with $CH_2Cl_2$ (3×100 mL). The combined organic layers were dried ($Na_2SO_4$), filtered and concentrated, and the residue was separated by slica chromatography (Analogix IntelliFlash 280, EtOAc/hexane) to afford F2 ($R^2=R^3=R^4=R^5=H$, Z isomer; 237 mg and E isomer; 676 mg, 56%) as white solids.

Method F, Step 2

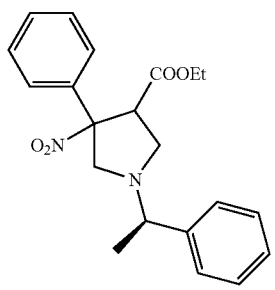 [SMILES: CCOC(=O)C1CN([C@H](C)c2ccccc2)CC1(c1ccccc1)[N+](=O)[O-]]

To a round bottom flask was added a mixture of F2 ($R^2=R^3=R^4=R^5=H$ as an E/Z mixture, 4.12 g, 18.3 mmol), (R)—N-(methoxymethyl)-N-(1-phenylethyl)-N-trimethylsilylmethylamine (5.61 g, 22.3 mmol) and $CH_2Cl_2$ (50 mL). The reaction mixture was then cooled to 0° C., and TFA (3.4 mL) was added dropwise. After the addition, the reaction was warmed to rt and stirred overnight. The reaction mixture was then concentrated in vacuo and partitioned between sat. aqueous $NaHCO_3$ and $CH_2Cl_2$. The organic layer was dried over $Na_2SO_4$, filtered and concentrated. The residue was purified by column silica gel chromatography (Analogix; EtOAc/hexane; 0-50%) to give F3 ($R^2=R^3=R^4=R^5=H$) as a colorless oil (5.67 g, 84%).

Method F, Step 3

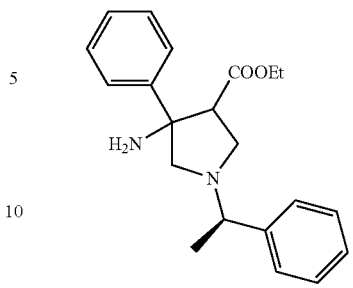

To a round bottom flask was added F3 ($R^2=R^3=R^4=R^5=H$, 5.67 g, 15.4 mmol), MeOH (200 mL), and $NiCl_2 \cdot 6H_2O$ (7.32 g, 30.8 mmol). To the stirred mixture cooled to 0° C. was added $NaBH_4$ (2.33 g, 61.6 mmol) in portions. The reaction mixture was stirred at 0° C. for 35 minutes, and additional $NiCl_2 \cdot 6H_2O$ (3.66 g) and $NaBH_4$ (1.67 g) were added. The reaction mixture was stirred for 20 minutes, poured into cold $H_2O$ (~100 mL) and filtered through celite. The filter pad was washed with $CH_2Cl_2$. The aqueous layer was extracted with $CH_2Cl_2$ (3×100 mL) and the combined organic layers were dried over $Na_2SO_4$, filtered and concentrated to give F4 ($R^2=R^3=R^4=R^5=H$, 3.67 g) which was used in the next step without further purification.

Method F, Step 4

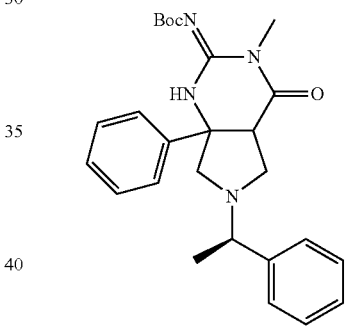

To a round bottom flask was added crude F4 ($R^2=R^3=R^4=R^5=H$, 3.67 g), N-Boc-N'-methylthiourea (2.27 g, 11.9 mmol), EDCl (3.11 g, 16.2 mmol), DIEA (5.6 mL, 32.4 mmol) and DMF (50 mL). The reaction mixture was stirred at rt for about 4 days and poured into cold water (100 mL). The aqueous layer was extracted with $CH_2Cl_2$ (3×100 mL) and the combined organic layers were dried over $Na_2SO_4$ filtered, and evaporated. The residue was separated by silica gel column chromatography (Analogix, EtOAc/Hexane=0-20%) to give F5 ($R^2=R^3=R^4=R^5=H$, 440 mg, 0.98 mmol, 6.4% for two steps).

Method F, Step 5

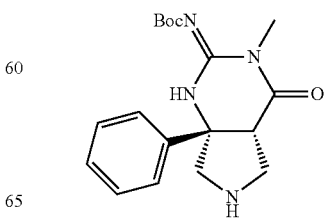

Following a method similar to Method E, Step 7, compound D11 ($R^2=R^3=R^4=R^5=H$) was obtained from compound F5 ($R^2=R^3=R^4=R^5=H$).

Method G

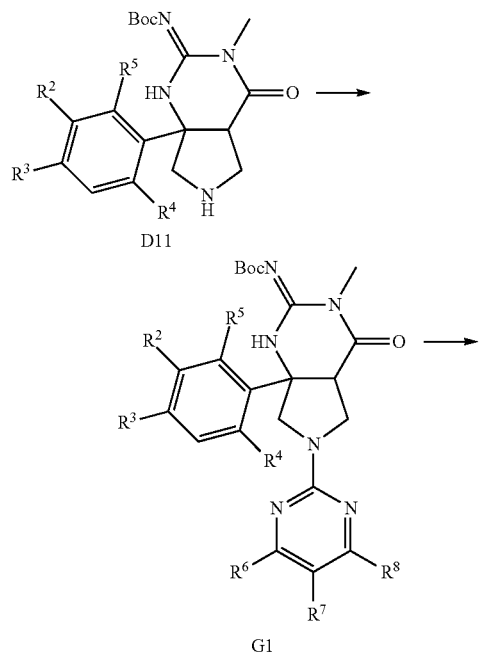

Method G, Step 1

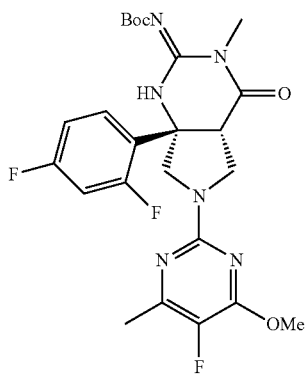

To a flame-dried and $N_2$ purged flask was added A3 ($R^6$=OMe, $R^7$=F, $R^8$=Me; 765 mg, 4.33 mmol), 2'-(di-tert-butylphosphino)-N,N-dimethylbiphenyl-2-amine (63 mg, 0.18 mmol), Pd(OAc)$_2$ (37 mg, 0.167 mmol) and sodium tert-butoxide (705 mg, 7.33 mmol) in one portion. Then a solution of D11 ($R^2=R^4$=H, $R^3=R^5$=F; prepared from E7, enantiomer B (Method E); 1.27 g, 3.33 mmol) in anhydrous toluene (10 mL) was added. The reaction mixture was heated at 100° C. in an oil bath with stirring for 30 min then cooled to rt. The reaction mixture was diluted with $CH_2Cl_2$ (100 mL) and acidified with 5% aqueous citric acid. The aqueous layer was extracted with $CH_2Cl_2$ (50 mL). The combined organic layers were washed with satd. aqueous $NaHCO_3$ and brine, dried ($MgSO_4$), filtered and concentrated. The crude mixture was purified by silica gel chromatography (hexane, then 0-15% EtOAc/hexane) to afford the product G1 ($R^2=R^4$=H, $R^3=R^5$=F, $R^6$=OMe, $R^7$=F, $R^8$=Me 1.30 g, 75%).

Method G, Step 2:

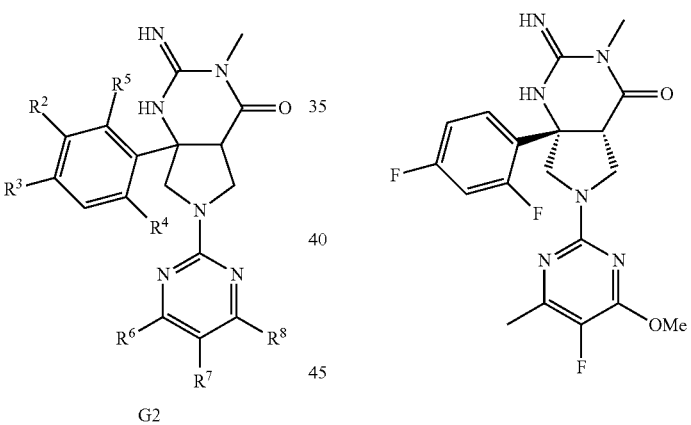

Example 1

A mixture of G1 ($R^2=R^4$=H, $R^3=R^5$=F, $R^6$=OMe, $R^7$=F and $R^8$=Me, 634 mg) and 20% TFA/$CH_2Cl_2$ (10 mL) was stirred at rt for 4 hours and then concentrated in vacuo. The concentrated residue was purified by HPLC(C18 column, MeCN/$H_2O$ (with 0.1% HCOOH) gradient from 10-90%, 35 mL/min) to give G2 ($R^2=R^4$=H, $R^3=R^5$=F, $R^6$=OMe, $R^7$=F, $R^8$=Me; Example 1, 566 mg, 78% yield) as the formate salt. $^1$H NMR (CDCl$_3$) δ 7.35 (m, 1H), 6.92 (m, 2H), 4.50 (d, 1H, J=12.4 Hz), 4.28 (t, 1H, J=10.4 Hz), 4.02 (m, 2H), 3.96 (s, 3H), 3.81 (t, 1H, J=10.8 Hz), δ 3.34 (s, 3H), δ 2.29 (d, 3H, J=2.8 Hz). MS m/e 421.12 (M$^+$).

Method H
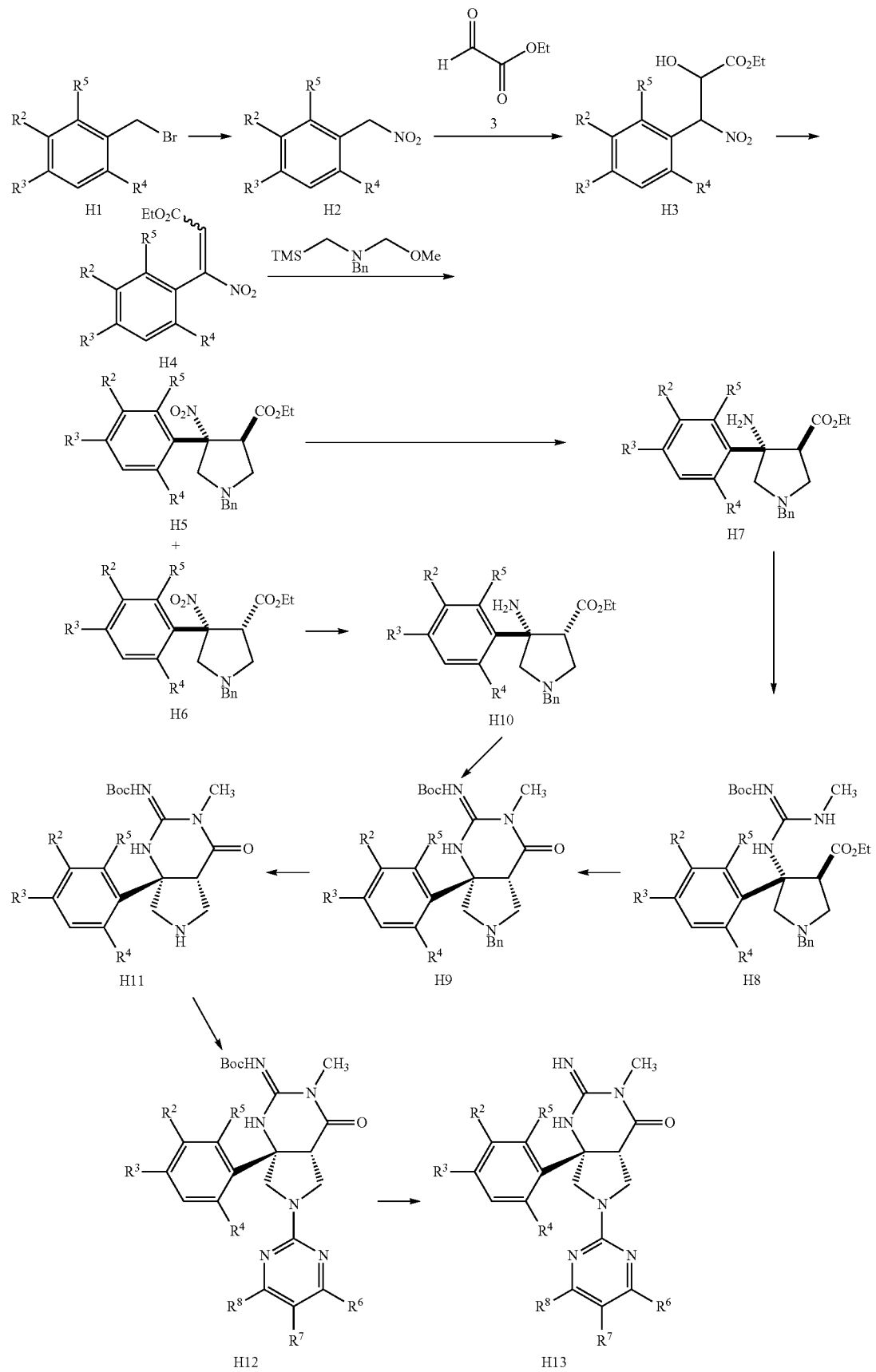

Method H, Step 1

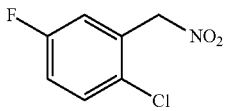

A solution of H1 ($R^2$=F, $R^4$=Cl, $R^3$=$R^5$=H, 29.9 g, 134 mmol) in diethyl ether (55 mL) was added dropwise via an addition funnel to a stirred slurry of silver nitrite (35.0 g, 227 mmol) in diethyl ether (130 mL) at 0° C. After addition was complete, the mixture was stirred at 0° C. to rt over 1 h, and then at rt for 18 h. The mixture was filtered and the filtrate was concentrated. The residue was purified by column chromatography (silica, 0-15% EtOAc/heptane) to afford H2 ($R^2$=F, $R^4$=Cl, $R^3$=$R^5$=H, 19.5 g, 77%) as a colorless oil: $^1$H NMR (300 MHz, CDCl$_3$) δ 7.46 (dd, J=8.7, 5.0 Hz, 1H), 7.21-7.11 (m, 2H), 5.57 (s, 2H).

Method H, Step 2

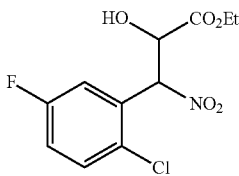 [SMILES: CCOC(=O)C(O)C(c1cc(F)ccc1Cl)[N+](=O)[O-]]

To a solution of ethyl glyoxalate (50% in toluene, 40 mL, 202 mmol) and H2 ($R^2$=F, $R^4$=Cl, $R^3$=$R^5$=H, 19.2 g, 101 mmol) was added Amberlyst A-21 (15 g) at 0° C. The mixture was stirred at 0° C. for 20 min and then at rt for 18 h. After this time, the mixture was filtered and the filtrate concentrated. The residue was purified by column chromatography (silica, 0-50% EtOAc/heptane) to afford H3 ($R^2$=F, $R^4$=Cl, $R^3$=$R^5$=H, 24.4 g, 83%, 5:3 mixture of isomers) as a colorless oil.

Major isomer: $^1$H NMR (300 MHz, CDCl$_3$) δ 7.58-7.39 (m, 2H), 7.17-7.11 (m, 1H), 6.42 (d, J=3.0 Hz, 1H), 4.68 (dd, J=5.3, 3.2 Hz, 1H), 4.40-4.21 (m, 2H), 3.58 (d, J=5.3 Hz, 1H), 1.33-1.21 (m, 3H).

Minor isomer: $^1$H NMR (300 MHz, CDCl$_3$) δ 7.58-7.39 (m, 2H), 7.17-7.11 (m, 1H), 6.37 (d, J=3.7 Hz, 1H), 5.29 (t, J=4.3 Hz, 1H), 4.40-4.21 (m, 2H), 3.35 (d, J=4.4 Hz, 1H), 1.33-1.21 (m, 3H).

Method H, Step 3

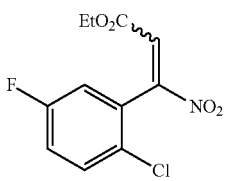 [SMILES: CCOC(=O)C=C(c1cc(F)ccc1Cl)[N+](=O)[O-]]

Trifluoromethanesulfonyl chloride (7.81 g, 68.2 mmol) was added to a solution of H3 ($R^2$=F, $R^4$=Cl, $R^3$=$R^5$=H, 18.0 g, 61.7 mmol) in methylene chloride (140 mL) at −5° C., followed by dropwise addition of a solution of triethylamine (26.0 mL, 187 mmol) in methylene chloride (20 mL) over 30 min. The mixture was stirred at −5° C. for 1 h and it was poured slowly into ice water (400 mL) and then extracted with methylene chloride (250 mL). The organic layer was washed with 1 N hydrochloric acid (2×200 mL) and brine (200 mL), dried (Na$_2$SO$_4$), filtered, and concentrated to afford H4 ($R^2$=F, $R^4$=Cl, $R^3$=$R^5$=H, 12.9 g, 76%) as a yellow oil that was used in the next step without further purification: $^1$H NMR (300 MHz, CDCl$_3$) δ 7.48-7.43 (m, 2H), 7.19 (ddd, J=16.6, 7.8, 3.0 Hz, 1H), 7.07 (dd, J=8.0, 3.0 Hz, 1H), 4.15 (q, J=7.1 Hz, 2H), 1.16 (t, J=7.1 Hz, 3H).

Method H, Step 4

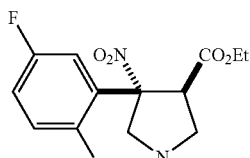

H5

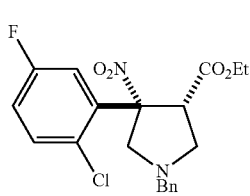

H6

N-benzyl-1-methoxy-N-[(trimethylsilyl)methyl]methanamine (~80%, 16.0 g, 54.0 mmol) was added to a solution of H4 ($R^2$=F, $R^4$=Cl, $R^3$=$R^5$=H, 12.0 g, 43.9 mmol) in THF (90 mL) at 0° C. followed by dropwise addition of a solution of TFA (0.90 mL, 12.1 mmol) in THF (10 mL) over 15 min. The mixture was stirred at 0° C. for 20 min and then at rt for 18 h. After this time, saturated sodium bicarbonate (200 mL) was added and the mixture was extracted with EtOAc (200 mL). The organic layer was dried (Na$_2$SO$_4$), filtered, and concentrated. The residue was purified by column chromatography (silica, 0-30% EtOAc/heptane) to afford H5 ($R^2$=F, $R^4$=Cl, $R^3$=$R^5$=H; yellow solid, 6.25 g, 36%) and H6 ($R^2$=F, $R^4$=Cl, $R^3$=$R^5$=H; yellow oil, 5.62 g, 32%).

H5: $^1$H NMR (300 MHz, CDCl$_3$) δ 7.35-7.17 (m, 6H), 7.15 (dd, J=9.5, 2.9 Hz, 1H), 7.04 (ddd, J=16.0, 7.2, 2.9 Hz, 1H), 4.91 (ddd, J=13.6, 4.9, 1.4 Hz, 1H), 3.86 (q, J=7.1 Hz, 2H), 2.81-3.78 (m, 3H), 3.66 (t, J=9.0 Hz, 1H), 3.55 (d, J=9.7 Hz, 1H), 2.74 (dd, J=9.3, 4.9 Hz, 1H), 0.96 (t, J=7.1 Hz, 3H).

H6: $^1$H NMR (300 MHz, CDCl$_3$) δ 7.70 (dd, J=10.1, 2.8 Hz, 1H), 7.40-7.20 (m, 6H), 7.07 (ddd, J=16.0, 7.2, 2.9 Hz, 1H), 4.26-4.12 (m, 3H), 4.01 (dd, J=10.9, 6.8 Hz, 1H), 3.91 (d, J=12.8 Hz, 1H), 3.85 (d, J=12.8 Hz, 1H), 3.59 (d, J=12.4 Hz, 1H), 3.34-3.20 (m, 2H), 1.22 (t, J=7.2 Hz, 3H).

Method H, Step 5

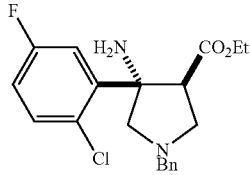

A solution of H5 ($R^2$=F, $R^4$=Cl, $R^3$=$R^5$=H, 3.40 g, 8.30 mmol) in 1,4-dioxane (3 mL) and ethanol (60 mL) was subjected to hydrogenation conditions (H$_2$, 40 psi) over Raney nickel (slurry in H$_2$O, washed with ethanol before use, 2.0 g) for 2.5 h. The mixture was filtered and the filtrate was concentrated. The residue was purified by column chromatography [silica, 3-95% EtOAc (with 1% Et$_3$N)/heptane] to afford H7 ($R^2$=F, $R^4$=Cl, $R^3$=$R^5$=H, 2.70 g, 87%) as a colorless oil: $^1$H NMR (300 MHz, CDCl$_3$) δ 7.40-7.24 (m, 6H), 6.94-6.85 (m, 2H), 3.90-3.76 (m, 4H), 3.72 (dd, J=8.0, 5.0 Hz, 1H), 3.50 (t, J=9.1 Hz, 1H), 3.25 (d, J=8.0 Hz, 1H), 3.08 (d, J=8.0 Hz, 1H), 2.67-2.60 (m, 3H), 0.92 (t, J=7.1 Hz, 3H).
Method H, Step 6

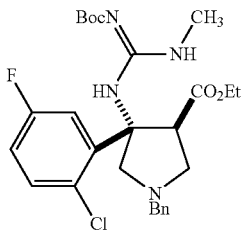

To a solution of H7 ($R^2$=F, $R^4$=Cl, $R^3$=$R^5$=H, 3.15 g, 8.36 mmol) and N,N-diisopropylethylamine (4.4 mL, 25.2 mmol) in DMF (70 mL) was added N-Boc-N'-methylthiourea (3.20 g, 16.8 mmol), followed by 1-(3-dimethylaminopropyl)-3-ethylcarbodiimide hydrochloride (4.80 g, 25.0 mmol). The mixture was stirred at rt for 18 h. After this time, the reaction mixture was diluted with EtOAc (300 mL) and washed with 5% LiCl aqueous solution (3×200 mL). The organic layer was dried over magnesium sulfate, filtered and concentrated under reduced pressure. The residue was purified by column chromatography (silica, 0-50% EtOAc/heptane) to afford H8 ($R^2$=F, $R^4$=Cl, $R^3$=$R^5$=H, 4.00 g, 90%) as a white solid: ESI MS m/z 533 [M+H]$^+$.
Method H, Step 7

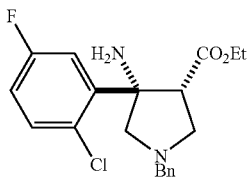

To a solution of H6 ($R^2$=F, $R^4$=Cl, $R^3$=$R^5$=H, 5.28 g, 13.0 mmol) in isopropanol (120 mL) at 0° C. was added 2 N hydrochloric acid (70 mL) followed by zinc dust (14.0 g, 214 mmol) in small portions and the mixture was stirred at rt for 3 h. After this time, the reaction was quenched by slow addition of saturated aqueous sodium bicarbonate (200 mL) and EtOAc (300 mL). The mixture was stirred at rt for 15 min and then the organic layer was separated and washed with brine (200 mL), dried (MgSO$_4$), filtered, and concentrated to afford H10 ($R^2$=F, $R^4$=Cl, $R^3$=$R^5$=H, 3.70 g) as a pale yellow oil, that was used in the next step without further purification: ESI MS m/z 377 [M+H]$^+$.
Method H, Step 8

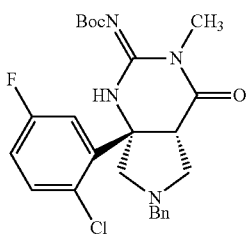

To a solution of compound H8 ($R^2$=F, $R^4$=Cl, $R^3$=$R^5$=H, 4.00 g, 7.50 mmol) in THF (120 mL) at 0° C. was added potassium tert-butoxide (1.60 g, 14.3 mmol) and the mixture was stirred at 0° C. for 30 min. After this time, brine (200 mL) was added and the mixture was extracted with EtOAc (3×200 mL). The organic layer was dried (Na$_2$SO$_4$), filtered, and concentrated under reduced pressure. The residue was purified by column chromatography (silica, 0-50% EtOAc/heptane) to afford the product as a racemic mixture (2.40 g, 66%). Chiral separation on a preparative Chiralpak AD column (eluent: 99:1 heptane/isopropanol with 0.1% diethylamine) afforded the product enantiomer H9 ($R^2$=F, $R^4$=Cl, $R^3$=$R^5$=H, 0.930 g, 25%) as a white solid: $^1$H NMR (300 MHz, CDCl$_3$) δ 10.54 (s, 1H), 7.38 (dd, J=8.7, 5.3 Hz, 1H), 7.34-7.28 (m, 5H), 7.06-6.96 (m, 2H), 3.84-3.71 (m, 3H), 3.53 (d, J=10.7 Hz, 1H), 3.38 (t, J=8.7 Hz, 1H), 3.30 (s, 3H), 3.25 (d, J=10.7 Hz, 1H), 2.98 (t, J=8.7 Hz, 1H), 1.52 (s, 9H).

Alternatively, racemic product H9 ($R^2$=F, $R^4$=Cl, $R^3$=$R^5$=H, 1.20 g, 26%) was prepared starting from H10, using the same procedure described in method H, Step 6.
Method H, Step 9

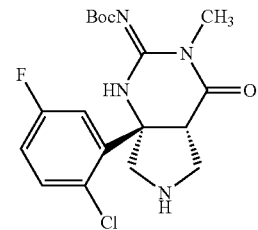

To a mixture of enantiomer H9 ($R^2$=F, $R^4$=Cl, $R^3$=$R^5$=H, 1.41 g, 2.90 mmol) from Step 8 and potassium carbonate (2.00 g, 14.5 mmol) in 1,2-dichloroethane (60 mL) at 0° C. was added 1-chloroethyl chloroformate (2.60 mL, 23.9 mmol). The mixture was stirred at 0° C. for 5 min and then at reflux for 30 min. After this time, the mixture was concentrated to dryness and the residue was dissolved in methanol (50 mL). Benzylamine (2.60 mL, 23.8 mmol) was added and the mixture was stirred at reflux for 35 min. The reaction mixture was cooled to it and concentrated. The residue was purified by column chromatography [silica, 0-30% (80:18:2 CH$_2$Cl$_2$/MeOH/NH$_4$OH)/CH$_2$Cl$_2$] to afford H11 ($R^2$=F, $R^4$=Cl, $R^3$=$R^5$=H, 0.395 g, 34%) as a white solid: $^1$H NMR (300 MHz, CDCl$_3$) δ 10.57 (s, 1H), 7.41 (dd, J=8.7, 4.3 Hz, 1H), 7.09-6.97 (m, 2H), 3.87-3.66 (m, 3H), 3.55 (d, J=12.7 Hz, 1H), 3.34-3.27 (m, 4H), 2.22 (br s, 1H), 1.53 (s, 9H).
Method H, Step 10

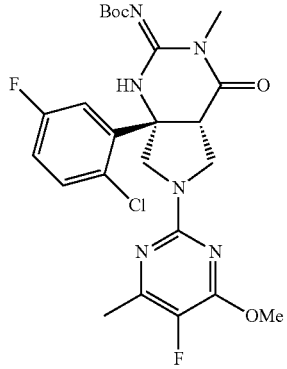

To a solution of H11 ($R^2$=F, $R^4$=Cl, $R^3$=$R^5$=H, 0.390 g, 0.980 mmol) in toluene (10 mL) previously purged with nitrogen was added A3 ($R^6$=MeO, $R^7$=F and $R^8$=Me; 0.230 g, 1.30 mmol), 2'-(di-tert-butylphosphino)-N,N-dimethylbiphenyl-2-amine (0.020 g, 0.113 mmol), sodium tert-butoxide (0.250 g, 2.60 mmol), and palladium(II) acetate (0.033 g, 0.050 mmol). The mixture was stirred at 100° C. for 40 min.

After this time, the reaction mixture was cooled to rt and partitioned between water (30 mL) and methylene chloride (60 mL). The organic layer was dried (MgSO$_4$), filtered, and concentrated. The residue was purified by column chromatography (silica, 0-50% EtOAc/heptane) to afford H12 (R$^2$=F, R$^4$=Cl, R$^3$=R$^5$=H, R$^6$=MeO, R$^7$=F and R$^8$=Me; 0.226 g, 43%) as an off-white solid: $^1$H NMR (300 MHz, CDCl$_3$) δ 10.70 (s, 1H), 7.44 (dd, J=9.6, 2.8 Hz, 1H), 7.08-7.02 (m, 2H), 4.53 (d, J=12.5 Hz, 1H), 4.29 (dd, J=10.5, 8.8 Hz, 1H), 4.13-4.02 (m, 2H), 3.97 (s, 3H), 3.78 (t, J=10.0 Hz, 1H), 3.29 (s, 3H), 2.30 (d, J=2.8 Hz, 3H), 1.51 (d, 9H).

Method H, Step 11

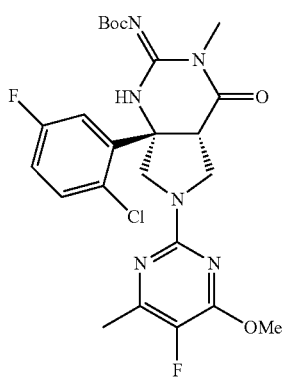

Example 2

Trifluoroacetic acid (8 mL) was added to a solution of H12 (R$^2$=F, R$^4$=Cl, R$^3$=R$^5$=H, R$^6$=MeO, R$^7$=F and R$^8$=Me 0.200 g, 0.372 mmol) in methylene chloride (8 mL) and the reaction mixture stirred at rt for 40 min. After this time, the mixture was concentrated to dryness. The residue was purified by preparative HPLC (Waters Symmetry C18 7 μm (19×300 mm) column; gradient 10% MeCN/H$_2$O containing 0.025% HCl-100% MeCN) and then lyophilized from water/acetonitrile to afford H13 (Example 2, R$^2$=F, R$^4$=Cl, R$^3$=R$^5$=H, R$^6$=MeO, R$^7$=F and R$^8$=Me; 0.145 g, 83%) as a white solid: [α]$^{25}_D$=-71.2° (c 0.480, MeOH); $^1$H NMR (500 MHz, DMSO-d$_6$) δ 10.78 (s, 1H), 9.13 (br s, 2H), 7.67 (s, 1H), 7.39 (s, 1H), 7.18 (d, J=8.7 Hz, 1H), 4.48-4.42 (m, 2H), 4.05-3.94 (m, 6H), 3.18 (s, 3H), 2.26 (s, 3H); ESI MS m/z 437 [M+H]$^+$.

Method I
Preparation of

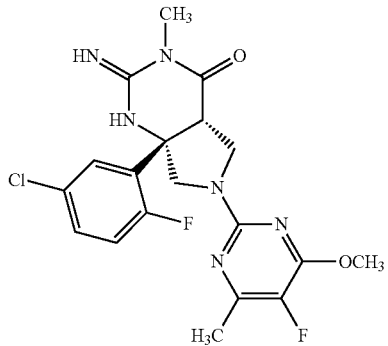 [SMILES: COc1nc(N2C[C@H]3C(=O)N(C)C(=N)N[C@@]3(c3cc(Cl)ccc3F)C2)nc(C)c1F]

Method I, Step 1

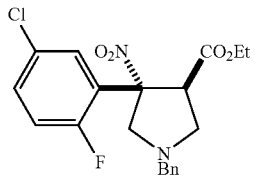

Compound H5 (R$^2$=Cl, R$^4$=F, R$^3$=R$^5$=H) was prepared by essentially the same procedure described in Method H, Steps 1-4.

$^1$H NMR (300 MHz, CDCl$_3$) δ 7.35-7.26 (m, 7H), 7.03-6.98 (m, 1H), 4.72-4.69 (m, 1H), 3.96-3.80 (m, 5H), 3.57-3.45 (m, 2H), 2.81-2.77 (m, 1H), 1.00-0.90 (m, 3H).

Method I, Step 2

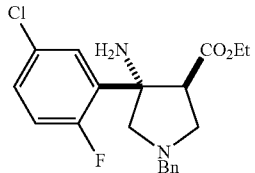

To a solution of H5 (R$^2$=Cl, R$^4$=F, R$^3$=R$^5$=H, 4.13 g, 10.2 mmol) in ethanol (300 mL) was added concentrated hydrochloric acid (8.5 mL) and iron powder (5.70 g). The reaction mixture was stirred at reflux for 2 h. After this time, the mixture was cooled to rt and then filtered through a pad of Celite. The filtrate was concentrated under reduced pressure. To the residue was added EtOAc (250 mL) and 1 N aqueous NaOH solution (600 mL) and the mixture was filtered through a second pad of Celite. The organic layer was separated and the aqueous layer was extracted with EtOAc (2×500 mL). The combined organic extracts were dried (Na$_2$SO$_4$), filtered, and concentrated under reduced pressure to obtain H7 (R$^2$=Cl, R$^4$=F, R$^3$=R$^5$=H, 3.48 g, 91%) as a yellow oil: $^1$H NMR (300 MHz, CDCl$_3$) δ 7.41-7.29 (m, 5H), 7.20-7.16 (m, 2H), 6.99-6.93 (m, 1H), 3.83 (d, J=5.7 Hz, 2H), 3.80-3.71 (m, 2H), 3.47-3.35 (m, 2H), 3.18 (d, J=8.4 Hz, 1H), 3.03 (d, J=8.4 Hz, 1H), 2.74 (dd, J=9.0, 4.5 Hz, 1H), 2.33 (br s, 2H), 0.90 (t, J=7.2 Hz, 3H); ESI MS m/z 377 [M+H].

Method I, Step 3

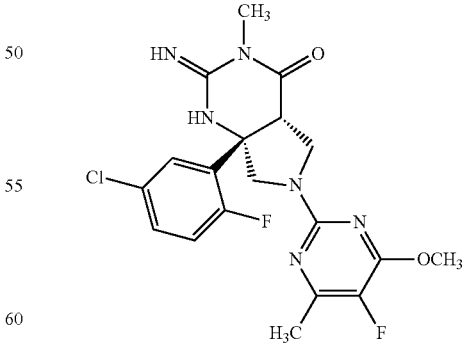

Example 3

Compound H7 (R$^2$=Cl, R$^4$=F, R$^3$=R$^5$=H) was converted to racemic H12 (R$^2$=Cl, R$^4$=F, R$^3$=R$^5$=H, R$^6$=MeO, R$^7$=F and R[8]=Me) by essentially the procedures described in Method H, Steps 6, 8, 9 and 10. $^1$H NMR (300 MHz, CDCl$_3$) δ 10.44 (br s, 1H), 7.37-7.32 (m, 1H), 7.23 (dd, J=6.6, 2.4 Hz, 1H), 7.14-7.07 (m, 1H), 4.35-4.26 (m, 2H), 3.99 (s, 3H), 3.96-3.94 (m, 2H), 3.77 (t, J=10.5 Hz, 1H), 3.30 (s, 3H), 2.29 (d, J=2.7 Hz, 3H), 1.52 (s, 9H). Chiral separation (Chiralpak AD, 90:10 heptane/isopropanol) of H12 (R$^2$=Cl, R$^4$=F, R$^3$=R$^5$=H, R$^6$=MeO, R$^7$=F and R$^8$=Me) was followed by deprotection according to Method H, Step 11 to give H13 (Example 3, R$^2$=Cl, R$^4$=F, R$^3$=R$^5$=H, R$^6$=MeO, R$^7$=F and R$^8$=Me).

$[\alpha]^{23}_D$=-61.3° (c, 0.400, methanol); $^1$H NMR (500 MHz, DMSO-d$_6$) δ 10.68 (s, 1H), 8.91 (br s, 2H), 7.61-7.58 (m, 1H), 7.44-7.37 (m, 2H), 4.45 (d, J=12.0 Hz, 1H), 4.26-3.85 (m, 1H), 4.16-3.85 (m, 6H), 3.18 (s, 3H), 2.26 (s, 3H); ESI MS m/z 437 [M+H]$^+$.

Method J

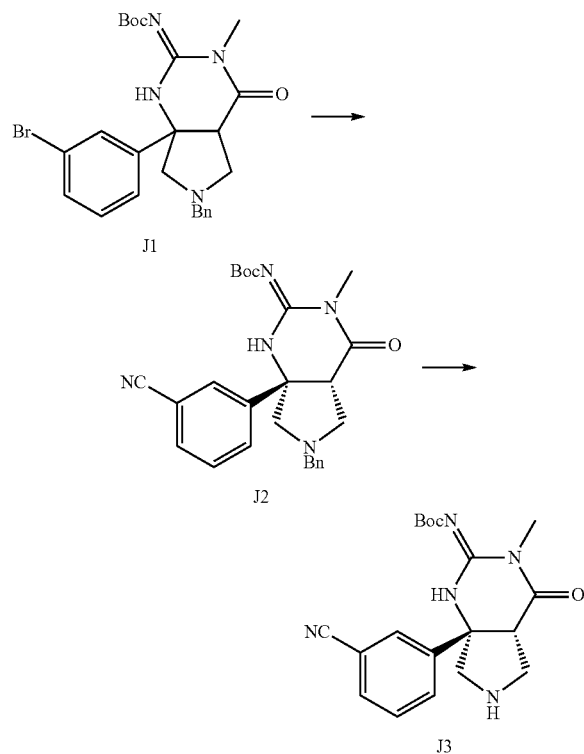

Method J, Step 1

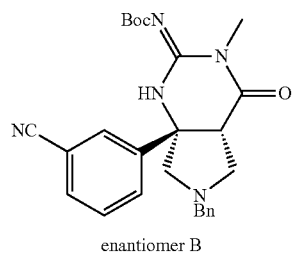

enantiomer B

DMA (25 mL) was added to a mixture of J1 (obtained using methods similar to Method E, Steps 1-6; 2.96 g, 5.76 mmol), PdCl$_2$dppf (817 mg, 1.00 mmol), zinc powder (300 mg, 4.61 mmol) and zinc cyanide (541 mg, 4.61 mmol), followed by three cycles of vacuum/nitrogen to degas. The reaction vessel was stirred for 2.5 hours at 85° C., then cooled to rt and filtered. The filtrate was diluted with EtOAc and saturated aqueous NaHCO$_3$, and the organic layer washed with water (1×) and brine (1×), dried over MgSO$_4$ and concentrated under reduced pressure. The resulting oil was subjected to silica gel chromatography (120 g SiO$_2$, 254 nm detection, 0→25% EtOAc/hexanes) to give racemic J2 as a white foam (1.35 g, 2.94 mmol, 51%). J2 was subjected to chiral HPLC (Chiracel AD column; 5 cm ID×50 cm, 75 mL/min 5% IPA/hexanes (isocratic), monitored at 220 nm and 254 nm) to give enantiomer A (t$_R$=17.4 min) and the desired enantiomer B (t$_R$=23.7 min).

Method J, Step 2

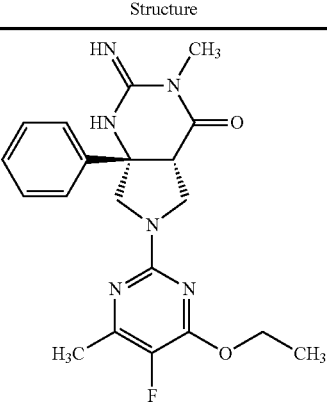

The product of Step 1, J2 (enantiomer B) was converted to J3 by essentially the procedure described in Method H, Step 9.

The following compounds were synthesized using the appropriate intermediates and essentially the procedures described in Methods A-J and Examples 1-3. All compounds are single enantiomers of absolute configuration shown, unless otherwise indicated as racemic.

| Ex | Structure | Obs. Mass |
|---|---|---|
| 4 racemic | 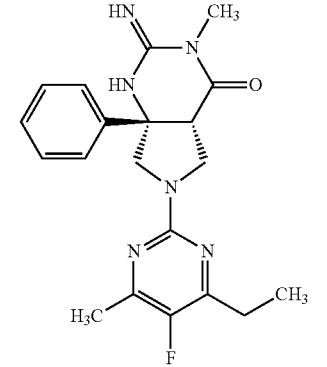 | 399.22 |
| 5 racemic | 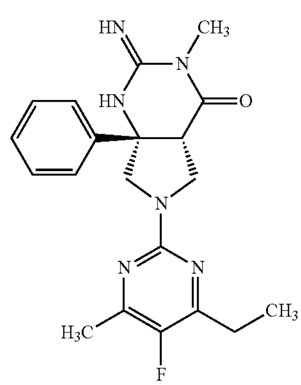 [SMILES: CCc1nc(N2C[C@H]3C(=O)N(C)C(=N)N[C@@]3(c3ccccc3)C2)nc(C)c1F] | 383.21 |

-continued

| Ex | Structure | Obs. Mass |
|---|---|---|
| 6 racemic | 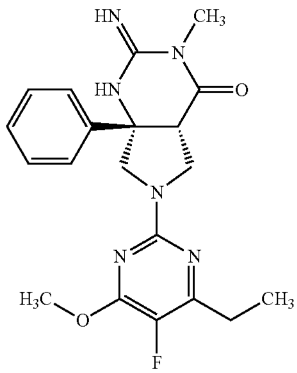 [SMILES: CCc1nc(N2C[C@H]3C(=O)N(C)C(=N)N[C@@]3(c3ccccc3)C2)nc(OC)c1F] | 399.22 |
| 7 racemic | 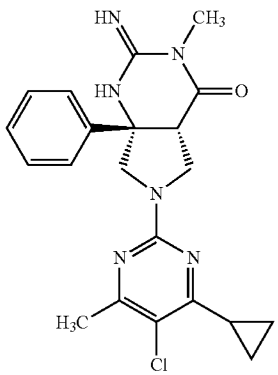 | 411.23 |
| 8 | 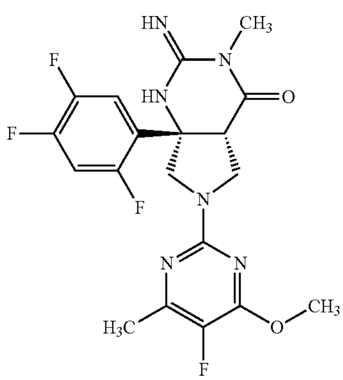 [SMILES: COc1nc(N2C[C@H]3C(=O)N(C)C(=N)N[C@@]3(c3cc(F)c(F)cc3F)C2)nc(C)c1F] | 439.24 |
| 9 | 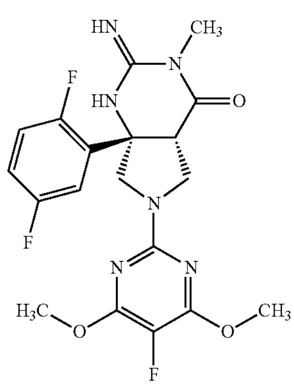 [SMILES: COc1nc(N2C[C@H]3C(=O)N(C)C(=N)N[C@@]3(c3cc(F)ccc3F)C2)nc(OC)c1F] | 437.24 |

-continued

| Ex | Structure | Obs. Mass |
|---|---|---|
| 10 | | 437.24 |
| 11 | | 421.23 |
| 12 | | 385.21 |
| 13 | | 439.24 |

| Ex | Structure | Obs. Mass |
|---|---|---|
| 14 | 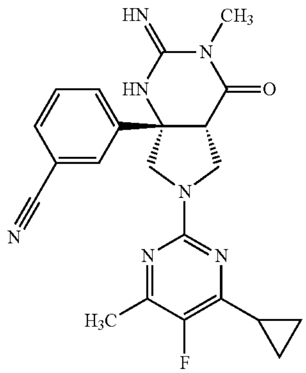 [SMILES: Cc1nc(N2C[C@H]3C(=O)N(C)C(=N)N[C@@]3(c3cccc(C#N)c3)C2)nc(C2CC2)c1F] | 420.2 |
| 15 | 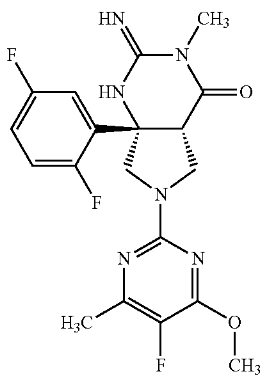 [SMILES: COc1nc(N2C[C@H]3C(=O)N(C)C(=N)N[C@@]3(c3cc(F)ccc3F)C2)nc(C)c1F] | 421.23 |
| 16 | 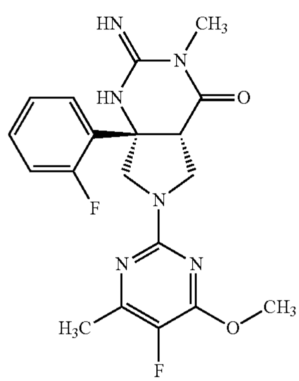 [SMILES: COc1nc(N2C[C@H]3C(=O)N(C)C(=N)N[C@@]3(c3ccccc3F)C2)nc(C)c1F] | 403.22 |
| 17 | 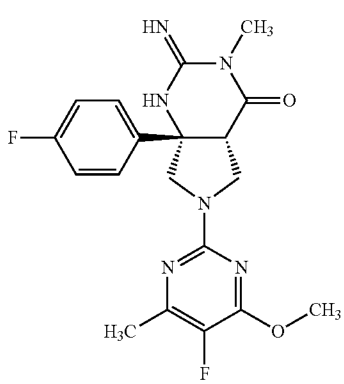 [SMILES: COc1nc(N2C[C@H]3C(=O)N(C)C(=N)N[C@@]3(c3ccc(F)cc3)C2)nc(C)c1F] | 403.22 |

| Ex | Structure | Obs. Mass |
|---|---|---|
| 18 | | 419.23 |
| 19 | | 463.3 |
| 20 | | 437 |
| 21 | | 429.2 |

-continued

| Ex | Structure | Obs. Mass |
|---|---|---|
| 22 | 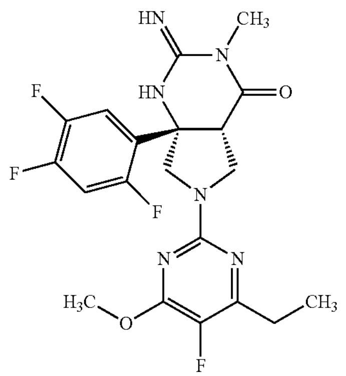 [SMILES: CCc1nc(N2C[C@H]3C(=O)N(C)C(=N)N[C@@]3(c3cc(F)c(F)cc3F)C2)nc(OC)c1F] | 453.2 |
| 23 racemic | 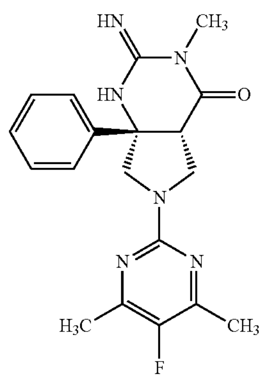 [SMILES: Cc1nc(N2C[C@H]3C(=O)N(C)C(=N)N[C@@]3(c3ccccc3)C2)nc(C)c1F] | 369.2 |
| 24 racemic | 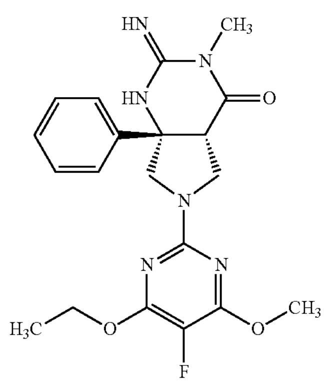 | 413.23 |
| 25 racemic | 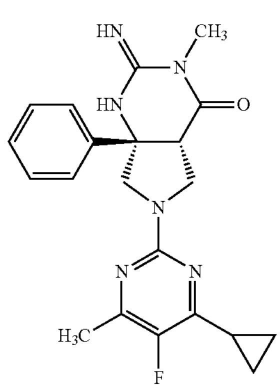 [SMILES: Cc1nc(N2C[C@H]3C(=O)N(C)C(=N)N[C@@]3(c3ccccc3)C2)nc(C2CC2)c1F] | 395.22 |

-continued

| Ex | Structure | Obs. Mass |
|---|---|---|
| 26 racemic | 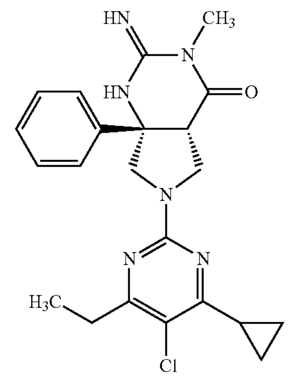 [SMILES: CCc1nc(N2C[C@H]3C(=O)N(C)C(=N)N[C@@]3(c3ccccc3)C2)nc(C2CC2)c1Cl] | 425.23 |
| 27 | 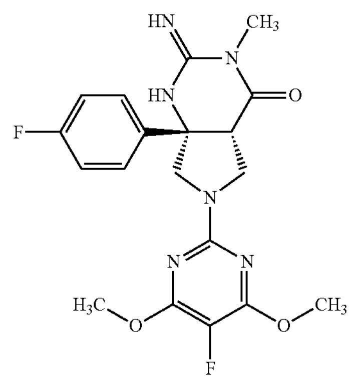 [SMILES: COc1nc(N2C[C@H]3C(=O)N(C)C(=N)N[C@@]3(c3ccc(F)cc3)C2)nc(OC)c1F] | 419.23 |
| 28 | 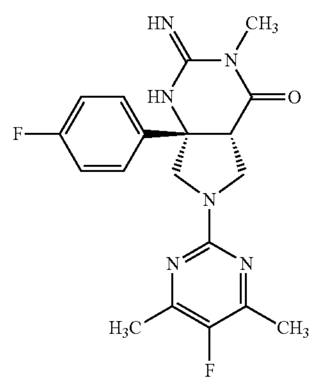 [SMILES: Cc1nc(N2C[C@H]3C(=O)N(C)C(=N)N[C@@]3(c3ccc(F)cc3)C2)nc(C)c1F] | 387.21 |
| 29 | 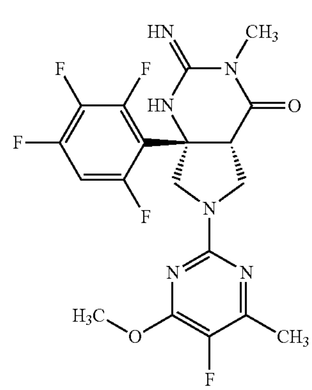 [SMILES: COc1nc(N2C[C@H]3C(=O)N(C)C(=N)N[C@@]3(c3c(F)cc(F)c(F)c3F)C2)nc(C)c1F] | 457.25 |

-continued

| Ex | Structure | Obs. Mass |
|---|---|---|
| 30 | 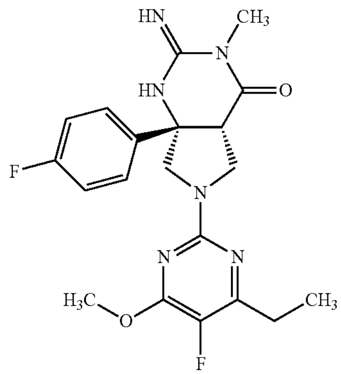 [SMILES: CCc1nc(N2C[C@H]3C(=O)N(C)C(=N)N[C@@]3(c3ccc(F)cc3)C2)nc(OC)c1F] | 417.23 |
| 31 | 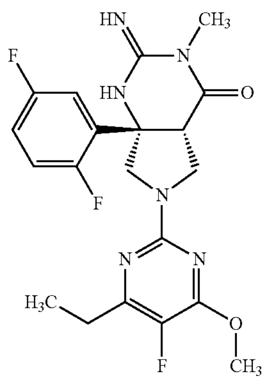 [SMILES: CCc1nc(N2C[C@H]3C(=O)N(C)C(=N)N[C@@]3(c3cc(F)ccc3F)C2)nc(OC)c1F] | 435.24 |
| 32 | 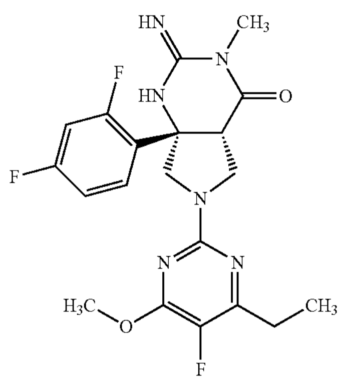 | 435.24 |
| 33 | 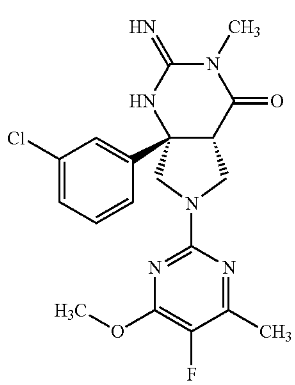 [SMILES: COc1nc(N2C[C@H]3C(=O)N(C)C(=N)N[C@@]3(c3cccc(Cl)c3)C2)nc(C)c1F] | 419.23 |

-continued

| Ex | Structure | Obs. Mass |
|---|---|---|
| 34 | 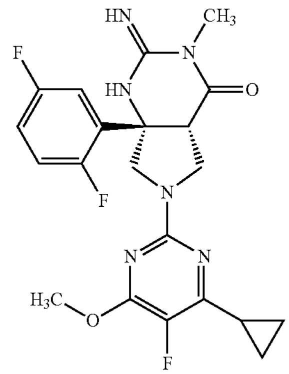 [SMILES: COc1nc(N2C[C@H]3C(=O)N(C)C(=N)N[C@@]3(c3cc(F)ccc3F)C2)nc(C2CC2)c1F] | 447.2 |
| 35 | 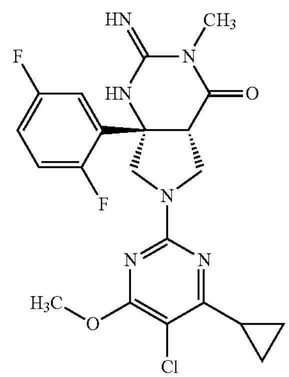 | 463.3 |
| 36 | 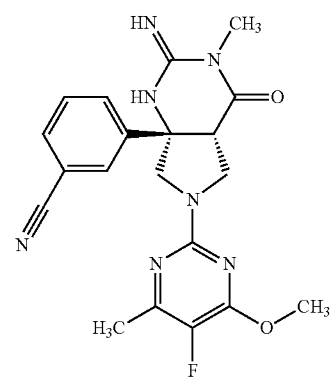 [SMILES: COc1nc(N2C[C@H]3C(=O)N(C)C(=N)N[C@@]3(c3cccc(C#N)c3)C2)nc(C)c1F] | 410.2 |
| 37 | 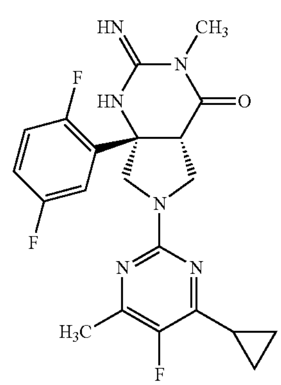 [SMILES: Cc1nc(N2C[C@H]3C(=O)N(C)C(=N)N[C@@]3(c3cc(F)ccc3F)C2)nc(C2CC2)c1F] | 431.2 |

-continued
| Ex | Structure | Obs. Mass |
|---|---|---|
| 38 | 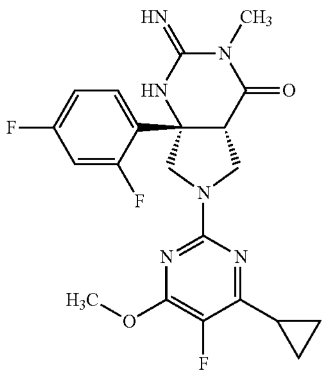 | 447.2 |
| 39 racemic | 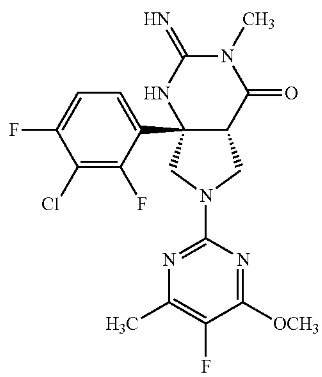 [SMILES: COc1nc(N2C[C@H]3C(=O)N(C)C(=N)N[C@@]3(c3ccc(F)c(Cl)c3F)C2)nc(C)c1F] | 456.3 |
| 40 | 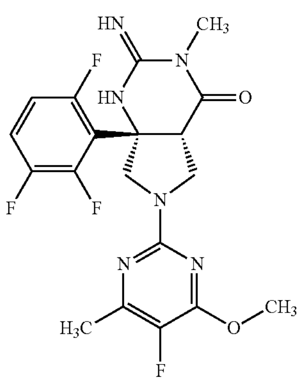 [SMILES: COc1nc(N2C[C@H]3C(=O)N(C)C(=N)N[C@@]3(c3c(F)ccc(F)c3F)C2)nc(C)c1F] | 439.24 |
Method K
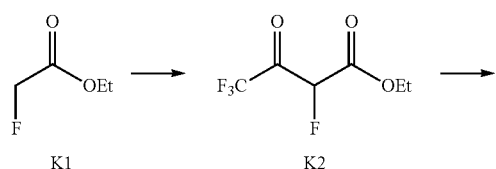
-continued
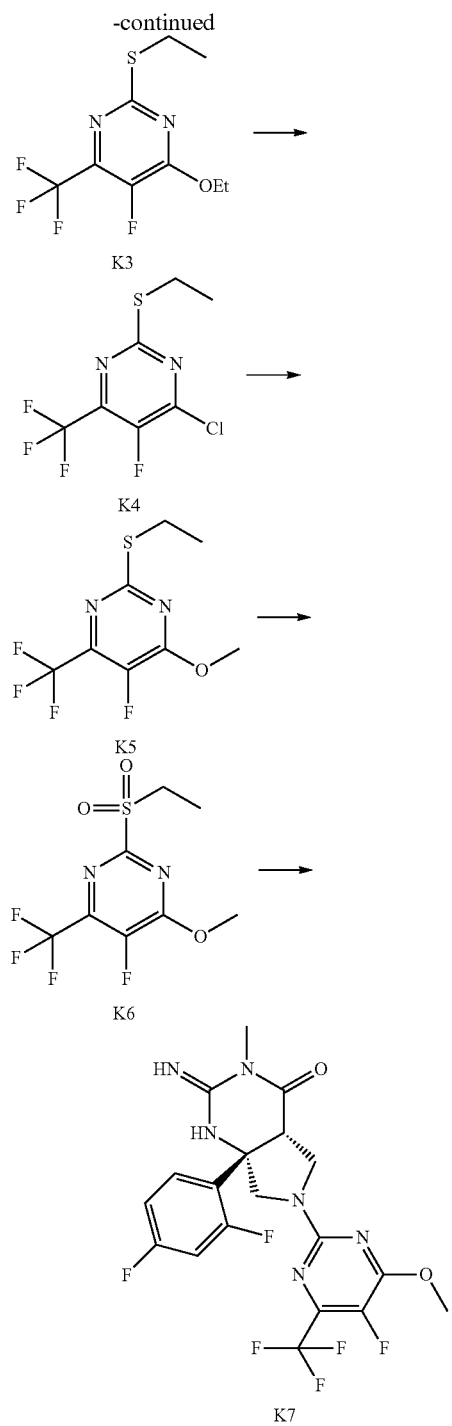
Method K, Step 1
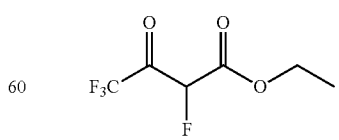
To a three-neck round bottom flask fitted with a condenser and an addition funnel was added ethyl trifluoroacetate (26.79 g, 189 mmol), anhydrous THF (50 mL) and 60% NaH/mineral oil (3.77 g, 94.3 mmol). The stirred reaction mixture was heated to 50° C., then ethyl fluoroacetate K1 (10.00 g, 94.3 mmol) was added dropwise over 1.5 hour via the addition funnel. After the addition, the reaction mixture was stirred at 50° C. for 2 hours, then cooled to rt and poured into ice (~50 g)/conc. $H_2SO_4$ (~5 mL). The aqueous layer was extracted with $Et_2O$ (3×100 mL). The combined organic layers were washed with water and brine and dried over $Na_2SO_4$, filtered and evaporated. The residue was purified by silica column chromatography (Analogix; EtOAc/Hexane, 0-35%) to give K2 (16.7 g, 87%) as a colorless oil. $^1$H NMR (CDCl$_3$) δ 5.06 (1H, d, J=47.6 Hz), 4.40 (2H, q, J=7.2 Hz), 1.39 (3H, t, J=7.2 Hz).

Method K, Step 2

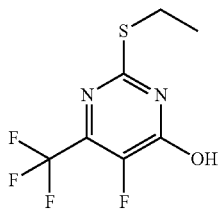

To a round bottom flask was added K2 (5.00 g, 24.7 mmol), S-ethylisothiourea hydrobromide (4.60 g, 24.9 mmol) and 25% NaOMe/MeOH (5.35 g, 24.9 mmol). The reaction mixture was heated at reflux overnight. After cooling to rt, the reaction mixture was poured into cold water and extracted with $CH_2Cl_2$ (3×50 mL). The combined organic layers were dried over $Na_2SO_4$, filtered and evaporated. The residue was purified by silica column chromatography (Analogix; MeOH/$CH_2Cl_2$ 0-5%) to give K3 (2.02 g, 30%) as a white solid. $^1$H NMR (CDCl$_3$) δ 3.20 (2H, q, J=7.2 Hz), 1.40 (3H, t, J=7.2 Hz). MS, m/e, 243.24 (Obs.).

Method K, Step 3

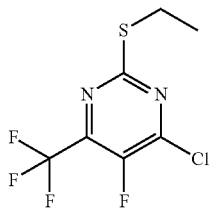

To a round bottom flask was added K3 (3.00 g, 12.4 mmol) and POCl$_3$ (25 mL). The reaction mixture was heated at 110° C. overnight. After cooling to rt, the reaction mixture was poured into ice and then brought to pH~8 with sat'd NaHCO$_3$. The aqueous layer was extracted with $Et_2O$ (3×100 mL). The combined organic layers were dried over $Na_2SO_4$, filtered and evaporated. The residue was then purified by silica column chromatography (Analogix; EtOAc/hexane; 0-30%) to give K4 (2.02 g, 63%) as a clear film. $^1$H NMR (CDCl$_3$) δ 3.16 (2H, q, J=7.2 Hz), 1.41 (3H, t, J=7.2 Hz).

Method K, Step 4

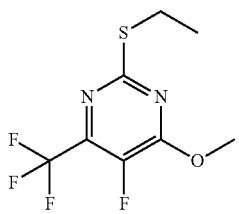 [SMILES: CCSc1nc(OC)c(F)c(C(F)(F)F)n1]

To a round bottom flask was added K4 (1.03 g, 3.52 mmol) and anhydrous THF (5 mL). The solution was cooled to 0° C. with stirring under N$_2$, and 25% NaOMe/MeOH (856 mg, 3.96 mmol) was added. The reaction mixture was then allowed to warm to rt and stirred for two hours. Additional 25% NaOMe/MeOH (152 mg, 0.704 mmol) was charged to the reaction. The reaction mixture was stirred at rt for an additional one hour and directly loaded onto a flash silica gel column. Elution with EtOAc/hexane (0-5%) gave K5 (900 mg, 99%) as a clear film. $^1$H NMR (CDCl$_3$) δ 4.10 (3H, s), 3.15 (2H, q, J=7.2 Hz), 1.40 (3H, t, J=7.2 Hz).

Method K, Step 5

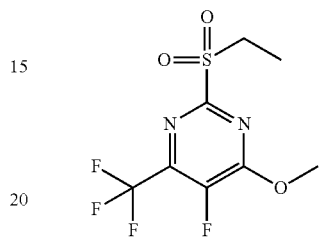

To a round bottom flask was added K$_5$ (900 mg, 3.51 mmol) and anhydrous $CH_2Cl_2$ (20 mL). The solution was cooled to 0° C. with stirring, and mCPBA (~77% purity, 1.80 g, 8.03 mmol) was added in portions. After the addition, the reaction mixture was warmed to rt and stirred for an additional hour. After evaporating most of the $CH_2Cl_2$, the residue was loaded on to a silica gel column and purified (Analogix; EtOAc/Hexane 0-100%) to afford K$_6$ (385 mg, 38%) as a white partial solid. $^1$H NMR (CDCl$_3$) δ 4.29 (3H, s), 3.61 (2H, q, J=7.2 Hz), 1.49 (3H, t, J=7.2 Hz). MS, m/e, 289.15 (Obs.).

Method K, Step 6

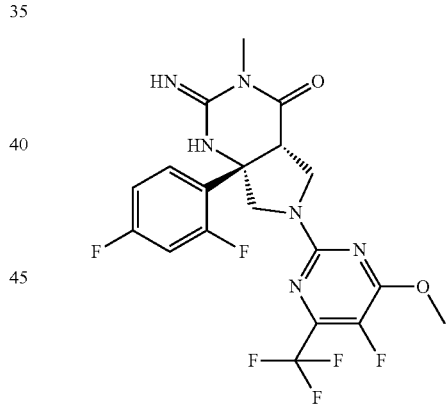

Example 41

To a round bottom flask was added D11 ($R^2=R^4=H$, $R^3=R^5=F$) (200 mg, 0.526 mmol), K6 (227 mg, 0.788 mmol), iPr$_2$NEt (0.26 mL, 1.49 mmol) and DMSO (1.5 mL). The reaction mixture was heated to 50° C. and stirred overnight. After cooling to rt, the reaction mixture was subjected directly to silica gel column chromatography (Analogix; EtOAc/Hexane, 0-100%) to give the Boc protected derivative of K7, which was treated with 20% TFA/$CH_2Cl_2$ (5 mL) for 2 hours at rt. The concentrated residue was purified by preparative TLC [5% (7N NH$_3$/MeOH)/$CH_2Cl_2$], and the product was treated with 2N HCl/Et$_2$O (2 mL) to give K7 (Example 41) as the HCl salt (5.5 mg, 2.0%) as a clear film. $^1$H NMR (CDCl$_3$) δ 7.39 (1H, m), 7.08 (m, 2H), 4.38 (1H, m), 4.05-3.70 (7H, m), 3.23 (3H, m). MS, m/e, 475.3.

The following compound (Example 42) was synthesized using a method similar to method K.

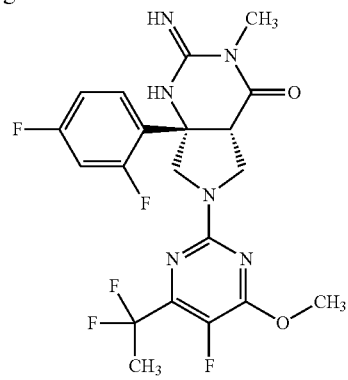

Obs. Mass
471.26

Example 42

Method L

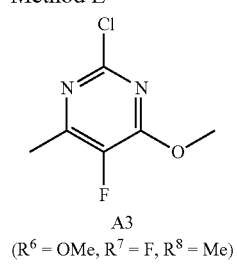

A3
($R^6$ = OMe, $R^7$ = F, $R^8$ = Me)

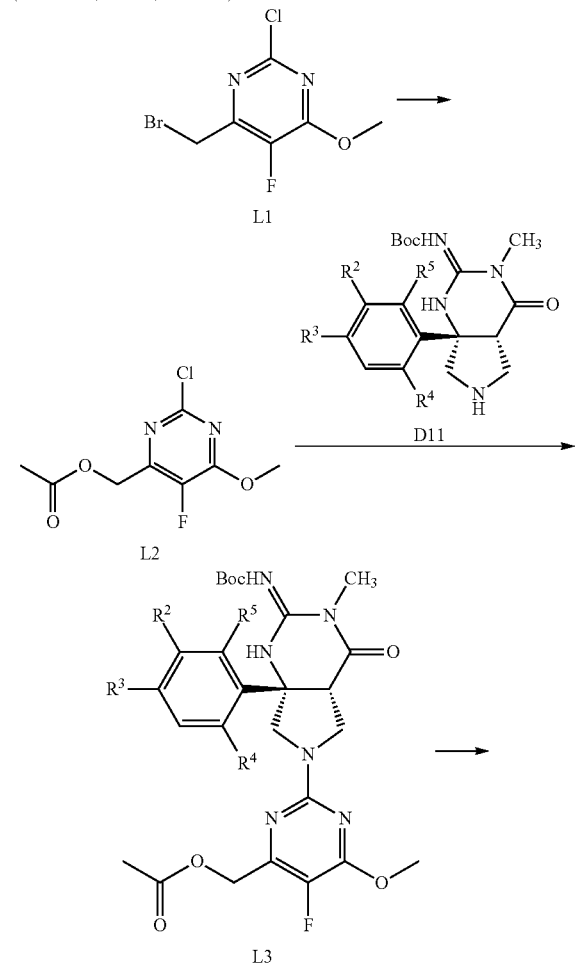

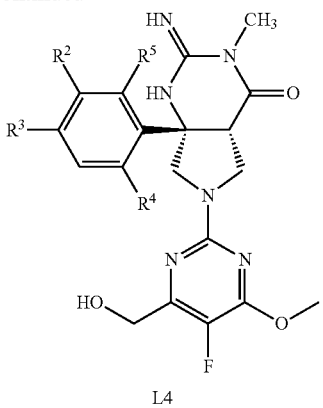

L4

Method L, Step 1

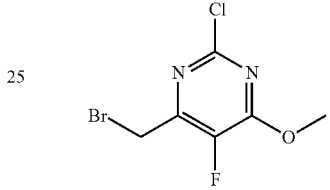

To a round bottom flask was added A3 ($R^6$=OMe, $R^7$=F, $R^8$=Me; 10.0 g, 56.6 mmol), AIBN (1.0 g, 6.1 mmol), NBS (30.0 g, 168.6 mmol) and CCl$_4$ (120 mL). The reaction mixture was heated at reflux for two days. After the reaction mixture had cooled to rt, it was poured into cold water then extracted with CH$_2$Cl$_2$ (3×200 mL). The combined organic layers were dried (Na$_2$SO$_4$), filtered and concentrated in vacuo to give the crude product (10.6 g) which contained an approximately 1:3 mixture L1: A3 ($R^6$=OMe, $R^7$=F, $R^8$=Me) by $^1$H NMR spectroscopy.

Method L, Step 2

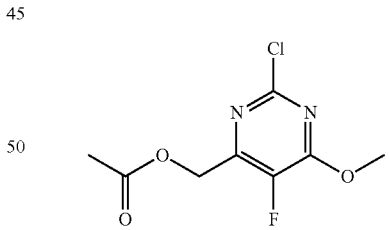

The crude product from Method L, Step 1 was dissolved in anhydrous MeCN (20 mL) and NaOAc (1.50 g, 18.3 mmol) was added. The reaction mixture was heated at 90° C. overnight. After the reaction mixture had cooled to rt, it was poured into cold water and extracted with CH$_2$Cl$_2$ (3×100 mL). The combined organic layers were dried (Na$_2$SO$_4$), filtered and concentrated. The residue was purified by flash silica gel chromatography (EtOAc/hexanes; 0-10%) to give L2 as a clear oil (2.20 g, 9.38 mmol, 16.6% overall yield from A3. L2 $^1$H NMR (CDCl$_3$) δ 5.15 (d, J=2.0 Hz, 2H), 4.10 (s, 3H), 2.15 (s, 3H). MS, m/e, 235 (M+H)$^+$.

Method L, Step 3

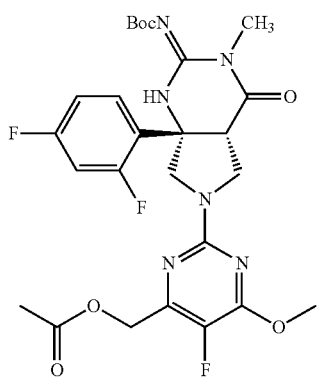

By essentially the procedure of Method G, Step 1, D11 ($R^2=R^4=H$, $R^3=R^5=F$; prepared from E7, enantiomer B, 1.60 g, 4.21 mmol), was reacted with L2 (1.18 g, 5.03 mmol) to give L3 ($R^2=R^4=H$, $R^3=R^5=F$) as white solid (0.459 g, 0.794 mmol, 19% yield). $^1$H NMR (CD$_3$OD) δ 7.41 (m, 1H), 7.20 (m, 1H), 7.08 (m, 1H), 5.11 (s, 2H), 4.58 (d, 1H), 4.25 (m, 2H), 4.05 (s, 3H), 4.01 (m, 2H), 2.11 (s, 3H). LC-MS m/e 479 (M+H)$^+$.

Method L, Step 4

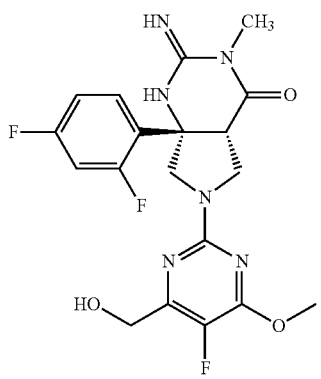 [SMILES: COc1nc(N2C[C@H]3C(=O)N(C)C(=N)N[C@@]3(c3ccc(F)cc3F)C2)nc(CO)c1F]

Example 43

A mixture of L3 ($R^2=R^4=H$, $R^3=R^5=F$; 0.459 g, 0.794 mmol), K$_2$CO$_3$ (0.264 g, 1.91 mmol) and MeOH (30 mL) was stirred at rt for 30 minutes. The mixture was then poured into sat. NH$_4$Cl (50 mL) and extracted with CH$_2$Cl$_2$ (3×50 mL). The combined organic layers were dried (Na$_2$SO$_4$), filtered and concentrated. The residue was then dissolved in 20% TFA/CH$_2$Cl$_2$ (5 mL), the mixture was stirred at rt for 1.5 hour, then concentrated in vacuo. The residue was purified by HPLC (reverse phase, C18 column, 0.1% HCOOH/H$_2$O: 0.1% HCOOH/CH$_3$CN=0-100%) to afford L4 (Example 43; $R^2=R^4=H$, $R^3=R^5=F$; 0.195 g, 89% yield) as a white solid. $^1$H NMR (CD$_3$OD) δ 7.34 (m, 1H), 6.94 (m, 2H), 4.65 (d, J=1.6 Hz, 2H), 4.58 (d, 1H), 4.35 (t, 1H), 4.09 (t, 1H) 4.00 (m, 4H), 3.85 (t, 1H), 3.34 (s, 3H). LC-MS, m/e, 437 (M+H)$^+$.

Method M

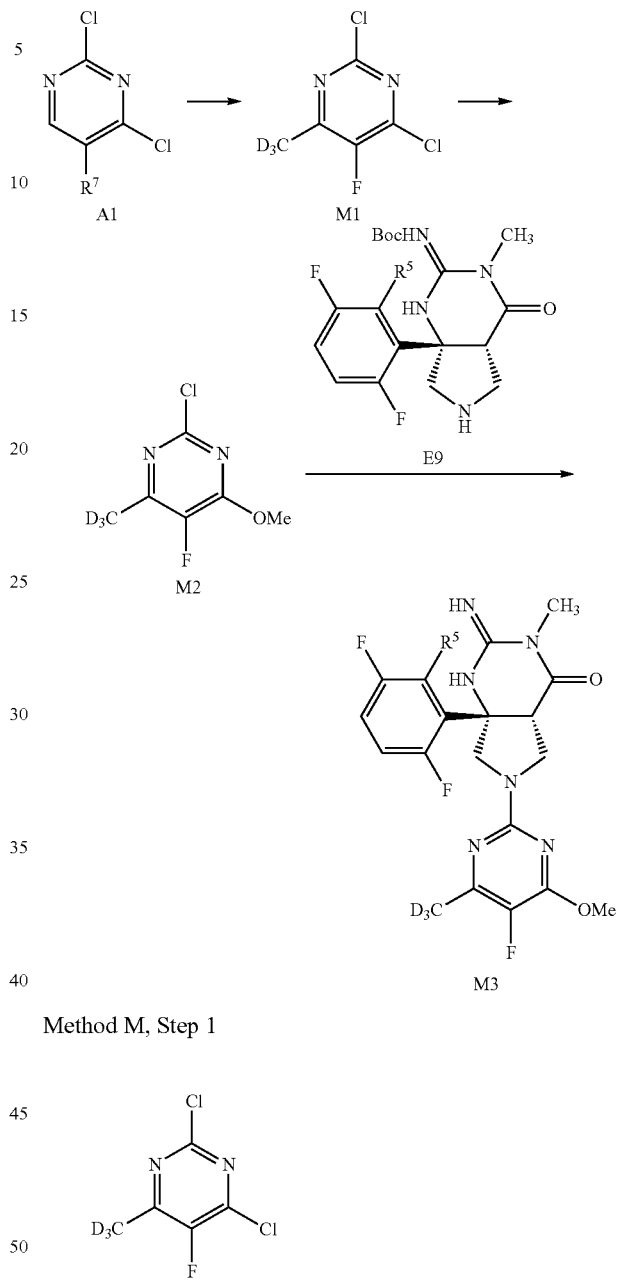

Method M, Step 1

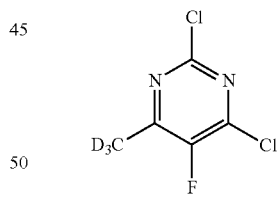

To a solution of CD$_3$MgI (prepared from CD$_3$I following a procedure similar to that described for MeMgBr (Organic Syntheses, Coll. Vol. 9, p. 649 (1998); Vol. 74, p. 187, (1997)); 45 mmol, 1.5 equiv.) in THF (20 mL) was added a solution of A1 ($R^7$=F, 5.0 g, 30 mmol, 1 equiv.) in DME (20 mL) while maintaining the temperature below 15° C. The resulting solution was stirred at 15° C. for 1 hour and then was cooled to 0° C. A solution of triethylamine (30 mmol, 1 equiv., 4.17 mL) in THF (10 mL) was added slowly to the reaction mixture while maintaining the internal temperature ~5° C., then a solution of iodine (30 mmol, 1 equiv.) in THF (10 mL) was added. The reaction mixture was quenched with water, warmed to rt, and extracted with ethyl acetate. The organic extract was concentrated and the crude product was purified (SiO$_2$ column, CH$_2$Cl$_2$/hexanes) to afford M1 (4.1 g, 74% yield).

Method M, Step 2

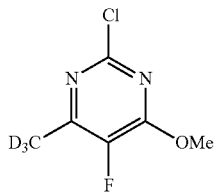 [SMILES: [2H]C([2H])([2H])c1nc(Cl)nc(OC)c1F]

To a solution of M1 (563 mg, 3.11 mmol) in THF (6 mL) was added a solution of 25% sodium methoxide (671 mg) in methanol while cooling at 0° C. The resulting solution was slowly warmed to rt over 1 hr, and then diluted with water and extracted with ethyl acetate. The organic extract was concentrated and the crude product was purified (SiO$_2$ column, EtOAc/hexanes) providing M2 in quantitative yield. $^1$H NMR (CDCl$_3$) δ 4.1 (s).

Method M, Step 3

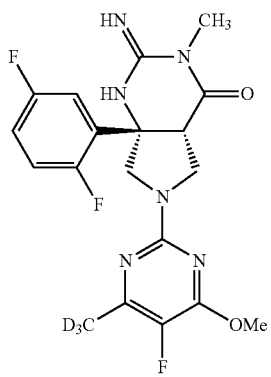 [SMILES: [2H]C([2H])([2H])c1nc(N2C[C@H]3C(=O)N(C)C(=N)N[C@@]3(c3cc(F)ccc3F)C2)nc(OC)c1F]

Example 44

By essentially the procedure of Method H, Steps 1 and 2, E9 (250 mg, 0.65 mmol) and M2 (138 mg, 1.1 equiv.) were coupled and the resultant product was reacted with TFA to give M3 (Example 44) following reverse phase HPLC(C18 column; 0.1% water/acetonitrile). $^1$H NMR (CDCl$_3$) δ 7.2 (m, 3H), 4.5 (m, 1H), 4.2 (m, 2H), 3.95 (m, 5H).

Method N

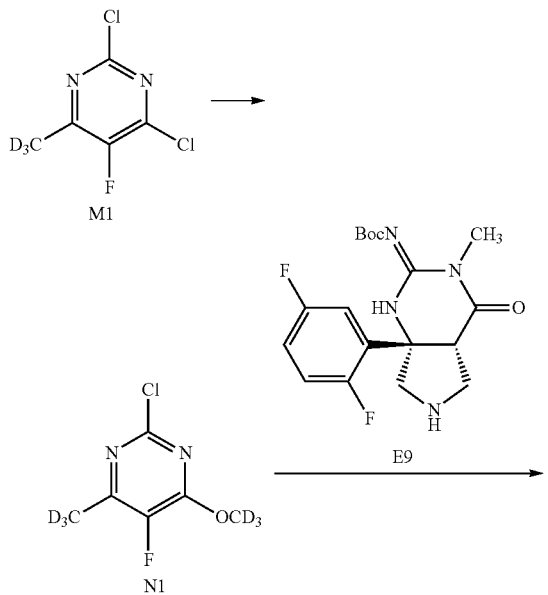

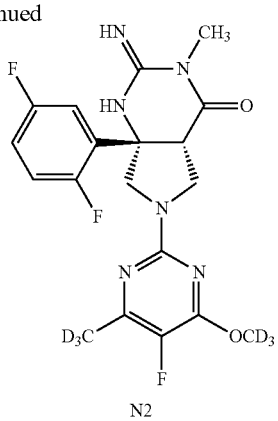

Method N, Step 1

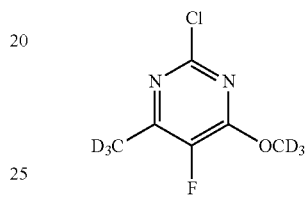

To a solution of M1 (563 mg, 3.11 mmol) in THF (6 mL) was added a solution of NaOCD$_3$ (671 mg) in THF (prepared by the addition of NaH to a THF solution of CD$_3$OD) while cooling at 0° C. The resulting solution was slowly warmed to rt over 1 hr, then diluted with water and extracted with ethyl acetate. Purification (SiO$_2$ column, EtOAc/hexanes) provided N1 in quantitative yield.

Method N, Step 2

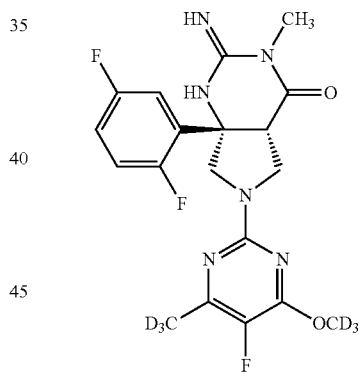

Example 45

By essentially the procedure of Method H, Steps 1 and 2, E9 and N1 were coupled and the resultant product was reacted with TFA to give N2 (Example 45). $^1$H NMR (CDCl$_3$) δ 7.2 (m, 3H), 4.5 (m, 1H), 4.2 (m, 2H), 3.9 (m, 2H).

Assays

The protocol that was used to determine the recited values is described as follows.

BACE1 HTRF FRET Assay

Reagents

Na$^+$-Acetate pH 5.0
1% Brij-35
Glycerol
Dimethyl Sulfoxide (DMSO)
Recombinant human soluble BACE1 catalytic domain (>95% pure)
APP Swedish mutant peptide substrate (QSY7-APP$^{swe}$-Eu): QSY7-EISEVNLDAEFC-Europium-amide A homogeneous time-resolved FRET assay was used to determine $IC_{50}$ values for inhibitors of the soluble human BACE1 catalytic domain. This assay monitored the increase of 620 nm fluorescence that resulted from BACE1 cleavage of an APPswedish $APP^{swe}$ mutant peptide FRET substrate (QSY7-EISEVNLDAEFC-Europium-amide). This substrate contained an N-terminal QSY7 moiety that served as a quencher of the C-terminal Europium fluorophore (620 nm Em). In the absence of enzyme activity, 620 nm fluorescence was low in the assay and increased linearly over 3 hours in the presence of uninhibited BACE1 enzyme. Inhibition of BACE1 cleavage of the QSY7-$APP^{swe}$-Eu substrate by inhibitors was manifested as a suppression of 620 nm fluorescence.

Varying concentrations of inhibitors at 3× the final desired concentration in a volume of 10 ul were preincubated with purified human BACE1 catalytic domain (3 nM in 10 □l) for 30 minutes at 30° C. in reaction buffer containing 20 mM Na-Acetate pH 5.0, 10% glycerol, 0.1% Brij-35 and 7.5% DSMO. Reactions were initiated by addition of 10 □l of 600 nM QSY7-$APP^{swe}$-Eu substrate (200 nM final) to give a final reaction volume of 30 □l in a 384 well Nunc HTRF plate. The reactions were incubated at 30° C. for 1.5 hours. The 620 nm fluorescence was then read on a Rubystar HTRF plate reader (BMG Labtechnologies) using a 50 □s delay followed by a 400 millisecond acquisition time window. Inhibitor $IC_{50}$ values were derived from non-linear regression analysis of concentration response curves. $K_i$ values were then calculated from $IC_{50}$ values using the Cheng-Prusoff equation using a previously determined □m value of 8 □M for the QSY7-$APP^{swe}$-Eu substrate at BACE1.

BACE Inhibitor Whole Cell IC50 Determination Using HEK293-$App^{swe/lon}$ Cells

HEK293 cells were obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-$APP^{swe/lon}$) was identified and maintained at 37° C., 5% $CO_2$ in the ATCC-recommended growth media supplemented with hygromycin. Determination of compound $IC_{50}$ values for inhibition of APP processing (reduction of Aβ1-40, Aβ1-42 and sAPPβ levels) in HEK293-$APP^{swe/lon}$ Ion cells was accomplished by treatment of cells with various concentrations of compounds diluted in fresh complete growth media for 4 hours at 37° C., 5% $CO_2$. Aβ40 or Aβ42 were measured in 15 μl of media using a mesoscale based ELISA assay. Full length Aβ40 and Aβ42 peptides were captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescence values were measured using a Mesoscale Sector Imager plate reader and were plotted as a function of compound concentration. $IC_{50}$ values were interpolated from the data using nonlinear regression analysis (Sigmoidal dose response fit with variable slope) of the data using GraphPad Prism software.

CYP Inhibition Assay

In order to assess the potential for inhibition of CYPs, human liver microsomes (0.4 mg/ml) were incubated with several concentrations of test article (0 to 50 μM), 1 mM NADPH, and substrates for various CYPs at 37° C. for 10-20 minutes, depending on the enzyme reaction, in a buffer composed of 50 mM Tris-acetate, pH 7.4, and 150 mM potassium chloride. The test article was dissolved in methanol at a concentration of 5 mM. Dilutions of the stock solution were also prepared in methanol. The substrate concentration was kept near the Km value for each CYP reaction. The substrates were 100 μM phenacetin (O-deethylase reaction) for CYP1A2, 16 μM dextromethorphan (O-demethylase reaction) for CYP2D6, 100 μM testosterone (6β-hydroxylase reaction) and 5 μM midazolam (1'-hydroxylase reaction) for CYP3A4, 200 μM tolbutamide (4-hydroxylase reaction) for CYP2C9, 125 μM S-(+)-mephenyloin (4-hydroxylase reaction) for CYP2C19 and 5 μM paclitaxel (6□-hydroxylase reaction) for CYP2C8. The reactions were terminated by the addition of 35% perchloric acid to a final concentration of 4.5% (vol:vol). The concentrations of the metabolites formed from each substrate after incubation were determined by LC-MS/MS using a standard curve. The concentration of test article that inhibits 50% of the initial enzyme activity ($IC_{50}$) values was determined from the graph of test article concentrations versus percent of inhibition.

To evaluate metabolism/mechanism-based inhibition, the test article, at the stated concentrations (0 to 50 μM), was pre-incubated with human liver microsomes for 30 min at 37° C. in the presence of NADPH and in the absence of the substrates. After the pre-incubation step, the CYP substrates were added at the previously stated concentrations and the reactions were allowed to proceed as indicated in the previous paragraph.

Methods of hERG Screening

IonWorks Quattro

The IonWorks Quattro (Molecular Devices, Sunnyvale, Calif.) is a screening device for conducting parallel voltage clamp measurements. This second generation automated patch clamp device was used in the "Population Patch Clamp" (PPC) mode in which average currents from up to 64 cells were recorded within any given well. Each Patch Plate well had 64 1-2 μm holes in the bottom on which cells could settle in an 8×8 array.

The external solution used for the IonWorks studies was Dulbecco's PBS (Life Technologies) supplemented with 1.25 mM KCl to provide a final potassium concentration of 5.4 mM, 1 mg/ml glucose and 1% DMSO. The internal solution contains (mM concentrations): 20 KCl, 130 K-gluconate, 5 HEPES-KOH (pH 7.25), 2 $CaCl_2$, 1 $MgCl_2$+1% DMSO. Amphotericin was added at 5 mg in 70 ml when present (700 μl DMSO used to dissolve the amphotericin prior to addition). The presence of 1% DMSO in all solutions did not affect current stability or well to well variability. Compounds plates were prepared as 3× because the IonWorks makes three 3.5 μl additions to each well (buffer alone, then buffer plus cells, then 3× compound). Compounds were added to the 3× compound plate from stocks in 100% DMSO by adding 2.5 μl of stock to 250 μl of DMSO-free saline per compound plate well. Plates were then placed on a plate shaker for at least 20 minutes.

hERG L929 cells (subcloned from cells obtained from S. Taffit, SUNY Syracuse) were used for IonWorks Quattro screening. On the day of the experiments, cells were released from culture flasks using Trypsin-EDTA. Cells were then pelleted and resuspended into Dulbecco's phosphate buffered saline supplemented with 1.25 mM KCl at 1.5 million cells per ml.

During an IonWorks run, on the board fluid handling head added 3 different 3.5 μl aliquots to individual patch plate wells. The first addition was extracellular saline. Next the cell suspension was added. After "seals" were formed, electrical access to the cell interior was gained by the addition of the pore-forming antibiotic, amphotericin B, to a common chamber beneath the patch plate. For evaluation of the effects of test substances on hERG currents, cells were transiently voltage clamped in blocks of 48 wells prior to addition of test articles. Cells were transiently voltage clamped again five minutes after the addition of test articles. Test substances were added in quadruplicate from a 96-well polypropylene compound plate. The average success rate (wells passing all user-defined acceptance criteria) was approximately 98%. User-defined filters were set to 150 pA for pre-compound current amplitude, 35 MΩ for pre-compound resistance and of 35 MΩ for post-compound resistance.

For the IonWorks studies, cells were clamped at −80 mV for 10 seconds prior to data collection to ensure that hERG channels were fully available. The current during a brief (200 msec) step to −40 mV was then sampled to provide a measure of all non-hERG currents (leak currents). The measurement of this reference current was felt to be critical because the built in leak subtraction algorithm used by the IonWorks software was frequently found to be unreliable. The 200 msec step to −40 mV was followed by a 5 second depolarization to +20 mV to activate the channel. Tail currents were measured during an ensuing return to −40 mV. hERG tail current amplitude was measured as the peak tail current during the second step to −40 mV minus the non-hERG current at −40 mV.

Percent inhibition was calculated relative to the mean of a vehicle and time controlled group of cells using the following equation:

$$\% \text{ inhibition} = (1 - (F_D/F_V)) \times 100\%$$

where $F_D$=the average fraction of baseline current after drug exposure $F_V$=the average fraction of baseline current after vehicle exposure The average fraction of current remaining after vehicle ranged from 0.95 to 1.05.

Rubidium Efflux

The base solution for the rubidium efflux studies was 144 mM NaCl, 20 mM HEPES-NaOH (pH 7.4), 2 mM $CaCl_2$, 1 mM $MgCl_2$, and 11 mM glucose. To prepare the rubidium loading buffer 5.4 mM RbCl was added. The wash buffer was supplemented with 5.4 mM KCl. The depolarization buffer was prepared by adding 40 mM KCl to the wash buffer. Drugs were added as 4× stocks containing 10% DMSO with a resulting final DMSO concentration of 2.5%.

hERG-CHO cells were plated into 96-well flat-bottom dishes and returned to the incubator for 24 hours. On the day of study, culture medium was removed and replaced by a HEPES-buffered saline solution containing 5.4 mM RbCl. Cells were returned to the tissue culture incubator for 3 hours to permit rubidium loading. Test compounds (4×) in rubidium loading buffer plus 10% DMSO were added and cells were equilibrated for 30 minutes in the incubator. Plates were then washed 3× with HEPES buffered saline containing 5.4 mM KCl and zero rubidium. After the $3^{rd}$ wash cells were depolarized by the addition of 200 μl HEPES buffered saline containing 45.4 mM KCl. Cells were incubated in the depolarization solution for 5 minutes to permit efflux of rubidium. Supernatants were then collected and analyzed for rubidium content using automated flame atomic absorbance spectroscopy (ICR-8000, Aurora Biosciences). Percent inhibition was quantified based on a signal window defined by no block (vehicle) and full block with 10 μM dofetilide. All pipetting steps for the rubidium efflux screen were implemented using a pipetting robot capable of making simultaneous additions and removals from 96 wells (Quadra-96).

Human Cathepsin D FRET Assay

This assay can be run in either continuous or endpoint format. The substrate used below has been described (Y. Yasuda et al., J. Biochem., 125, 1137 (1999)). Substrate and enzyme are commercially available.

The assay was run in a 30 □l final volume using a 384 well Nunc black plate. 8 concentrations of compound were pre-incubated with enzyme for 30 mins at 37° C. followed by addition of substrate with continued incubation at 37° C. for 45 mins. The rate of increase in fluorescence was linear for over 1 h and was measured at the end of the incubation period using a Molecular Devices FLEX station plate reader. $K_i$s were interpolated from the $IC_{50}$s using a Km value of 4 □M and the substrate concentration of 2.5 □M.

Reagents

Na-Acetate pH 5

1% Brij-35 from 10% stock (Calbiochem)

DMSO

Purified (>95%) human liver Cathepsin D (Athens Research & Technology Cat#16-12-030104)

Peptide substrate (Km=4 □M) Mca-Gly-Lys-Pro-Ile-Leu-Phe-Phe-Arg-Leu-Lys(Dnp)-D-Arg-$NH_2$ (Bachem Cat # M-2455)

Pepstatin is used as a control inhibitor ($K_i$~0.5 nM) (Sigma).

Nunc 384 well black plates

Final Assay Buffer Conditions 100 mM Na Acetate pH 5.0

0.02% Brij-35

1% DMSO

Compound was diluted to 3× final concentration in assay buffer containing 3% DMSO. 10 □l of compound was added to 10 □l of 2.25 nM enzyme (3×) diluted in assay buffer without DMSO, mixed briefly, spun, and incubated at 37° C. for 30 mins. 3× Substrate (7.5 □M) was prepared in 1× assay buffer without DMSO. 10 □l of substrate was added to each well mixed and spun briefly to initiate the reaction. Assay plates were incubated at 37° C. for 45 mins and read on a 384 compatible fluorescence plate reader using a 328 nm Ex and 393 nm Em.

Applicants have found that the compounds of the invention, which are novel in view of Zhu, et al. (WO2006/138264), exhibit one or more properties which are expected to make them suitable for the treatment of Aβ related pathologies, including Alzheimer's Disease, and for the other uses described herein. Moreover in some embodiments, Applicants have found, surprisingly and unexpectedly, that certain compounds or groups of compounds of the invention exhibit good potency for BACE-1. In some embodiments, certain compounds or groups of compounds of the invention (including but not limited to the compounds of the Table below encompassed by Formula (II-AA) and/or Formula (II-AB)) exhibit an unexpected combination of good potency for BACE-1 and good selectivity with respect to Cathepsin D. In some embodiments, certain compounds or groups of compounds of the invention exhibit an unexpected combination of good potency for BACE-1, good selectivity with respect to Cathepsin D, and good selectivity with respect to certain cytochrome p450 enzymes. In some embodiments, certain compounds or groups of compounds of the invention exhibit an unexpected combination of good potency for BACE-1, good selectivity with respect to Cathepsin D, good selectivity with respect to certain cytochrome p450 enzymes, and good selectivity with respect to hERG. In some embodiments, certain compounds or groups of compounds of the invention exhibit an unexpected combination of good potency for BACE-1 and one or more additional property such as: good selectivity with respect to Cathepsin D; good selectivity with respect to certain cytochrome p450 enzymes; good selectivity with respect to hERG; good pharmacokinetic profile; and/or good pharmacodynamic profile. Properties of example compounds of the invention may be appreciated, for example, by assaying for properties using known methods and/or by reference to Table IA below. (The example numbers in the leftmost column of Table IA correspond to the example numbers for the compounds pictured in Table I, above.)

TABLE IA

| Example | BACE1 KI nM | BACE1 Aβ$_{40}$ IC$_{50}$ nM | CathD Selec- tivity | CYP 2D6 IC$_{50}$ uM co | CYP 2D6 IC$_{50}$ uM pre | CYP 3A4 IC$_{50}$ uM pre | CYP 3A4 IC$_{50}$ uM co | CYP 2C9 IC$_{50}$ uM co | CYP 2C9 IC$_{50}$ uM pre | HERG Ionworks % Inhib 10 uM | HERG Ionworks % Inhib 1 uM | HERG Rb efflux % Inhib 5 uG/mL | HERG Rb efflux % Inhib 1.5 uG/mL |
|---|---|---|---|---|---|---|---|---|---|---|---|---|---|
| 12 | 12 | 38 | 142 | | | | | | | | | 18 | 20 |
| 1 | 4.7 | 14 | 458 | ~30 | 26.6 | >30 | >30 | >30 | >30 | 45 | 3 | | |
| 15 | 8.5 | 28 | 158 | 13.5 | ~30 | >30 | >30 | 21.6 | ~30 | 57 | 6 | | |
| 18 | 9.3 | 32 | 228 | | | | | | | | | | |
| 11 | 32 | 61 | 254 | | | | | | | | | | |
| 17 | 7.3 | 16 | 354 | ~30 | 25.5 | 24.1 | >30 | >30 | >30 | 74 | 10 | | |
| 4 racemic | 59 | 323 | 248 | ~30 | >30 | >30 | >30 | >30 | >30 | | | | |
| 23 racemic | 154 | 292 | | >30 | >30 | >30 | >30 | >30 | >30 | | | | |
| 24 racemic | 137 | | 129 | 22.6 | ~30 | >30 | >30 | >30 | >30 | | | | |
| 5 racemic | 61 | 217 | | ~30 | >30 | >30 | >30 | >30 | >30 | | | | |
| 6 racemic | 16 | 144 | 318 | 24.9 | ~30 | >30 | >30 | >30 | >30 | | | | |
| 8 | 7.7 | 35 | 446 | >20 | >20 | >20 | >20 | >20 | >20 | 89 | 21 | | |
| 25 racemic | 44 | 349 | | >20 | >20 | >20 | >20 | >20 | >20 | | | | |
| 7 racemic | 94 | 664 | | | | | | | | | | | |
| 26 racemic | 180 | | | >20 | >20 | >20 | >20 | >20 | >20 | | | | |
| 27 | 4.4 | 61.5 | 1063 | 14.7 | ~30 | 4.2 | >30 | >30 | >30 | 51 | 2 | | |
| 28 | 64 | 114 | | 23.3 | ~30 | >30 | >30 | >30 | >30 | | | 14 | 13 |
| 9 | 5.6 | 66 | 386 | >30 | >30 | 18.6 | >30 | ~30 | ~30 | 71 | 12 | | |
| 10 | 1.8 | 7.5 | 583 | ~30 | >30 | >30 | >30 | >30 | >30 | 74 | 7 | | |
| 29 | 30 | 93 | 99 | >30 | >30 | ~30 | >30 | >30 | >30 | | | 3 | −4 |
| 30 | 6.1 | 22 | 163 | >30 | >30 | >30 | >30 | >30 | >30 | 31 | 2 | | |
| 31 | 6.9 | 31 | 596 | >20 | >20 | >20 | >20 | >20 | >20 | 88 | 21 | | |
| 32 | 5.3 | 26 | 310 | >20 | >20 | >20 | >20 | >20 | >20 | 95 | 19 | | |
| 13 | 15 | 21 | 773 | >20 | >20 | >20 | >20 | >20 | >20 | | | | |
| 33 | 39 | 176 | 43 | | | | | | | | | | |
| 34 | 5.6 | 86 | 88 | >20 | >20 | >20 | >20 | >20 | >20 | 65 | 7 | | |
| 35 | 6.5 | 90 | 634 | >20 | >20 | ~20 | >20 | ~20 | ~20 | 23 | 5 | | |
| 37 | 26 | 235 | | >20 | >20 | >20 | >20 | >20 | >20 | 73 | 12 | | |
| 38 | 2.7 | 31 | 209 | >20 | >20 | >20 | >20 | >20 | >20 | 63 | 12 | | |
| 19 | 6.8 | 117 | 236 | >20 | >20 | >20 | >20 | >20 | >20 | 20 | 3 | | |
| 42 | 11 | | | | | | | | | | | | |
| 41 | 32 | 67 | 346 | | | | | | | 77 | 1 | | |
| 16 | 6.0 | 16.5 | 143 | >30 | >30 | >30 | >30 | >30 | >30 | 61 | 11 | | |
| 14 | 43 | 213 | | >20 | >20 | >20 | >20 | >20 | >20 | 59 | 6 | | |
| 39 racemic | 9.2 | 40 | 221 | >20 | >20 | >20 | >20 | >20 | >20 | 61 | 3 | | |
| 2 | 8.9 | 42 | 162 | >20 | >20 | >20 | >20 | >20 | >20 | 50 | 8 | | |
| 36 | 14 | 63 | 1202 | >20 | >20 | >20 | >20 | >20 | >20 | 37 | 3 | | |
| 40 | 53 | 224 | 151 | >20 | >20 | >20 | >20 | >20 | >20 | 81 | 15 | | |
| 3 | 13 | 109 | 230 | >20 | >20 | >20 | >20 | 8.5 | 12.7 | 89 | 22 | | |
| 44 | 6.1 | 25 | 352 | >20 | >20 | >20 | >20 | >20 | >20 | 67 | 14 | | |
| 45 | 7.3 | 23 | 341 | >20 | >20 | >20 | >20 | >20 | >20 | 72 | 17 | | |
| 43 | 16 | 21 | 116 | >20 | >20 | >20 | >20 | >20 | >20 | 27 | 6 | | |
| 20 | 4.5 | 9.5 | 106 | >20 | >20 | 8.3 | >20 | 7.5 | 8.9 | 93 | 29 | | |
| 21 | 4.8 | 50 | 50 | 13.7 | 10.1 | >20 | >20 | >20 | >20 | 73 | 7 | | |
| 22 | 5.6 | 18 | 53 | >20 | >20 | >20 | >20 | ~20 | >20 | 96 | 35 | | |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound, or a deuterate thereof, or a tautomer of said compound or said deuterate, or a pharmaceutically acceptable salt of said compound, said deuterate, or said tautomer, said compound having the structural Formula (II-A):

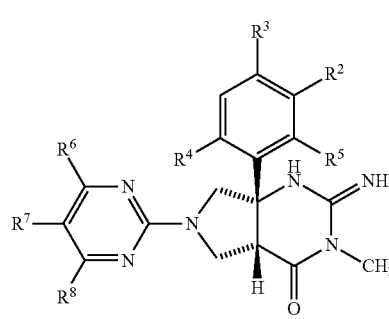

(II-A)

wherein $R^2$, $R^3$, $R^4$, $R^5$, $R^8$, $R^7$, and $R^8$ are each selected independently and wherein:
$R^2$ is selected from hydrogen, fluorine, chlorine, and cyano;
$R^3$ is selected from hydrogen, fluorine, chlorine, and cyano;
$R^4$ is selected from hydrogen, fluorine, chlorine, and cyano;
$R^5$ is selected from hydrogen, fluorine, and chlorine;
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, lower haloalkyl, lower haloalkoxy, cycloalkyl, -alkyl-cycloalkyl, —O-cycloalkyl, and —O-alkyl-cycloalkyl.

2. A compound of claim 1, or a tautomer thereof, or a pharmaceutically acceptable salt of said compound or said tautomer, wherein:
$R^6$ is selected from lower alkyl, lower alkoxy, lower haloalkyl, lower haloalkoxy, and lower alkyl-OH;
$R^7$ is selected from fluorine and chlorine; and
$R^8$ is selected from lower alkyl, lower alkoxy, and cyclopropyl.

3. A compound of claim 1, or a tautomer thereof, or a pharmaceutically acceptable salt of said compound or said tautomer, wherein:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl.

4. A compound of claim 1, or a tautomer thereof, or a pharmaceutically acceptable salt of said compound or said tautomer, wherein:
$R^6$ is selected from methyl, ethyl, and methoxy;
$R^7$ is selected from fluorine and chlorine; and
$R^8$ is selected from methoxy and cyclopropyl.

5. A compound of claim 1, or a tautomer thereof, or a pharmaceutically acceptable salt of said compound or said tautomer, wherein:
$R^6$ is selected from methyl, ethyl, methoxy, ethoxy, —CH$_2$OH, —CF$_3$, and —CF$_2$CH$_3$;
$R^7$ is selected from fluorine and chlorine; and
$R^8$ is selected from methoxy, ethoxy, cyclopropyl, and ethyl;

and the moiety

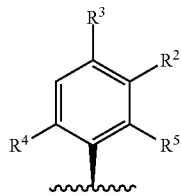

shown in Formula (II-A) is selected from:

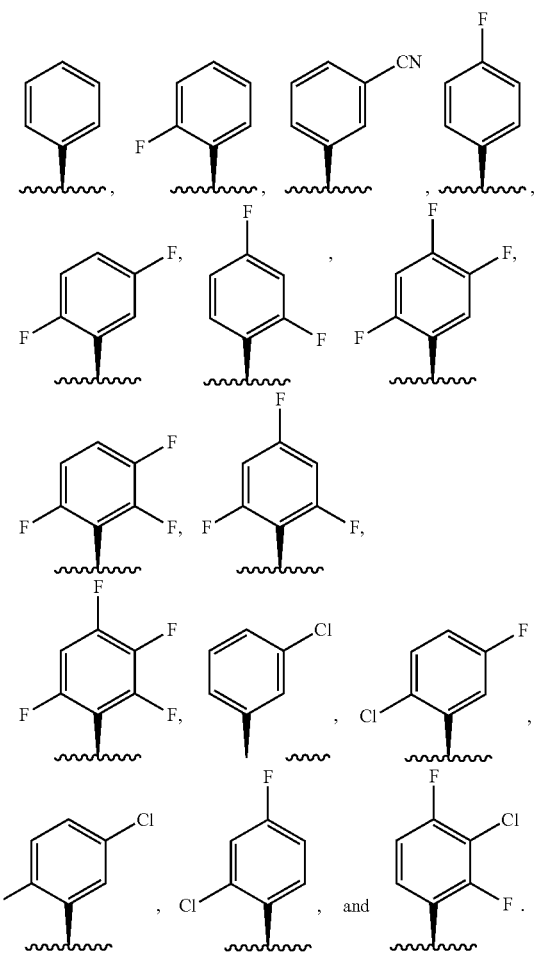

6. A compound of claim 1, or a tautomer thereof, or a pharmaceutically acceptable salt of said compound or said tautomer, wherein:

the moiety

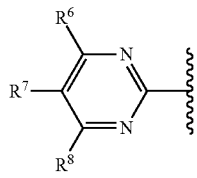

shown in Formula (II-A) is selected from the group consisting of

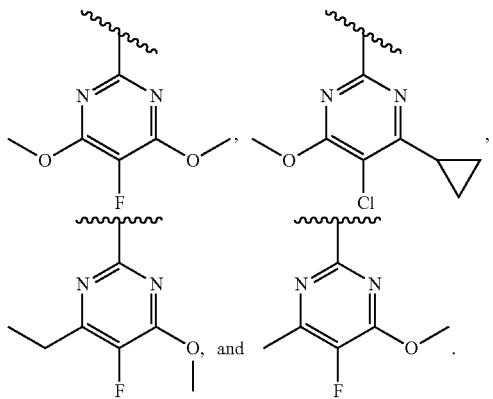

7. A compound, or a tautomer thereof, or a pharmaceutically acceptable salt of said compound or said tautomer, said compound having the structural Formula (II-AA):

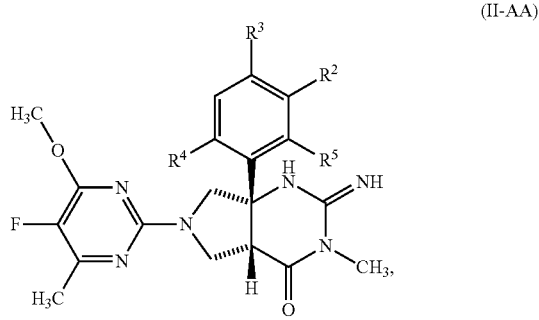

(II-AA)

wherein:
- $R^2$ is selected from hydrogen, fluorine, chlorine, and cyano;
- $R^3$ is selected from hydrogen, fluorine, chlorine, and cyano;
- $R^4$ is selected from hydrogen, fluorine, chlorine, and cyano; and
- $R^5$ is selected from hydrogen, fluorine, and chlorine.

8. A compound of claim 7, or a tautomer thereof, or a pharmaceutically acceptable salt of said compound or said tautomer, wherein: the moiety

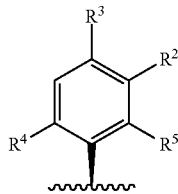

shown in Formula (II-AA) is selected from:

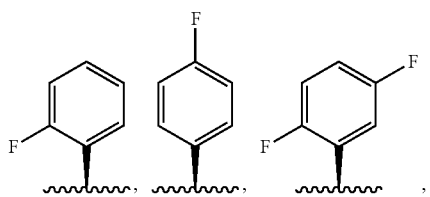

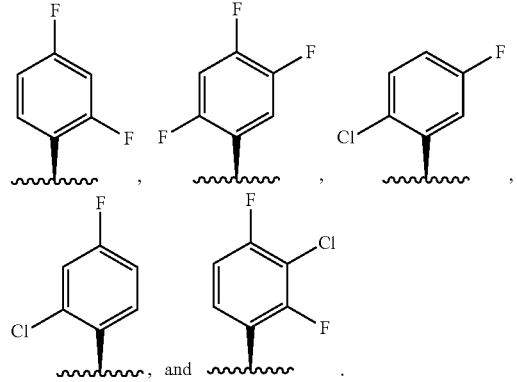

9. A compound, or a tautomer thereof, or a pharmaceutically acceptable salt of said compound or said tautomer, said compound having the structural Formula (II-AB):

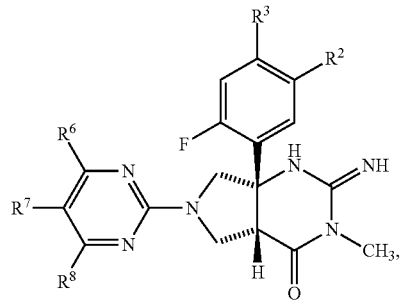

(II-AB)

wherein each variable is selected independently of the others and wherein: the moiety

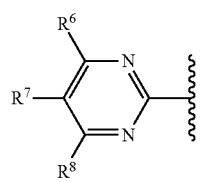

shown in (II-AB) is selected from the group consisting of

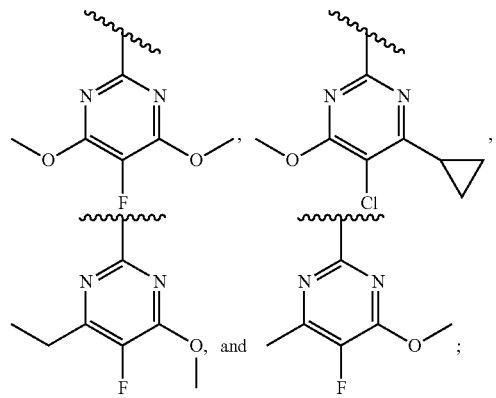

either $R^2$ is F and $R^3$ is H or $R^2$ is H and $R^3$ is F.

10. A compound, or a tautomer thereof, or a pharmaceutically acceptable salt of said compound or said tautomer, said compound being selected from:

| Ex No. | Compound |
|---|---|
| 1 | [structure: spiro pyrrolidine-pyrimidinone with 2,4-difluorophenyl and 5-fluoro-4-methoxy-6-methylpyrimidin-2-yl] |
| 2 | [structure: spiro with 2-chloro-5-fluorophenyl and 5-fluoro-4-methoxy-6-methylpyrimidin-2-yl] |
| 3 | [structure: spiro with 5-chloro-2-fluorophenyl and 5-fluoro-4-methoxy-6-methylpyrimidin-2-yl] |
| 4 | [structure: spiro with phenyl and 4-ethoxy-5-fluoro-6-methylpyrimidin-2-yl] |
| 5 | [structure: spiro with phenyl and 4-ethyl-5-fluoro-6-methylpyrimidin-2-yl] |
| 6 | [structure: spiro with phenyl and 4-ethyl-5-fluoro-6-methoxypyrimidin-2-yl] |
| 7 | [structure: spiro with phenyl and 5-chloro-4-cyclopropyl-6-methylpyrimidin-2-yl] |
| 8 | [structure: spiro with 2,4,5-trifluorophenyl and 5-fluoro-4-methoxy-6-methylpyrimidin-2-yl] |

| Ex No. | Compound |
|---|---|
| 9 | (2,5-difluorophenyl spiro-pyrrolidine imidazolinone linked to 4,6-dimethoxy-5-fluoropyrimidine) |
| 10 | (2,4-difluorophenyl spiro-pyrrolidine imidazolinone linked to 4,6-dimethoxy-5-fluoropyrimidine) |
| 11 | (2,6-difluorophenyl spiro-pyrrolidine imidazolinone linked to 4-methyl-6-methoxy-5-fluoropyrimidine) |
| 12 | (phenyl spiro-pyrrolidine imidazolinone linked to 4-methyl-6-methoxy-5-fluoropyrimidine) |

| Ex No. | Compound |
|---|---|
| 13 | (2,4-difluorophenyl spiro-pyrrolidine imidazolinone linked to 4-methyl-6-methoxy-5-fluoropyrimidine) |
| 14 | (3-cyanophenyl spiro-pyrrolidine imidazolinone linked to 4-methyl-6-cyclopropyl-5-fluoropyrimidine) |
| 15 | (2,5-difluorophenyl spiro-pyrrolidine imidazolinone linked to 4-methyl-6-methoxy-5-fluoropyrimidine) |
| 16 | (2-fluorophenyl spiro-pyrrolidine imidazolinone linked to 4-methyl-6-methoxy-5-fluoropyrimidine) |

-continued

| Ex No. | Compound |
|---|---|
| 17 | (structure with 4-fluorophenyl group, spiro pyrrolidine, and pyrimidine bearing methyl, fluoro, methoxy substituents) |
| 18 | (structure with 2-fluorophenyl group, spiro pyrrolidine, and pyrimidine bearing methyl, chloro, methoxy substituents) |
| 19 | (structure with 2,4-difluorophenyl group, spiro pyrrolidine, and pyrimidine bearing methoxy, chloro, cyclopropyl substituents) |
| 20 | (structure with 4-fluoro-2-chlorophenyl group, spiro pyrrolidine, and pyrimidine bearing methyl, fluoro, methoxy substituents) |

| Ex No. | Compound |
|---|---|
| 21 | (structure with 4-fluorophenyl group, spiro pyrrolidine, and pyrimidine bearing methoxy, fluoro, cyclopropyl substituents) |
| 22 | (structure with 2,4,5-trifluorophenyl group, spiro pyrrolidine, and pyrimidine bearing methoxy, fluoro, ethyl substituents) |
| 23 | (structure with phenyl group, spiro pyrrolidine, and pyrimidine bearing dimethyl and fluoro substituents) |
| 24 | (structure with phenyl group, spiro pyrrolidine, and pyrimidine bearing ethoxy, fluoro, ethyl substituents) |

| Ex No. | Compound |
|---|---|
| 25 | (structure with phenyl, HN, N-CH₃, C=O spiro pyrrolidine, pyrimidine with CH₃, F, cyclopropyl) |
| 26 | (structure with phenyl, HN, N-CH₃, C=O spiro pyrrolidine, pyrimidine with ethyl, Cl, cyclopropyl) |
| 27 | (structure with 4-fluorophenyl, HN, N-CH₃, C=O spiro pyrrolidine, pyrimidine with OCH₃, F, OCH₃) |
| 28 | (structure with 4-fluorophenyl, HN, N-CH₃, C=O spiro pyrrolidine, pyrimidine with CH₃, F, CH₃) |
| 29 | (structure with 2,3,4-trifluorophenyl, HN, N-CH₃, C=O spiro pyrrolidine, pyrimidine with OCH₃, F, CH₃) |
| 30 | (structure with 4-fluorophenyl, HN, N-CH₃, C=O spiro pyrrolidine, pyrimidine with OCH₃, F, ethyl) |
| 31 | (structure with 2,5-difluorophenyl, HN, N-CH₃, C=O spiro pyrrolidine, pyrimidine with ethyl, F, OCH₃) |
| 32 | (structure with 2,4-difluorophenyl, HN, N-CH₃, C=O spiro pyrrolidine, pyrimidine with OCH₃, F, ethyl) |

| Ex No. | Compound |
|---|---|
| 33 | 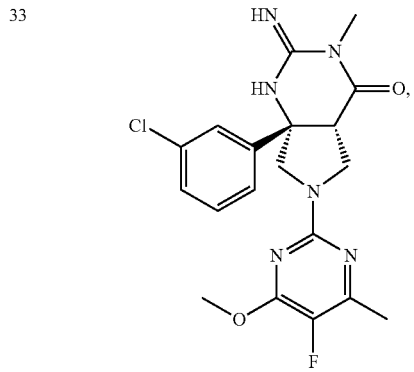 |
| 34 | 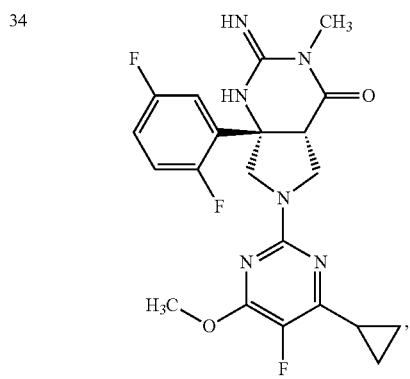 |
| 35 | 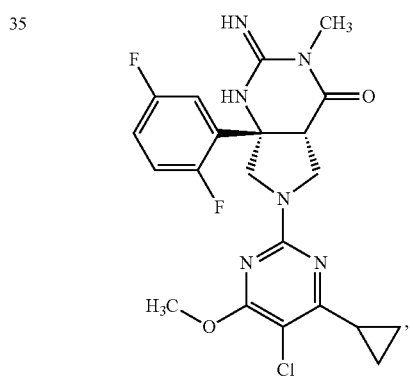 |
| 36 | 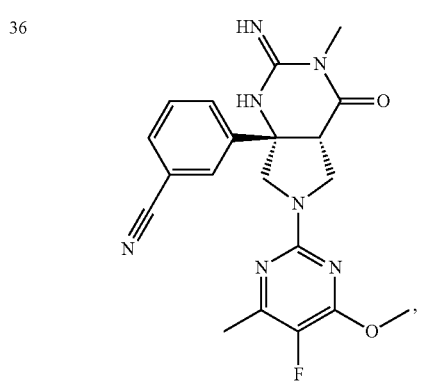 |
| Ex No. | Compound |
|---|---|
| 37 | 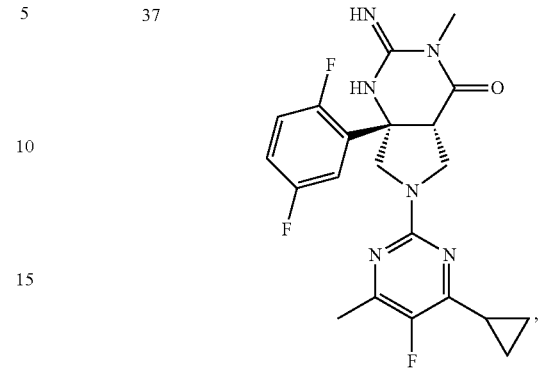 |
| 38 | 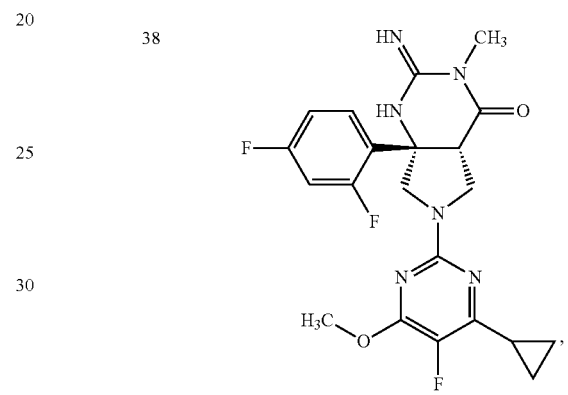 |
| 39 | 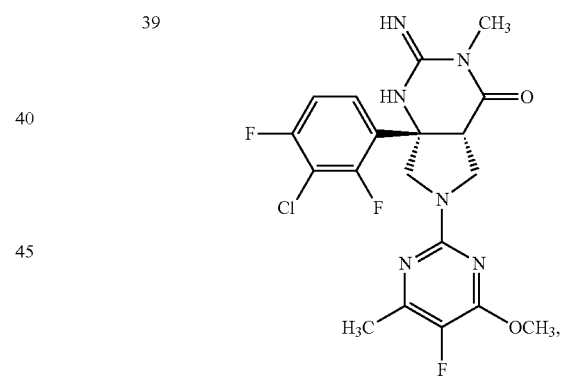 |
| 40 | 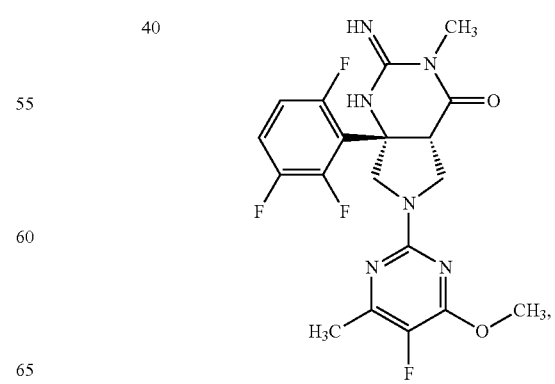 |

| Ex No. | Compound |
|---|---|
| 41 | (structure) |
| 42 | (structure) |
| 43 | (structure) |

| Ex No. | Compound |
|---|---|
| 1 | (structure) |
| 2 | (structure) |
| 8 | (structure) |
| 9 | (structure) |

11. A compound, or a tautomer thereof, or a pharmaceutically acceptable salt of said compound or said tautomer, said compound having a structure selected from:

| Ex No. | Compound |
|---|---|
| 10 | 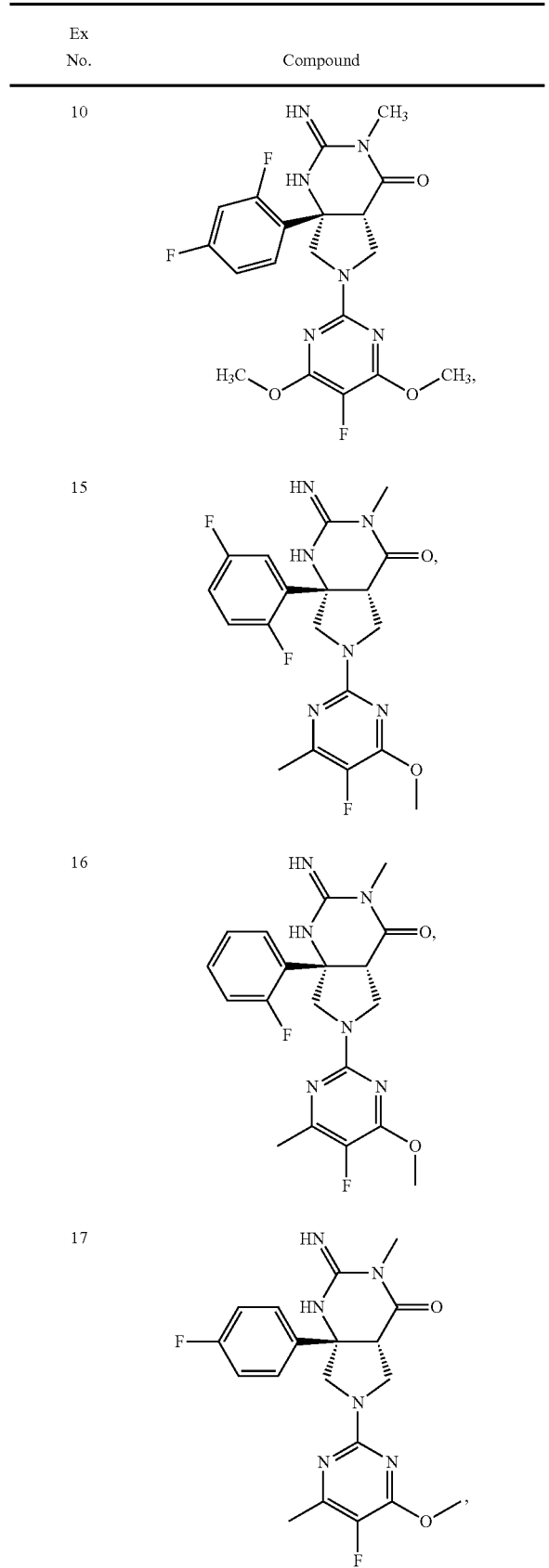 |
| 15 | |
| 16 | |
| 17 | |
| Ex No. | Compound |
|---|---|
| 18 | 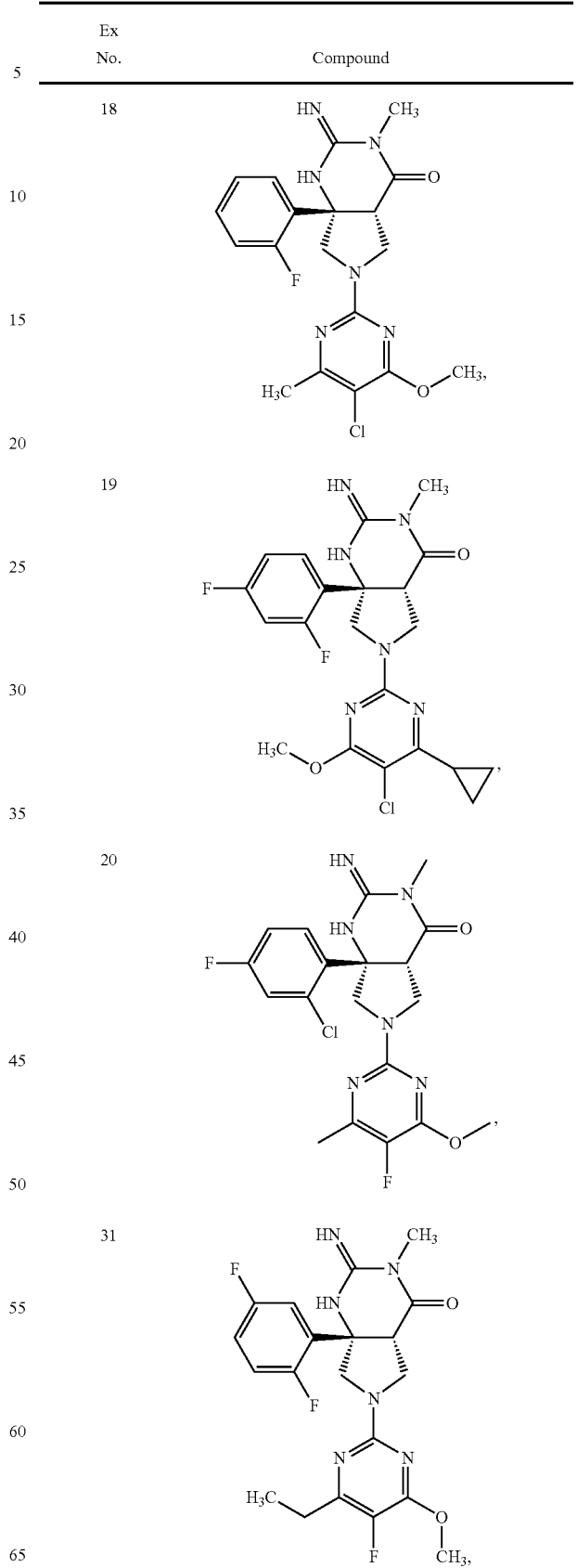 |
| 19 | |
| 20 | |
| 31 | |

-continued

| Ex No. | Compound |
|---|---|
| 35 | 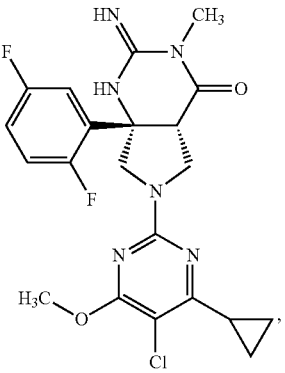 [SMILES: COc1nc(N2C[C@H]3C(=O)N(C)C(=N)N[C@@]3(c3cc(F)ccc3F)C2)nc(C2CC2)c1Cl] |
| 38 | 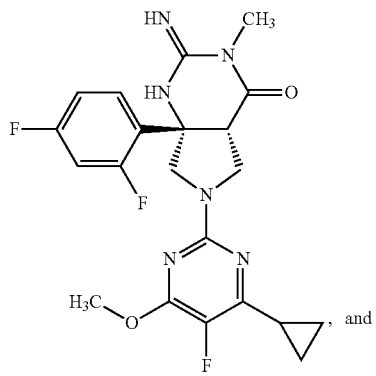 [SMILES: COc1nc(N2C[C@H]3C(=O)N(C)C(=N)N[C@@]3(c3ccc(F)cc3F)C2)nc(C2CC2)c1F] , and |
| 39 | 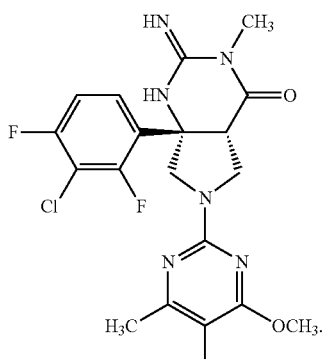 |

12. A compound, or a tautomer thereof, or a pharmaceutically acceptable salt of said compound or said tautomer, said compound having the following structure:

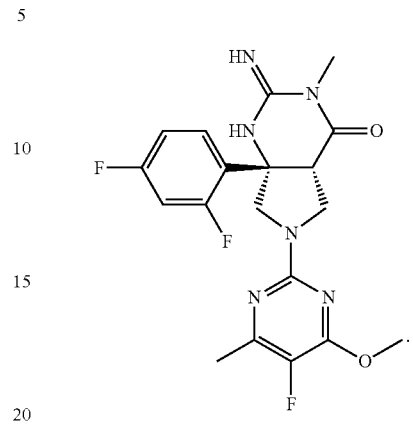

13. A compound, or a tautomer thereof, or a pharmaceutically acceptable salt of said compound or said tautomer, said compound having the following structure:

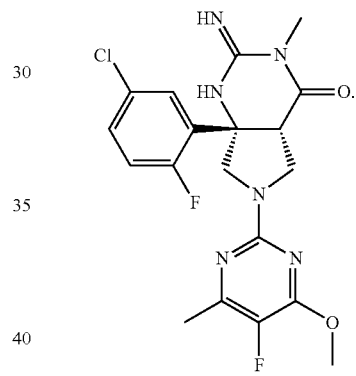

14. A compound, or a tautomer thereof, or a pharmaceutically acceptable salt of said compound or said tautomer, said compound having the following structure:

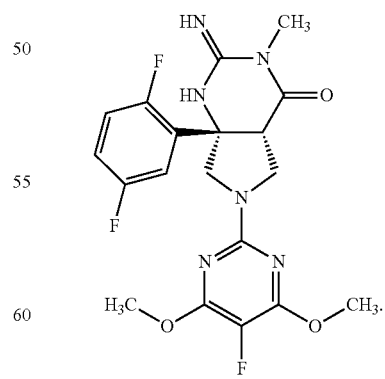

15. A compound, or a tautomer thereof, or a pharmaceutically acceptable salt of said compound or said tautomer, said compound having the following structure:

16. A compound, or a tautomer thereof, or a pharmaceutically acceptable salt of said compound or said tautomer, said compound having the following structure:

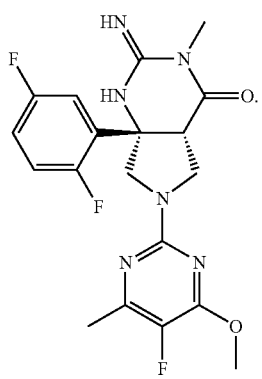 [SMILES: COc1nc(N2C[C@H]3C(=O)N(C)C(=N)N[C@@]3(c3cc(F)ccc3F)C2)nc(C)c1F]

17. A compound, or a tautomer thereof, or a pharmaceutically acceptable salt of said compound or said tautomer, said compound having the following structure:

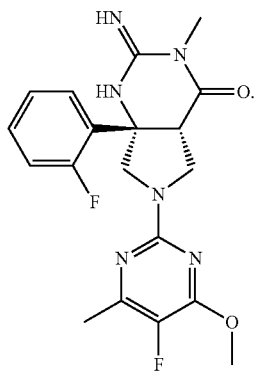 [SMILES: COc1nc(N2C[C@H]3C(=O)N(C)C(=N)N[C@@]3(c3ccccc3F)C2)nc(C)c1F]

18. A deuterated compound, or a tautomer thereof, or a pharmaceutically acceptable salt of said deuterated compound or said tautomer, said deuterated compound having the following structure:

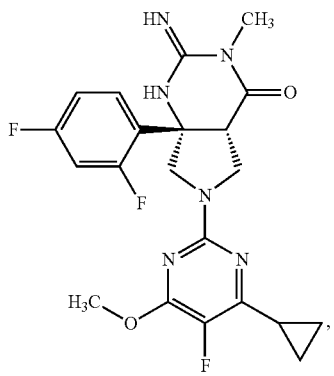 [SMILES: COc1nc(N2C[C@H]3C(=O)N(C)C(=N)N[C@@]3(c3ccc(F)cc3F)C2)nc(C2CC2)c1F]

19. A deuterated compound, or a tautomer thereof, or a pharmaceutically acceptable salt of said deuterated compound or said tautomer, said deuterated compound having the following structure:

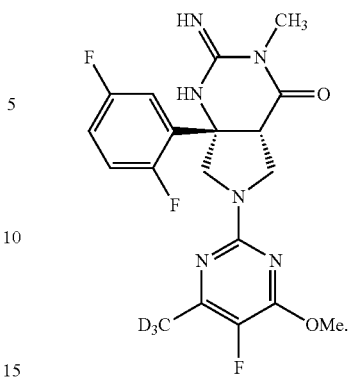

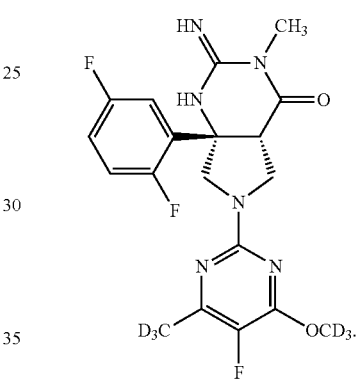

20. A pharmaceutical composition comprising at least one compound of any one of claims 1-19, or a tautomer thereof, or pharmaceutically acceptable salt of said compound or said tautomer, and a pharmaceutically acceptable carrier or diluent.

21. A pharmaceutical composition comprising a compound of any one of claims 1-19, or a tautomer thereof, or a stereoisomer of said compound or said tautomer, or a pharmaceutically acceptable salt thereof, together with at least one additional therapeutic agent, wherein said at least one additional therapeutic agent is at least one agent selected from:

$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

* * * * *